US009315826B2

(12) United States Patent
Hooper

(10) Patent No.: US 9,315,826 B2
(45) Date of Patent: Apr. 19, 2016

(54) NUCLEIC ACIDS CONTAINING A SYNTHETIC CODON-OPTIMIZED SIN NOMBRE VIRUS FULL-LENGTH M GENE

(75) Inventor: Jay Hooper, New Market, MD (US)

(73) Assignee: The United States of America as rep. by the Sec'y of the Army, for U.S. Army Medical Research Institute of Infectious Diseases, Washington, DC (US)

( * ) Notice: Subject to any disclaimer, the term of this patent is extended or adjusted under 35 U.S.C. 154(b) by 0 days.

(21) Appl. No.: 13/982,606

(22) PCT Filed: Jan. 31, 2011

(86) PCT No.: PCT/US2011/023098
§ 371 (c)(1),
(2), (4) Date: Oct. 17, 2013

(87) PCT Pub. No.: WO2012/105931
PCT Pub. Date: Aug. 9, 2012

(65) Prior Publication Data
US 2014/0079731 A1    Mar. 20, 2014

(51) Int. Cl.
*C12N 15/86* (2006.01)
*A61K 39/12* (2006.01)
*A61K 39/00* (2006.01)

(52) U.S. Cl.
CPC ............ *C12N 15/86* (2013.01); *A61K 39/12* (2013.01); *A61K 2039/53* (2013.01); *A61K 2039/70* (2013.01); *C12N 2760/12111* (2013.01); *C12N 2760/12121* (2013.01); *C12N 2760/12122* (2013.01); *C12N 2760/12134* (2013.01)

(58) Field of Classification Search
CPC .................. C12N 15/86; C12N 2760/12134; A61K 39/12
See application file for complete search history.

(56) References Cited

U.S. PATENT DOCUMENTS

| | | |
|---|---|---|
| 4,945,050 A | 7/1990 | Sanford |
| 5,853,980 A | 12/1998 | Rollin |
| 5,916,754 A | 6/1999 | Nichol |
| 5,945,277 A | 8/1999 | Nichol |
| 6,316,250 B1 | 11/2001 | Hjelle |
| 6,451,309 B2 | 9/2002 | Hooper |
| 6,562,376 B2 | 5/2003 | Hooper |
| 6,620,412 B2 | 9/2003 | Hooper |
| 7,217,812 B2 | 5/2007 | Hooper |
| 8,183,358 B2 | 5/2012 | Hooper |
| 2002/0114818 A1 | 8/2002 | Schmaljohn |
| 2004/0053216 A1 | 3/2004 | Hooper |
| 2013/0273170 A1 | 10/2013 | Hooper |

FOREIGN PATENT DOCUMENTS

| | | |
|---|---|---|
| WO | WO 95/19799 | 7/1995 |
| WO | WO 2004/058808 | 7/2004 |
| WO | WO 2008/100508 | 8/2008 |

OTHER PUBLICATIONS

Maes et al., Viral Immunology, 2008, 21(1):49-60.
Maes et al., Expert Review Vaccines, 2009, 8(1):67-76.
Schmaljohn and Hjelle. 1997, Emerg. Infect. Dis., vol. 3, pp. 95-104.
Schmaljohn et al., 1996, In the Bunyaviridae Ed. R. M. Elliott, New York Plenum Press, pp. 63-90.
Lee et al., 1990. Arch, Virol., Suppl 1, pp. 35-47.
Song et al., 1992, Vaccine 10, pp. 214-216.
Lu et al., 1996, J. Med. Virol., 49, pp. 333-335.
Schmaljohn et al., 1990, J. Virol. 64, pp. 3162-3170.
Schmaljohn et al., 1992, Vaccine 10, pp. 10-13.
Xu et al., 1992, Am. J. Trop. Med. Hyg., vol. 47, pp. 397-404.
Yoshimatsu et al., 1993, Arch. Virol., vol. 130, pp. 365-376.
Lundkvist et al., 1996, Virology 216, pp. 397-406.
Ulrich et al., 1998, Vaccine 16, pp. 272-280.
Schmaljohn and Nichols, 2001, Current Topics in Microbiology and Immunology, Hantaviruses, vol. 256, pp. 171-191.
Chu et al., 1995, J. Virol., vol. 69, pp. 6417-6423.
Arikawa et al., 1992, J. Gen. Virol., vol. 70, pp. 615-624.
Eisenbraun, et al., 1993, DNA Cell. Biol., vol. 12, pp. 791-797.
Fynan et al., 1993, PNAS USA, vol. 90, pp. 11478-11482.
Haynes et al., 1994, AIDS Res.Hum.Retroviruses, vol. 10, Supple 2:S43.
Pertmer et al., 1995, Vaccine vol. 13, p. 1427 et seq.
Bos, J.D., 1997, Clin.Exp.Immunol., vol. 107, suppl. 1:3.
Labuda et al., 1996, Virology, 219:357.
Rambukkana et al., 1995, Lab. Invest. 73:521.
Stingl, G., 1993, Recent Results Cancer Res., 128:45.
Evans et al., Vaccine, 2009, vol. 27(18), pp. 2506-2512.
Yager et al., Expert Rev. Vaccines, 2009, vol. 8(9), pp. 1205-1220.
Robinson and Torres, 1997, Semin. Immunol. 9. pp. 271-283.
Gregoriadis, 1998, Pharm. Res. 15, pp. 661-670.
van Drunen et al., Expert Rev. Vaccines, 2010, vol. 9(5), pp. 503-517.
Condon et al., DNA-based immunization by in vivo transfection of dendritic cells, Nat. Med., 1996, 10:1122-1128.
Monteiro-Riviere et al., The pig as a model for . . . , In: tumbleson MD, Schook, LB (eds), Advances in Swine in Biomedical Res., vol. 2, New York, Plemum Press, 1996,425-458.
Draize et al., Methods for the study of irritation . . . , J. Pharmacol. Exp. Ther., 1944, 82:377-390.
Charles River Lab., Arkansas Div., Assessment of the Local Skin Reactivity . . . ,Final Study report for Protocol No. JTA00001 (2005).
Pertmer et al., Vaccine, 1995, 219:357.
International Search Report, dated Jan. 7, 2013, issued in parallel application PCT US2011/023098, 4 pages.
International Preliminary Reprot on Patentabilty, dated Sep. 3, 2013, issued in parallel application PCT US2011/023098, 5 pages.
Bjaradway, et al. "Intramuscular inoculation of Sin Nombre hantavirus cDNAs induces . . . ", Vaccine 17 (1999), pp. 2836-2843.
Bharadway et al., "Genetic vaccines protect against Sin Nombre hantavirus challenge in the deer mouse . . . ", J. General Virology (2002) 83, pp. 1745-1751.

(Continued)

*Primary Examiner* — Jeffrey Parkin

(57) ABSTRACT

The invention contemplates a new synthetic, codon-optimized Sin Nombre virus (SNV) full-length M gene open reading frame (ORF) that encodes a unique consensus amino acid sequence. The SNV ORF was cloned into a plasmid to form the first stable recombinant SNV full-length M gene that elicits neutralizing antibodies. The gene can be engineered into a vaccine system, and is useful to protect mammals against infection with Sin Nombre virus.

8 Claims, 14 Drawing Sheets

(56) References Cited

OTHER PUBLICATIONS

Custer et al.,"Active and Passive Vaccination against Hantavirus Pulmonary Syndrome with Andes Virus M Genome . . . ", J. Virology, Sep. 2003, vol. 77, No. 18, pp. 9894-9905.

Hooper et al., "DNA Vaccination with the Hantaan Virus M Gene Protects Hamsters . . . ", J. Virology, Sep. 2001, No. 75, No. 18, pp. 8469-8477.

Hooper et al., "Immuno Serum Produced by DNA Vaccination Protects Hamsters . . . ", J. Virology, Feb. 2008, vol. 82, No. 3, pp. 1332-1338.

Wahl-Jensen et al., "Temporal Analysis of Andes Virus and Sin Nombre Virus . . . " J. Virology, 84(4), May 2, 2007, pp. 7449-7462.

Barry and Johnston, "Biological features of genetic immunization," Vaccine, vol. 15, No. 8, 1997, pp. 788-791.

Gurunathan et al., "DNA Vaccines: Immunology, Application, and Optimization," Annu.Rev.Immunol., 2000, 18:927-974.

Klinman et al., "Contribution of Cells at the Site of DNA Vaccination to the Generation . . . ", J. Immuno., 1998, 160:2388-2392.

Steele et al, "Cutaneous DNA Vaccination Against Ebola Virus", Veterinary Patholoy 2001, 38:203-215.

Yoshida et al., "Adavantage of gene gun-mediated over intramusculare inoculation of plasmid DNA . . . ", Vaccine 18, (2000) pp. 1725-1729.

Fuller et al., "Preclinical and clinical progress of particle-mediated DNA vaccines . . . ", Science Direct Medods 40 (2006), pp. 86-97.

Brocato et al., "Construction and Nonclinical Testing of a Pujmala Virus Synthetic M Gene-Based . . . ", Clin. Vaccine Immunol. 2013, 20(2), 218 et seq.

Hammerbeck et al., Chap. 23—Hantavirus, in Vaccines for Biodefense and Emerging and Neglected Diseases, 2008, Elsevier Inc., pp. 377-409.

Hooper et al., "Hantaan/Andes virus DNA vaccine elecits a broadly cross-reactive . . . ", Virology 347 (2006), pp. 208-216.

Jonsson et al., "Treatment of hantavirus pulmonary syndrome", Science Direct Antiviral Research 78 (2008) pp. 162-169.

Hooper et al. "A novel Sin Nombre virus DNA vaccine and its inclusion in a candidate pan-hantavirus . . . ", Vaccine 31 (2013), pp. 4314-4321.

Hooper et al., "DNA Vaccination with Hantavirus M Segment Elecits Neutralizing Antibodies . . . ", Virology 255 (1999), pp. 269-278.

McElroy et al., "Andes virus M genome segment is not sufficient to confer the virulence . . . ", Science Direct Virology 326 (2004) pp. 130-139.

Brocato et al., "DNA Vaccine-Generated Duck Polyclonal Antibodies as a Postexposure . . . ", PLoS ONE, vol. 7, No. 4, Apr. 2012, pp. 1-11.

Ray et al., "Study of Andes virus entry and neutralization using a pseudovirion system", J. Virological Methods 163 (2010), pp. 416-423.

Xu et al., Am. J. Trop. Med. Hyg., 47(4), 1992, pp. 397-404.

Hammerbeck, C.D., et al.,Hantavirus. In: Vaccines for Biodefense and Emerging and Neglected Diseases (A.D.T. Barrett and L.R. Stanberry, Eds.), London, pp. 379-411 (2009).

Mean Values for Groups

- ○ pWRG/SN-M(2a)
- ● pWRG/SN-M(opt)

X-axis: Day (0, 14, 28, 42, 56, 70, 84, 98, 112)
Y-axis: SNV PRNT50 Titer (10, 20, 40, 80, 160, 320, 640, 1280, 2560, 5120, 10240, 20480, 40960, 81920)

| | Group 1 | Group 2 | Group 3 |
|---|---|---|---|
| Vaccine: | HFRS mix | HPS mix | HFRS/HPS mix |
| Plasmids: | pWRG/HTN-M(x) | pWRG/SN-M(opt) | pWRG/HTN-M(x) |
| | pWRG/PUU-M(s2) | pWRG/AND-M | pWRG/PUU-M(s2) |
| | | | pWRG/SN-M(opt) |
| | | | pWRG/AND-M |
| Dose | 2 mg | 2 mg | 4 mg |

Fig. 5

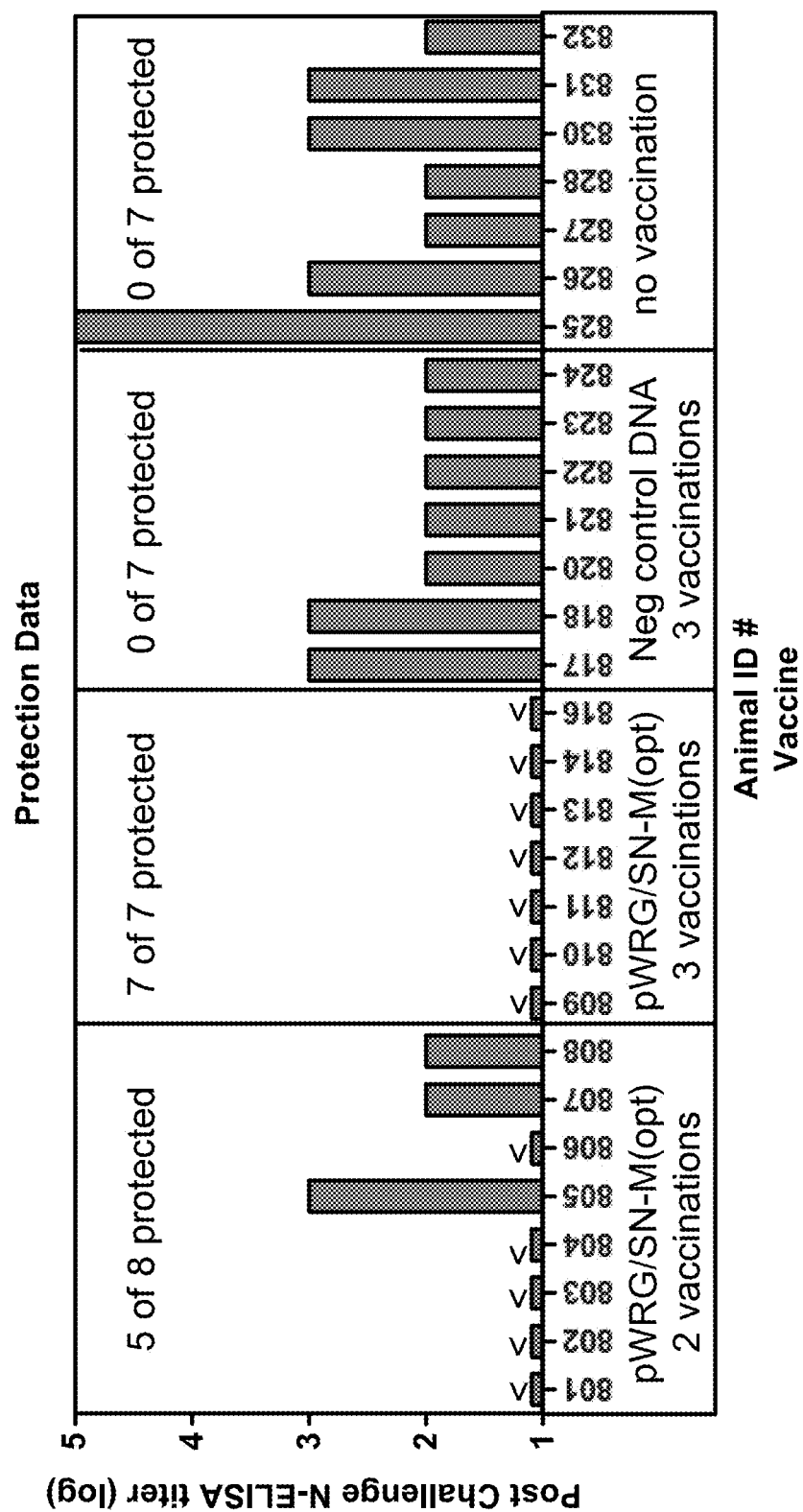

Fig. 7

Pseudovirons made with pWRG/SN-M(opt) are neutralized by SNV immune sera

- ■ Naive rabbit sera
- △ anti-VSV-G
- ○ anti-SNV rabbit sera

Pseudovirion prep 1

Pseudovirion prep 2

Reciprocal Antibody Dilution

SEQUENCE LISTING

<160> NUMBER OF SEQ ID NOS: 22

<210> SEQ ID NO 1
<211> LENGTH: 7938
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gggggggggg ggcgctgagg tctgcctcgt gaagaaggtg ttgctgactc ataccaggcc      60
tgaatcgccc catcatccag ccagaaagtg agggagccac ggttgatgag agctttgttg     120
taggtggacc agttggtgat tttgaacttt tgctttgcca cggaacggtc tgcgttgtcg     180
ggaagatgcg tgatctgatc cttcaactca gcaaagttc gatttattca acaaagccgc     240
cgtcccgtca agtcagcgta atgctctgcc agtgttacaa ccaattaacc aattctgatt     300

-continued

```
agaaaaactc atcgagcatc aaatgaaact gcaatttatt catatcagga ttatcaatac    360
catatttttg aaaagccgt ttctgtaatg aaggagaaaa ctcaccgagg cagttccata     420
ggatggcaag atcctggtat cggtctgcga ttccgactcg tccaacatca atacaaccta   480
ttaatttccc ctcgtcaaaa ataaggttat caagtgagaa atcaccatga gtgacgactg   540
aatccggtga gaatggcaaa agcttatgca tttctttcca gacttgttca acaggccagc   600
cattacgctc gtcatcaaaa tcactcgcat caaccaaacc gttattcatt cgtgattgcg   660
cctgagcgag acgaaatacg cgatcgctgt taaaaggaca attacaaaca ggaatcgaat   720
gcaaccggcg caggaacact gccagcgcat caacaatatt ttcacctgaa tcaggatatt   780
cttctaatac ctggaatgct gttttccggg ggatcgcagt ggtgagtaac catgcatcat   840
caggagtacg gataaaatgc ttgatggtcg gaagaggcat aaattccgtc agccagttta   900
gtctgaccat ctcatctgta acatcattgg caacgctacc tttgccatgt tcagaaaca    960 actctggcgc atcgggcttc ccatacaatc gatagattgt cgcacctgat tgcccgacat   1020
tatcgcgagc ccatttatac ccatataaat cagcatccat gttggaattt aatcgcggcc   1080
tcgagcaaga cgtttcccgt tgaatatggc tcataacacc ccttgtatta ctgtttatgt   1140
aagcagacag ttttattgtt catgatgata tattttatc ttgtgcaatg taacatcaga    1200
gattttgaga cacaacgtgg ctttcccccc ccccccggca tgcctgcagg tcgacaatat   1260
tggctattgg ccattgcata cgttgtatct atatcataat atgtacattt atattggctc   1320
atgtccaata tgaccgccat gttgacattg attattgact agttattaat agtaatcaat   1380 tacgggtca ttagttcata gcccatatat ggagttccgc gttacataac ttacggtaaa    1440
tggcccgcct ggctgaccgc ccaacgaccc ccgcccattg acgtcaataa tgacgtatgt   1500
tcccatagta acgccaatag ggactttcca ttgacgtcaa tgggtggagt atttacggta   1560
aactgcccac ttggcagtac atcaagtgta tcatatgcca gtccgcccc ctattgacgt    1620 caatgacggt aaatggcccg cctggcatta tgcccagtac atgaccttac gggactttcc   1680
tacttggcag tacatctacg tattagtcat cgctattacc atggtgatgc ggttttggca   1740
gtacaccaat gggcgtggat agcggtttga ctcacgggga tttccaagtc tccacccat    1800 tgacgtcaat gggagtttgt tttggcacca aaatcaacgg gactttccaa aatgtcgtaa   1860
taaccccgcc ccgttgacgc aaatgggcgg taggcgtgta cggtgggagg tctatataag   1920
cagagctcgt ttagtgaacc gtcagatcgc ctggagacgc catccacgct gttttgacct   1980
ccatagaaga caccgggacc gatccagcct ccgcggccgg gaacggtgca ttggaacgcg   2040
gattccccgt gccaagagtg acgtaagtac cgcctataga ctctataggc acaccccttt   2100
ggctcttatg catgctatac tgttttggc ttggggccta tacaccccg cttccttatg     2160 ctataggtga tggtatagct tagcctatag gtgtgggtta ttgaccatta ttgaccactc   2220
ccctattggt gacgatactt tccattacta atccataaca tggctctttg ccacaactat   2280
ctctattggc tatatgccaa tactctgtcc ttcagagact gacacggact ctgtattttt   2340
acaggatggg gtcccatttta ttatttacaa attcacatat acaacaacgc cgtccccgt   2400 gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
```

```
tctgaaaatg agctcggaga ttgggctcgc accgctgacg cagatggaag acttaaggca   2700
gcggcagaag aagatgcagg cagctgagtt gttgtattct gataagagtc agaggtaact   2760
cccgttgcgg tgctgttaac ggtggagggc agtgtagtct gagcagtact cgttgctgcc   2820
gcgcgcgcca ccagacataa tagctgacag actaacagac tgttcctttc catgggtctt   2880
ttctgcagtc accgtccaag cttgcggccg cggatctgca ggaattcggc acgagagtag   2940
tagactccgc acgaagaagc aaacactgaa taaaggatat acagaatggt gggctgggtg   3000
tgcatcttcc tggtggtgct gaccaccgcc acagccggcc tgacccggaa cctgtacgag   3060
ctgaagatcg agtgccccca caccgtgggc ctgggccagg ctacgtgac cggcagcgtg     3120
gagacaaccc ccatcctgct gacccaggtg gccgacctga agattgagag cagctgcaac   3180
ttcgacctgc acgtgcccgc caccaccacc cagaaataca accaggtgga ctggaccaag   3240
aagagcagca ccaccgagag caccaacgcc ggagccacca ccttcgaggc caagaccaaa   3300
gaagtgaacc tgaagggcac ctgcaacatc cccccccacca catttgaggc cgcctacaag   3360
agcagaaaga ccgtgatctg ctacgacctg gcctgcaacc agacccactg cctgcccacc   3420
gtgcacctga tcgcccccgt gcagacctgc atgagcgtgc ggagctgcat gatcggcctg   3480
ctgtccagcc ggatccaggt gatctacgag aaaacctact gcgtgaccgg ccagctgatc   3540
gagggcctgt gcttcatccc cacccacaca atcgccctga cccagcccgg ccacacctac   3600
gacaccatga ccctgcccgt gacctgcttt ctggtggcca agaagctggg cacccagctg   3660
aagctggccg tggagctgga aaagctgatc accggcgtga gctgcaccga aacagcttc    3720
cagggctact acatctgctt catcggcaag cacagcgagc ccctgttcgt gcccaccatg   3780
gaagattaca aagcgccga gctgttcacc cggatggtgc tgaaccccag gggcgaggac    3840
cacgaccccg accagaacgg ccagggcctg atgcggatcg ccggaccgt gaccgccaag    3900
gtgcccagca ccgagacaac cgaaaccatg cagggcattg ccttcgccgg agccccatg    3960
tacagcagct tcagcacact ggtgcggaag gccgaccccg agtacgtgtt cagccccggc   4020
atcattgccg agagcaacca cagcgtgtgc gacaagaaaa ccgtgcccct gacctggacc   4080
ggcttcctgg ccgtgagcgg cgagatcgag cggatcaccg gctgcaccgt gttctgcacc   4140
ctggccggac ctggcgccag ctgcgaggcc tacagcgaga caggcatctt caacatcagc   4200
agccccacct gcctggtgaa caaggtgcag aagttccggg gcagcgagca gcggatcaac   4260
ttcatgtgcc agcgggtgga ccaggacgtg gtggtgtact gcaacggcca gaaaaaagtg   4320
atcctgacca agaccctggt gatcggccag tgcatctaca ccttcaccag cctgttcagc   4380
ctgatccctg gcgtggctca tagcctggca gtcgaactgt gcgtgcctgg cctgcacgga   4440
tgggccacca ccgccctgct gatcaccttc tgcttcggct ggctgctgat ccccacagtg   4500
accctgatca tcctgaagat cctgcggctg ctgacccttca gctgcagcca ctacagcacc   4560
gagtccaagt tcaaagtgat tctggaacgc gtgaaggtgg agtaccagaa aaccatgggc   4620
agcatggtgt gcgacatctg ccaccacgag tgcgagacac ccaaagagct ggaaacccac   4680
aagaagagct gccccgaggg ccagtgcccc tactgcatga ccatcacaga gagcaccgag   4740
agcgccctgc aggcccactt cagcatctgc aagctgacca accggttcca ggaaaacctg   4800
aagaagagcc tgaagcggcc cgaagtgcgg aagggctgct accggaccct gggcgtgttc   4860
cggtacaaga gccggtgcta tgtgggcctg gtgtgggggca ttctgctgac cacagagctg   4920
atcatctggg ccgccagcgc cgacaccccc ctgatggaaa gcgggtggag cgacaccgct   4980
catggcgtgg gaatcgtgcc catgaaaacc gacctggaac tggacttcgc cctggccagc   5040
```

```
agcagcagct acagctaccg gcggaagctg gtgaaccccg ccaaccagga agagacactg    5100
cccttccact tccaactgga caagcaggtg gtgcacgccg agatccagaa cctgggccac    5160
tggatggacg gcaccttcaa tatcaagacc gccttccact gctacggcga gtgcaagaag    5220
tacgcctacc cctggcagac cgccaagtgc ttcttcgaga aggactacca gtacgagaca    5280
agctggggct gcaacccccc cgactgtcct ggcgtgggca ccggctgtac cgcctgcggc    5340
gtgtacctgg acaagctgcg gagcgtgggc aaggcctaca agatcgtgtc cctgaagtac    5400
acccggaaag tgtgcatcca gctgggcaca gagcagacat gcaagcacat cgacgtgaac    5460
gattgcctgg tgaccccag cgtgaaagtc tgtatgattg caccatcag caagctgcag    5520
cccggcgata ccctgctgtt cctgggcccc ctggaacagg gcggcatcat tctgaagcag    5580
tggtgtacca cctcctgcgt gttcggcgac cccggcgaca tcatgagcac cacctccggc    5640
atgcggtgcc ccgagcacac cggcagcttc ggaagattt gtggcttcgc caccacccct    5700
acctgcgagt accagggcaa caccgtgtcc ggcttccagc ggatgatggc cacccgggat    5760
agcttccaga gcttcaacgt gaccgagccc cacatcacca gcaaccggct ggaatggatc    5820
gaccccgaca gcagcatcaa ggaccacatc aacatggtgc tcaatcggga cgtgagcttc    5880
caggacctga gcgacaaccc ctgcaaggtg gacctgcaca cccagagcat cgacggcgcc    5940
tggggcagcg gcgtgggctt cacactggtg tgcacagtgg gcctgaccga gtgcgccaac    6000
ttcatcacct ccatcaaggc ctgcgacagc gccatgtgct acggcgccac cgtgaccaac    6060
ctgctgcggg gctccaacac agtgaaggtg gtgggcaagg gcggccacag cggcagcctg    6120
tttaagtgct gccacgacac cgactgcacc gaggaaggcc tggccgccag ccccccctcac   6180
ctggacagag tgaccggcta caaccagatc gacagcgaca aggtgtacga cgatggcgcc    6240
cctccctgca ccatcaagtg ctggttcacc aagagcggcg agtggctgct gggcatcctg    6300
aacggcaact gggtcgtcgt ggccgtgctg atcgtgatcc tgatcctgtc tatcctgctg    6360
ttcagcttct tctgccccgt gcggaaccgg aagaacaagg ccaactagca acatatatg    6420
taagtaaggg tatgatcata ttatatcatt atgcgtatac tcttatatct ataatatcta    6480
tgtatcctta tactctaact atttatatta atttttactt ttatacaagt attaactaac    6540
ccattaccag ctaaaaaaaa caaacccta cacctatat aatcccattt gcttattacg    6600
aggcttttgt tcctgcggag tctactacta agatctacgt atgatcagcc tcgactgtgc    6660
cttctagttg ccagccatct gttgtttgcc cctccccgt gccttccttg accctggaag    6720
gtgccactcc cactgtcctt tcctaataaa atgaggaaat tgcatcgcat tgtctgagta    6780
ggtgtcattc tattctgggg ggtggggtgg ggcaggacag caaggggag gattgggaag    6840
acaatagcag gcatgctggg gatgcggtgg gctctatggc ttctgaggcg gaaagaacca    6900
gctgggctc gacagctcga ctctagaatt gcttcctcgc tcactgactc gctgcgctcg    6960
gtcgttcggc tgcggcgagc ggtatcagct cactcaaagg cggtaatacg gttatccaca    7020
gaatcagggg ataacgcagg aaagaacatg tgagcaaaag gccagcaaaa ggccaggaac    7080
cgtaaaaagg ccgcgttgct ggcgtttttc cataggctcc gcccccctga cgagcatcac    7140
aaaaatcgac gctcaagtca gaggtggcga aacccgacag gactataaag ataccaggcg    7200
tttccccctg gaagctccct cgtgcgctct cctgttccga ccctgccgct taccggatac    7260
ctgtccgcct ttctcccttc gggaagcgtg gcgctttctc atagctcacg ctgtaggtat    7320
ctcagttcgg tgtaggtcgt tcgctccaag ctgggctgtg tgcacgaacc ccccgttcag    7380
```

-continued

```
cccgaccgct gcgccttatc cggtaactat cgtcttgagt ccaacccggt aagacacgac      7440
ttatcgccac tggcagcagc cactggtaac aggattagca gagcgaggta tgtaggcggt      7500
gctacagagt tcttgaagtg gtggcctaac tacggctaca ctagaagaac agtatttggt      7560
atctgcgctc tgctgaagcc agttaccttc ggaaaaagag ttggtagctc ttgatccggc      7620
aaacaaacca ccgctggtag cggtggtttt tttgtttgca agcagcagat tacgcgcaga      7680
aaaaaaggat ctcaagaaga tcctttgatc ttttctacgg ggtctgacgc tcagtggaac      7740
gaaaactcac gttaagggat tttggtcatg agattatcaa aaaggatctt cacctagatc      7800
cttttaaatt aaaaatgaag ttttaaatca atctaaagta tatatgagta aacttggtct      7860
gacagttacc aatgcttaat cagtgaggca cctatctcag cgatctgtct atttcgttca      7920
tccatagttg cctgactc                                                    7938
```

```
<210> SEQ ID NO 2
<211> LENGTH: 3733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
```

```
gcggccgcgg atctgcagga attcggcacg agagtagtag actccgcacg aagaagcaaa      60
cactgaataa aggatataca gaatggtggg ctgggtgtgc atcttcctgg tggtgctgac     120
caccgccaca gccggcctga cccggaacct gtacgagctg aagatcgagt gcccccacac     180
cgtgggcctg ggccagggct acgtgaccgg cagcgtggag acaaccccca tcctgctgac     240
ccaggtggcc gacctgaaga ttgagagcag ctgcaacttc gacctgcacg tgcccgccac     300
caccacccag aaatacaacc aggtggactg gaccaagaag agcagcacca ccgagagcac     360
caacgccgga gccaccacct tgaggccaa gaccaaagaa gtgaacctga gggcacctg      420 caacatcccc cccaccacat tgaggccgc ctacaagagc agaaagaccg tgatctgcta     480
cgacctggcc tgcaaccaga cccactgcct gccaccgtg cacctgatcg cccccgtgca     540
gacctgcatg agcgtgcgga gctgcatgat cggcctgctg tccagccgga tccaggtgat      600
ctacagaaaa acctactgcg tgaccggcca gctgatcgag ggcctgtgct tcatccccac      660
ccacacaatc gccctgaccc agcccggcca cacctacgac accatgaccc tgcccgtgac     720
ctgctttctg gtggccaaga agctgggcac ccagctgaag ctggccgtgg agctggaaaa     780
gctgatcacc ggcgtgagct gcaccgagaa cagcttccag ggctactaca tctgcttcat      840
cggcaagcac agcgagcccc tgttcgtgcc caccatggaa gattacagaa gcgccgagct      900
gttcacccgc atggtgctga cccccagggg cgaggaccac gaccccgacc agaacggcca      960
gggcctgatg cggatcgccg accccgtgac cgccaaggtg cccagcaccg agacaaccga     1020
aaccatgcag ggcattgcct tcgcggagc ccccatgtac agcagcttca gcaccctggt     1080
gcggaaggcc gaccccgagt acgtgttcag ccccggcatc attgccgaga gcaaccacag     1140
cgtgtgcgac aagaaaaccg tgccctgac ctgaccggc ttcctggccg tgagcggcga     1200
gatcgagcgg atcaccggct gcaccgtgtt ctgcaccctg gccggacctg cgccagctg     1260 cgaggcctac agcgagacag gcatcttcaa catcagcagc cccacctgcc tggtgaacaa     1320
ggtgcagaag ttccgggca gcgagcagcg gatcaacttc atgtgccagc gggtggacca     1380
ggacgtggtg gtgtactgca acggccagaa aaaagtgatc ctgaccaaga ccctggtgat     1440
```

```
cggccagtgc atctacacct tcaccagcct gttcagcctg atccctggcg tggctcatag    1500
cctggcagtc gaactgtgcg tgcctggcct gcacggatgg gccaccaccg ccctgctgat    1560
caccttctgc ttcggctggc tgctgatccc cacagtgacc ctgatcatcc tgaagatcct    1620
gcggctgctg accttcagct gcagccacta cagcaccgag tccaagttca agtgattct    1680 ggaacgcgtg aaggtggagt accagaaaac catgggcagc atggtgtgcg acatctgcca    1740
ccacgagtgc gagacagcca aagagctgga acccacaag aagagctgcc ccagggcca    1800 gtgccctac tgcatgacca tcacagagag caccgagagc gccctgcagg cccacttcag    1860
catctgcaag ctgaccaacc ggttccagga aaacctgaag aagagcctga gcggcccga    1920 agtgcggaag ggctgctacc ggaccctggg cgtgttccgg tacaagagcc ggtgctatgt    1980
gggcctggtg tggggcattc tgctgaccac agagctgatc atctgggccg ccagcgccga    2040
cacccccctg atggaaagcg ggtggagcga caccgctcat ggcgtgggaa tcgtgcccat    2100
gaaaaccgac ctggaactgg acttcgccct ggccagcagc agcagctaca gctaccggcg    2160
gaagctggtg aaccccgcca accaggaaga cactgccc ttccacttcc aactggacaa    2220
gcaggtggtg cacgccgaga tccagaacct gggccactgg atggacggca ccttcaatat    2280
caagaccgcc ttccactgct acggcgagtg caagaagtac gcctacccct ggcagaccgc    2340
caagtgcttc ttcgagaagg actaccagta cgagacaagc tggggctgca acccccccga    2400
ctgtcctggc gtgggcaccg gctgtaccgc ctgcggcgtg tacctggaca gctgcggag    2460 cgtgggcaag gcctacaaga tcgtgtcct gaagtacacc cggaaagtgt gcatccagct    2520
gggcacagag cagacatgca agcacatcga cgtgaacgat gcctggtga ccccagcgt    2580 gaaagtctgt atgattggca ccatcagcaa gctgcagccc ggcgatccc tgctgttcct    2640 gggcccctg aacagggcg gcatcattct gaagcagtgg tgtaccaccct cctgcgtgtt    2700 cggcgaccc ggcgacatca tgagcaccac ctccggcatg cggtgccccg agcacaccgg    2760
cagcttccgg aagatttgtg gcttcgccac caccctacc tgcgagtacc agggcaacac    2820
cgtgtccggc ttcagcgga tgatggccac ccgggatagc ttccagagct caacgtgac    2880 cgagccccac atcaccagca accggctgga atggatcgac cccgacagca gcatcaagga    2940
ccacatcaac atggtgctca atcgggacgt gagcttccag gacctgagcg acaacccctg    3000
caaggtggac ctgcacaccc agagcatcga cggcgcctgg ggcagcggcg tgggcttcac    3060
actggtgtgc acagtgggcc tgaccgagtg cgccaacttc atcacctcca tcaaggcctg    3120
cgacagcgcc atgtgctacg cgccaccgt gaccaacctg ctgcggggct ccaacacagt    3180
gaaggtggtg ggcaagggcg ccacagcgg cagcctgttt aagtgctgcc acgacaccga    3240
ctgcaccgag gaaggcctgg ccgccagccc ccctcacctg gacagagtga ccggctacaa    3300
ccagatcgac agcgacaagg tgtacgacga tggcgcccct ccctgcacca tcaagtgctg    3360
gttcaccaag agcggcgagt ggctgctggg catcctgaac ggcaactggg tcgtcgtggc    3420
cgtgctgatc gtgatcctga tcctgtctat cctgctgttc agcttcttct gcccgtgcg    3480 gaaccggaag aacaaggcca actagcaaac atatatgtaa gtaagggtat gatcatatta    3540
tatcattatg cgtatactct tatatctata atatctatgt atccttatac tctaactatt    3600
tatattaatt tttactttta tacaagtatt aactaaccca ttaccagcta aaaaaaacaa    3660 accccttaaca cctatataat cccatttgct tattacgagg cttttgttcc tgcggagtct    3720
actactaaga tct                                                       3733
```

<210> SEQ ID NO 3
<211> LENGTH: 3423
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | | | | | |
|---|---|---|---|---|---|
| atggtgggct | gggtgtgcat | cttcctggtg | gtgctgacca | ccgccacagc | cggcctgacc | 60 |
| cggaacctgt | acgagctgaa | gatcgagtgc | ccccacaccg | tgggcctggg | ccagggctac | 120 |
| gtgaccggca | gcgtggagac | aaccccatc | ctgctgaccc | aggtggccga | cctgaagatt | 180 |
| gagagcagct | gcaacttcga | cctgcacgtg | cccgccacca | ccacccagaa | atacaaccag | 240 |
| gtggactgga | ccaagaagag | cagcaccacc | gagagcacca | acgccggagc | caccaccttc | 300 |
| gaggccaaga | ccaaagaagt | gaacctgaag | ggcacctgca | acatcccccc | caccacattt | 360 |
| gaggccgcct | acaagagcag | aaagaccgtg | atctgctacg | acctggcctg | caaccagacc | 420 |
| cactgcctgc | ccaccgtgca | cctgatcgcc | ccgtgcaga | cctgcatgag | cgtgcggagc | 480 |
| tgcatgatcg | gcctgctgtc | cagccggatc | caggtgatct | acgagaaaac | ctactgcgtg | 540 |
| accggccagc | tgatcgaggg | cctgtgcttc | atccccaccc | acacaatcgc | cctgacccag | 600 |
| cccggccaca | cctacgacac | catgaccctg | cccgtgacct | gctttctggt | ggccaagaag | 660 |
| ctgggcaccc | agctgaagct | ggccgtggag | ctggaaaagc | tgatcaccgg | cgtgagctgc | 720 |
| accgagaaca | gcttccaggg | ctactacatc | tgcttcatcg | gcaagcacag | cgagcccctg | 780 |
| ttcgtgccca | ccatggaaga | ttacagaagc | gccgagctgt | tcacccggat | ggtgctgaac | 840 |
| cccaggggcg | aggaccacga | ccccgaccag | aacggccagg | cctgatgcg | atcgccgga | 900 |
| cccgtgaccg | ccaaggtgcc | cagcaccgag | acaaccgaaa | ccatgcaggg | cattgccttc | 960 |
| gccggagccc | ccatgtacag | cagcttcagc | accctggtgc | ggaaggccga | ccccgagtac | 1020 |
| gtgttcagcc | ccggcatcat | tgccgagagc | aaccacagcg | tgtgcgacaa | gaaaaccgtg | 1080 |
| cccctgacct | ggaccggctt | cctggccgtg | agcggcgaga | tcgagcggat | caccggctgc | 1140 |
| accgtgttct | gcaccctggc | cggacctggc | gccagctgcg | aggcctacag | cgagacaggc | 1200 |
| atcttcaaca | tcagcagccc | cacctgcctg | gtgaacaagg | tgcagaagtt | ccggggcagc | 1260 |
| gagcagcgga | tcaacttcat | gtgccagcgg | gtggaccagg | acgtggtggt | gtactgcaac | 1320 |
| ggccagaaaa | aagtgatcct | gaccaagacc | ctggtgatcg | ccagtgcat | ctacaccttc | 1380 |
| accagcctgt | tcagcctgat | ccctggcgtg | gctcatagcc | tggcagtcga | actgtgcgtg | 1440 |
| cctggcctgc | acggatgggc | caccaccgcc | ctgctgatca | ccttctgctt | cggctggctg | 1500 |
| ctgatcccca | cagtgaccct | gatcatcctg | aagatcctgc | ggctgctgac | cttcagctgc | 1560 |
| agccactaca | gcaccgagtc | caagttcaaa | gtgattctgg | aacgcgtgaa | ggtggagtac | 1620 |
| cagaaaacca | tgggcagcat | ggtgtgcgac | atctgccacc | acgagtgcga | cagcaaa | 1680 |
| gagctggaaa | cccacaagaa | gagctgcccc | gagggccagt | gccctactg | catgaccatc | 1740 |
| acagagagca | ccgagagcgc | cctgcaggcc | cacttcagca | tctgcaagct | gaccaaccgg | 1800 |
| ttccaggaaa | acctgaagaa | gagcctgaag | cggcccgaag | tgcggaaggg | ctgctaccgg | 1860 |
| accctgggcg | tgttccggta | caagagccgg | tgctatgtgg | gctggtgtg | gggcattctg | 1920 |
| ctgaccacag | agctgatcat | ctgggccgcc | agcgccgaca | ccccctgat | ggaaagcggg | 1980 |
| tggagcgaca | ccgctcatgg | cgtgggaatc | gtgcccatga | aaaccgacct | ggaactggac | 2040 |
| ttcgccctgg | ccagcagcag | cagctacagc | taccggcgga | agctggtgaa | ccccgccaac | 2100 |

```
caggaagaga cactgccctt ccacttccaa ctggacaagc aggtggtgca cgccgagatc    2160
cagaacctgg gccactggat ggacggcacc ttcaatatca agaccgcctt ccactgctac    2220
ggcgagtgca agaagtacgc ctacccctgg cagaccgcca agtgcttctt cgagaaggac    2280
taccagtacg agacaagctg gggctgcaac ccccccgact gtcctggcgt gggcaccggc    2340
tgtaccgcct gcggcgtgta cctggacaag ctgcggagcg tgggcaaggc ctacaagatc    2400
gtgtccctga agtacacccg gaaagtgtgc atccagctgg gcacagagca gacatgcaag    2460
cacatcgacg tgaacgattg cctggtgacc cccagcgtga agtctgtat gattggcacc    2520 atcagcaagc tgcagcccgg cgataccctg ctgttcctgg gccccctgga cagggcggc    2580 atcattctga agcagtggtg taccacctcc tgcgtgttcg gcgaccccgg cgacatcatg    2640
agcaccacct ccggcatgcg gtgccccgag cacaccggca gcttccggaa gatttgtggc    2700
ttcgccacca ccccctacct cgagtaccag ggcaacaccg tgtccggctt ccagcggatg    2760
atggccaccc gggatagctt ccagagcttc aacgtgaccg agccccacat caccagcaac    2820
cggctggaat ggatcgaccc cgacagcagc atcaaggacc acatcaacat ggtgctcaat    2880
cgggacgtga gcttccagga cctgagcgac aaccccctgca aggtggacct gcacacccag    2940
agcatcgacg gcgcctgggg cagcggcgtg ggcttcacac tggtgtgcac agtgggcctg    3000
accgagtgcg ccaacttcat cacctccatc aaggcctgcg acagcgccat gtgctacggc    3060
gccaccgtga ccaacctgct gcggggctcc aacacagtga aggtggtggg caagggcggc    3120
cacagcggca gcctgtttaa gtgctgccac gacaccgact gcaccgagga aggcctggcc    3180
gccagccccc ctcacctgga cagagtgacc ggctacaacc agatcgacag cgacaaggtg    3240
tacgacgatg gcgcccctcc ctgcaccatc aagtgctggt tcaccaagag cggcgagtgg    3300
ctgctgggca tcctgaacgg caactgggtc gtcgtggccg tgctgatcgt gatcctgatc    3360
ctgtctatcc tgctgttcag cttcttctgc cccgtgcgga accggaagaa caaggccaac    3420
tag                                                                 3423
```

<210> SEQ ID NO 4
<211> LENGTH: 1140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95

Ala Thr Thr Phe Glu Ala Lys Thr Lys Glu Val Asn Leu Lys Gly Thr
            100                 105                 110

-continued

```
Cys Asn Ile Pro Pro Thr Thr Phe Glu Ala Ala Tyr Lys Ser Arg Lys
            115                 120                 125

Thr Val Ile Cys Tyr Asp Leu Ala Cys Asn Gln Thr His Cys Leu Pro
        130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Val Thr Ala
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
            340                 345                 350

Ser Val Cys Asp Lys Lys Thr Val Pro Leu Thr Trp Thr Gly Phe Leu
        355                 360                 365

Ala Val Ser Gly Glu Ile Glu Arg Ile Thr Gly Cys Thr Val Phe Cys
    370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Val Thr Leu Ile Ile Leu Lys Ile
            500                 505                 510

Leu Arg Leu Leu Thr Phe Ser Cys Ser His Tyr Ser Thr Glu Ser Lys
        515                 520                 525

Phe Lys Val Ile Leu Glu Arg Val Lys Val Glu Tyr Gln Lys Thr Met
```

-continued

```
            530                 535                 540
Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Ile Thr Glu Ser Thr Glu Ser Ala Leu Gln Ala His Phe
                    580                 585                 590

Ser Ile Cys Lys Leu Thr Asn Arg Phe Gln Glu Asn Leu Lys Lys Ser
                595                 600                 605

Leu Lys Arg Pro Glu Val Arg Lys Gly Cys Tyr Arg Thr Leu Gly Val
            610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                    645                 650                 655

Met Glu Ser Gly Trp Ser Asp Thr Ala His Gly Val Gly Ile Val Pro
                660                 665                 670

Met Lys Thr Asp Leu Glu Leu Asp Phe Ala Leu Ala Ser Ser Ser Ser
            675                 680                 685

Tyr Ser Tyr Arg Arg Lys Leu Val Asn Pro Ala Asn Gln Glu Glu Thr
690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                    725                 730                 735

Phe His Cys Tyr Gly Glu Cys Lys Lys Tyr Ala Tyr Pro Trp Gln Thr
                740                 745                 750

Ala Lys Cys Phe Phe Glu Lys Asp Tyr Gln Tyr Glu Thr Ser Trp Gly
            755                 760                 765

Cys Asn Pro Pro Asp Cys Pro Gly Val Gly Thr Gly Cys Thr Ala Cys
770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
                805                 810                 815

Gln Thr Cys Lys His Ile Asp Val Asn Asp Cys Leu Val Thr Pro Ser
                820                 825                 830

Val Lys Val Cys Met Ile Gly Thr Ile Ser Lys Leu Gln Pro Gly Asp
            835                 840                 845

Thr Leu Leu Phe Leu Gly Pro Leu Glu Gln Gly Gly Ile Ile Leu Lys
850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
                900                 905                 910

Thr Val Ser Gly Phe Gln Arg Met Met Ala Thr Arg Asp Ser Phe Gln
            915                 920                 925

Ser Phe Asn Val Thr Glu Pro His Ile Thr Ser Asn Arg Leu Glu Trp
930                 935                 940

Ile Asp Pro Asp Ser Ser Ile Lys Asp His Ile Asn Met Val Leu Asn
945                 950                 955                 960
```

```
Arg Asp Val Ser Phe Gln Asp Leu Ser Asp Asn Pro Cys Lys Val Asp
            965                 970                 975

Leu His Thr Gln Ser Ile Asp Gly Ala Trp Gly Ser Gly Val Gly Phe
        980                 985                 990

Thr Leu Val Cys Thr Val Gly Leu  Thr Glu Cys Ala Asn  Phe Ile Thr
        995                 1000                1005

Ser Ile  Lys Ala Cys Asp  Ser  Ala Met Cys Tyr Gly  Ala Thr Val
    1010                 1015                1020

Thr Asn  Leu Leu Arg Gly Ser  Asn Thr Val Lys Val  Val Gly Lys
    1025                1030                 1035

Gly Gly  His Ser Gly Ser Leu  Phe Lys Cys Cys His  Asp Thr Asp
    1040                1045                 1050

Cys Thr  Glu Glu Gly Leu Ala  Ala Ser Pro Pro His  Leu Asp Arg
    1055                1060                1065

Val Thr  Gly Tyr Asn Gln Ile  Asp Ser Asp Lys Val  Tyr Asp Asp
    1070                1075                1080

Gly Ala  Pro Pro Cys Thr Ile  Lys Cys Trp Phe Thr  Lys Ser Gly
    1085                1090                1095

Glu Trp  Leu Leu Gly Ile Leu  Asn Gly Asn Trp Val  Val Val Ala
    1100                1105                1110

Val Leu  Ile Val Ile Leu Ile  Leu Ser Ile Leu Leu  Phe Ser Phe
    1115                1120                1125

Phe Cys  Pro Val Arg Asn Arg  Lys Asn Lys Ala Asn
    1130                1135                1140

<210> SEQ ID NO 5
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atctgcagga attcggcacg agagtagtag actccgcacg aagaagcaaa cactgaataa      60
aggatataca ga                                                         72

<210> SEQ ID NO 6
<211> LENGTH: 223
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
caaacatata tgtaagtaag ggtatgatca tattatatca ttatgcgtat actcttatat      60
ctataatatc tatgtatcct tatactctaa ctatttatat taatttttac ttttatacaa     120
gtattaacta acccattacc agctaaaaaa aacaaacccct taacacctat ataatcccat    180
ttgcttatta cgaggctttt gttcctgcgg agtctactac taa                       223

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 7
gcggccgcgg                                                                                          10

<210> SEQ ID NO 8
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 gatct                                                                                                5

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atctgcagga attcggcacg ag                                                                            22

<210> SEQ ID NO 10
<211> LENGTH: 7913
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gggggggggg ggcgctgagg tctgcctcgt gaagaaggtg ttgctgactc ataccaggcc          60
tgaatcgccc catcatccag ccagaaagtg agggagccac ggttgatgag agctttgttg         120
taggtggacc agttggtgat tttgaacttt gctttgcca cggaacggtc tgcgttgtcg          180
ggaagatgcg tgatctgatc cttcaactca gcaaaagttc gatttattca acaaagccgc         240
cgtcccgtca gtcagcgta atgctctgcc agtgttacaa ccaattaacc aattctgatt         300
agaaaaactc atcgagcatc aaatgaaact gcaatttatt catatcagga ttatcaatac        360 catattttg aaaaagccgt ttctgtaatg aaggagaaaa ctcaccgagg cagttccata        420
ggatggcaag atcctggtat cggtctgcga ttccgactcg tccaacatca atacaaccta         480
ttaatttccc ctcgtcaaaa ataaggttat caagtgagaa atcaccatga gtgacgactg         540
aatccggtga gaatggcaaa agcttatgca tttctttcca gacttgttca acaggccagc         600
cattacgctc gtcatcaaaa tcactcgcat caaccaaacc gttattcatt cgtgattgcg         660
cctgagcgag acgaaatacg cgatcgctgt taaaaggaca attacaaaca ggaatcgaat         720
gcaaccggcg caggaacact gccagcgcat caacaatatt ttcacctgaa tcaggatatt         780
cttctaatac ctggaatgct gttttcccgg ggatcgcagt ggtgagtaac catgcatcat         840
caggagtacg gataaaatgc ttgatggtcg gaagaggcat aaattccgtc agccagttta         900
gtctgaccat ctcatctgta acatcattgg caacgctacc tttgccatgt ttcagaaaca         960
actctggcgc atcgggcttc ccatacaatc gatagattgt cgcacctgat tgcccgacat        1020
tatcgcgagc ccatttatac ccatataaat cagcatccat gttggaattt aatcgcggcc        1080
tcgagcaaga cgtttcccgt tgaatatggc tcataacacc ccttgtatta ctgtttatgt        1140

```
aagcagacag ttttattgtt catgatgata tatttttatc ttgtgcaatg taacatcaga    1200
gattttgaga cacaacgtgg ctttccccc cccccggca tgcctgcagg tcgacaatat      1260
tggctattgg ccattgcata cgttgtatct atatcataat atgtacattt atattggctc    1320
atgtccaata tgaccgccat gttgacattg attattgact agttattaat agtaatcaat    1380
tacggggtca ttagttcata gcccatatat ggagttccgc gttacataac ttacggtaaa    1440
tggcccgcct ggctgaccgc ccaacgaccc ccgcccattg acgtcaataa tgacgtatgt    1500
tcccatagta acgccaatag ggactttcca ttgacgtcaa tgggtggagt atttacggta    1560
aactgcccac ttggcagtac atcaagtgta tcatatgcca gtccgcccc ctattgacgt     1620 caatgacggt aaatggcccg cctggcatta tgcccagtac atgaccttac gggactttcc   1680
tacttggcag tacatctacg tattagtcat cgctattacc atggtgatgc ggttttggca    1740
gtacaccaat gggcgtggat agcggtttga ctcacgggga tttccaagtc tccaccccat    1800
tgacgtcaat gggagtttgt tttggcacca aaatcaacgg gactttccaa aatgtcgtaa    1860
taaccccgcc ccgttgacgc aaatgggcgg taggcgtgta cggtgggagg tctatataag    1920
cagagctcgt ttagtgaacc gtcagatcgc ctggagacgc catccacgct gttttgacct    1980
ccatagaaga caccgggacc gatccagcct ccgcggccgg gaacggtgca ttggaacgcg    2040 gattcccgt gccaagagtg acgtaagtac cgcctataga ctctataggc accccctttt    2100
ggctcttatg catgctatac tgttttttggc ttggggccta tacaccccg cttccttatg    2160 ctataggtga tggtatagct tagcctatag gtgtgggtta ttgaccatta ttgaccactc    2220
ccctattggt gacgatactt tccattacta atccataaca tggctctttg ccacaactat    2280
ctctattggc tatatgccaa tactctgtcc ttcagagact gacacggact ctgtattttt    2340
acaggatggg gtcccatttta ttatttacaa attcacatat acaacaacgc cgtcccccgt    2400
gcccgcagtt tttattaaac atagcgtggg atctccacgc gaatctcggg tacgtgttcc    2460
ggacatgggc tcttctccgg tagcggcgga gcttccacat ccgagccctg gtcccatgcc    2520
tccagcggct catggtcgct cggcagctcc ttgctcctaa cagtggaggc cagacttagg    2580
cacagcacaa tgcccaccac caccagtgtg ccgcacaagg ccgtggcggt agggtatgtg    2640
tctgaaaatg agctcggaga ttgggctcgc accgctgacg cagatggaag acttaaggca    2700
gcggcagaag aagatgcagg cagctgagtt gttgtattct gataagagtc agaggtaact    2760
cccgttgcgg tgctgttaac ggtggagggc agtgtagtct gagcagtact cgttgctgcc    2820
gcgcgcgcca ccagacataa tagctgacag actaacagac tgttcctttc catgggtctt    2880
ttctgcagtc agggtccaag cttgcggccg cggatctgca ggaattcggc acgagagtag    2940
tagactccgc acgaagaagc aaaaaattaa agaagtgagt ttaaaatgga agggtggtat    3000
ctggttgttc ttggagtctg ctatacgctg acactggcaa tgcccaagac catttatgag    3060
cttaaaatgg aatgcccgca cactgtgggt ctcggtcaag gttacatcat ggctcaaca    3120 gaactaggtt tgatctcaat tgaggctgca tctgatataa agctcgagag ctcttgcaat    3180
tttgatcttc atacaacatc tatggcccag aagagtttca cccaagttga atggagaaag   3240
aaaagtgaca caactgatac cacaaatgct gcgtccacta cctttgaagc acaaactaaa    3300
actgttaacc ttagagggac ttgtatactg gcacctgaac tctatgatac attgaagaaa    3360
gtaaaaaaga cagtcctgtg ctatgatcta acatgtaatc aaacacattg tcagccaact    3420
gtctatctga ttgcacctgt attgacatgc atgtcaataa gaagttgtat ggctagtgtg    3480
```

```
tttacaagca ggattcaggt gatttatgaa aagacacatt gtgtaacagg tcagctgatt    3540
gagggtcagt gtttcaaccc agcacacaca ttgacattat ctcagcctgc tcacacttat    3600
gatactgtca cccttcctat ctcttgtttt ttcacaccaa agaagtcgga gcaactaaaa    3660
gttataaaaa catttgaagg aattctgacg aagacaggtt gcacggagaa tgcattgcag    3720
ggttattatg tgtgtttttt agggagtcat tcagaacctt taattgttcc gagtttggag    3780
gacatacggt ctgctgaagt tgttagtagg atgcttgtac accctagggg agaagaccat    3840
gatgccatac agaattcaca aagtcactta agaatagtgg gacctatcac agcaaaagtg    3900
ccatcaacta gttccacaga taccctaaag gggacagcct ttgcaggcgt cccaatgtat    3960
agctctttat ctacactagt cagaaatgca gacccagaat ttgtattttc tccaggtata    4020
gtacctgaat ctaatcacag tacatgtgat aagaagacag tacctatcac atggacaggc    4080
tacctaccaa tatcaggtga gatggaaaaa gtgactggat gtacagtttt ttgtacacta    4140
gcaggacctg gtgctagttg tgaggcctat tctgaaaatg gtatatttaa catcagttct    4200
ccaacatgtc ttgtaaacaa agtccaagaa tttcgtggat ctgaacagaa aataaatttt    4260
atctgtcagc gggtagatca ggatgttgtt gtatactgca atgggcaaaa gaaagtcata    4320
ttaaccaaaa ctttggttat tgggcagtgt atttatacat tcacaagcct attttcattg    4380
atgcctgatg tagcccactc attggctgta gaattatgtg tcccgggatt acatgggtgg    4440
gccactgtca tgcttctatc aacattctgc tttgggtggg tcttgattcc tgcggtcaca    4500
ttaataatat taaagtgtct aagggttttg acgttttctt gttcccatta cactaatgag    4560
tcaaaattta aattcatcct ggaaaaagtt aaaattgaat accaaaagac tatgggatca    4620
atggtgtgcg atgtatgtca tcatgagtgt gaaacagcaa agaacttga atcacataga    4680
cagagttgta tcaatggaca atgtccttat tgcatgacaa taactgaagc aactgaaagt    4740
gccttgcaag cccattattc catttgtaaa ttggcaggaa gatttcagga ggcactgaaa    4800
aagtcactta aaaagccaga ggtaaaaaaa ggttgttaca gaacactcgg ggtatttaga    4860
tataaaagta gatgttatgt gggtttggta tggtgcctat tgttgacatg tgaaattgtt    4920
atttgggccg caagtgcaga gactccacta atggagtcag gctggtcaga tacggctcat    4980
ggtgttggtg agattccaat gaagacagac ctcgagctgg actttccact gccttcttca    5040
tcctcttaca gttataggag aaagctcaca aacccagcca ataaagaaga gtctattccc    5100
ttccacttcc agatggaaaa acaagtaatt catgctgaaa tccaacccct gggtcattgg    5160
atggatgcga catttaatat taagactgca tttcattgtt atggtgcatg ccagaaatac    5220
tcttatccat ggcagacatc taagtgcttc tttgaaaagg actaccagta tgaaacaggc    5280
tggggctgta atcctggtga ctgcccaggg gttgggactg gatgcactgc ttgtggtgtt    5340
tatctcgata aactaaaatc tgttgggaag gcctataaga taatttcttt aaaatatacc    5400
agaaaggttt gtattcagtt aggaacagaa caaacttgca agcatattga tgcaaatgat    5460
tgtttagtga caccatctgt gaaagtttgc ataqtgggca cagtttcaaa acttcaacca    5520
tctgatactc ttttgttctt aggtccacta gaacaagggg gaatcattct taagcaatgg    5580
tgcacaacat catgtgcatt tggggaccct ggtgatatca tgtccactcc cagtggtatg    5640
aggtgtccag agcacactgg atcatttagg aaaatttgcg gttttgctac tacaccagtt    5700
tgtgaatatc aaggaaatac catttctgga tataaaagaa tgatggcaac aaaagattca    5760
ttccaatcat ttaacttaac agaacctcac atcacaacaa acaagcttga atggatcgac    5820
ccagatggga atacaagaga ccacgtaaac cttgtcttaa atagagatgt ctcatttcag    5880
```

```
gatttaagtg ataaccoctg taaagtagac ctacacacac aagcaataga aggggcatgg   5940
ggttctggtg tagggtttac actcacatgt actgtcggat taacagagtg cccaagtttt   6000
atgacatcaa ttaaggcatg tgacctagct atgtgttatg gatcaacagt aacaaacctt   6060
gccaggggct ctaatacagt gaaagtagtt ggtaaaggag gccattcagg gtcctcattt   6120
aaatgctgtc atgatacaga ttgctcctct gaaggtttac ttgcatcagc ccctcatctt   6180
gagagggtaa caggattcaa tcaaattgat tcagataagg tttatgatga tggtgcacca   6240
ccttgcacat tcaaatgctg gttcactaag tcaggtgagt ggcttcttgg gatcttaaac   6300
gggaattgga ttgttgttgt agtgcttgtt gtgatactca ttctctctat cataatgttc   6360
agtgttttgt gtcccaggag agggcacaag aaaactgtct aagcattgac ctcaactcct   6420
acattagatc atatacattt atgcacttcc tcatatttag ctgcactaag atattaataa   6480
actctagtta ttgactttat aagattatta tggaactaac ctcacttaaa aaaaacaaat   6540
actttactca tatataactc catattctct taccgaggat tttgttcctg cggagcatac   6600
tactaggatc tacgtatgat cagcctcgac tgtgccttct agttgccagc catctgttgt   6660
ttgcccctcc cccgtgcctt ccttgaccct ggaaggtgcc actcccactg tcctttccta   6720
ataaaatgag gaaattgcat cgcattgtct gagtaggtgt cattctattc tggggggtgg   6780
ggtggggcag gacagcaagg gggaggattg gaagacaat agcaggcatg ctggggatgc   6840
ggtgggctct atggcttctg aggcggaaag aaccagctgg ggctcgacag ctcgactcta   6900
gaattgcttc ctcgctcact gactcgctgc gctcggtcgt tcggctgcgg cgagcggtat   6960
cagctcactc aaaggcggta atacggttat ccacagaatc aggggataac gcaggaaaga   7020
acatgtgagc aaaaggccag caaaaggcca ggaaccgtaa aaaggccgcg ttgctggcgt   7080
ttttccatag gctccgcccc cctgacgagc atcacaaaaa tcgacgctca agtcagaggt   7140
ggcgaaaccc gacaggacta taaagatacc aggcgtttcc ccctggaagc tccctcgtgc   7200
gctctcctgt tccgaccctg ccgcttaccg gatacctgtc cgcctttctc ccttcgggaa   7260
gcgtggcgct ttctcatagc tcacgctgta ggtatctcag ttcggtgtag gtcgttcgct   7320
ccaagctggg ctgtgtgcac gaaccccccg ttcagcccga ccgctgcgcc ttatccggta   7380
actatcgtct tgagtccaac ccggtaagac acgacttatc gccactggca gcagccactg   7440
gtaacaggat tagcagagcg aggtatgtag gcggtgctac agagttcttg aagtggtggc   7500
ctaactacgg ctacactaga agaacagtat ttggtatctg cgctctgctg aagccagtta   7560
ccttcgaaaa aagagttggt agctcttgat ccggcaaaca aaccaccgct ggtagcggtg   7620
gtttttttgt ttgcaagcag cagattacgc gcagaaaaaa aggatctcaa gaagatcctt   7680
tgatcttttc tacggggtct gacgctcagt ggaacgaaaa ctcacgttaa gggattttgg   7740
tcatgagatt atcaaaaagg atcttcacct agatcctttt aaattaaaaa tgaagtttta   7800
aatcaatcta agtatatat gagtaaactt ggtctgacag ttaccaatgc ttaatcagtg   7860
aggcacctat ctcagcgatc tgtctatttc gttcatccat agttgcctga ctc          7913
```

<210> SEQ ID NO 11
<211> LENGTH: 7924
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
ggggggggggg ggcgctgagg tctgcctcgt gaagaaggtg ttgctgactc ataccaggcc      60
tgaatcgccc catcatccag ccagaaagtg agggagccac ggttgatgag agctttgttg     120
taggtggacc agttggtgat tttgaacttt tgctttgcca cggaacggtc tgcgttgtcg     180
ggaagatgcg tgatctgatc cttcaactca gcaaaagttc gatttattca acaaagccgc     240
cgtcccgtca agtcagcgta atgctctgcc agtgttacaa ccaattaacc aattctgatt     300
agaaaaactc atcgagcatc aaatgaaact gcaatttatt catatcagga ttatcaatac     360 catattttg aaaaagccgt ttctgtaatg aaggagaaaa ctcaccgagg cagttccata      420
ggatggcaag atcctggtat cggtctgcga ttccgactcg tccaacatca atacaaccta     480
ttaatttccc ctcgtcaaaa ataaggttat caagtgagaa atcaccatga gtgacgactg     540
aatccggtga gaatggcaaa agcttatgca tttctttcca gacttgttca acaggccagc     600
cattacgctc gtcatcaaaa tcactcgcat caaccaaacc gttattcatt cgtgattgcg     660
cctgagcgag acgaaatacg cgatcgctgt taaaaggaca attacaaaca ggaatcgaat     720
gcaaccggcg caggaacact gccagcgcat caacaatatt ttcacctgaa tcaggatatt     780
cttctaatac ctggaatgct gttttcccgg ggatcgcagt ggtgagtaac catgcatcat     840
caggagtacg gataaaatgc ttgatggtcg aagaggcat aaattccgtc agccagttta      900
gtctgaccat ctcatctgta acatcattgg caacgctacc tttgccatgt ttcagaaaca     960
actctggcgc atcgggcttc ccatacaatc gatagattgt cgcacctgat tgcccgacat    1020
tatcgcgagc ccatttatac ccatataaat cagcatccat gttggaattt aatcgcggcc    1080
tcgagcaaga cgtttcccgt tgaatatggc tcataacacc ccttgtatta ctgtttatgt    1140
aagcagacag ttttattgtt catgatgata tatttttatc ttgtgcaatg taacatcaga    1200
gattttgaga cacaacgtgg ctttccccc ccccccggca tgcctgcagg tcgacaatat     1260
tggctattgg ccattgcata cgttgtatct atatcataat atgtacattt atattggctc    1320
atgtccaata tgaccgccat gttgacattg attattgact agttattaat agtaatcaat    1380 tacgggtca ttagttcata gcccatatat ggagttccgc gttacataac ttacggtaaa     1440
tggcccgcct ggctgaccgc ccaacgaccc ccgcccattg acgtcaataa tgacgtatgt    1500
tcccatagta acgccaatag ggactttcca ttgacgtcaa tgggtggagt atttacggta    1560
aactgcccac ttggcagtac atcaagtgta tcatatgcca gtccgcccc ctattgacgt     1620 caatgacggt aaatggcccg cctggcatta tgcccagtac atgaccttac gggactttcc    1680
tacttggcag tacatctacg tattagtcat cgctattacc atggtgatgc ggttttggca    1740
gtacaccaat gggcgtggat agcggtttga ctcacgggga tttccaagtc tccaccccat    1800
tgacgtcaat gggagtttgt tttggcacca aaatcaacgg gactttccaa aatgtcgtaa    1860
taaccccgcc ccgttgacgc aaatgggcgg taggcgtgta cggtgggagg tctatataag    1920
cagagctcgt ttagtgaacc gtcagatcgc ctggagacgc catccacgct gttttgacct    1980
ccatagaaga caccgggacc gatccagcct ccgcggccgg gaacggtgca ttggaacgcg    2040
gattccccgt gccaagagtg acgtaagtac cgcctataga ctctataggc acaccccttt    2100
ggctcttatg catgctatac tgttttggc ttggggccta tacaccccg cttccttatg      2160 ctataggtga tggtatagct tagcctatag gtgtgggtta ttgaccatta ttgaccactc    2220
ccctattggt gacgatactt tccattacta atccataaca tggctctttg ccacaactat    2280
ctctattggc tatatgccaa tactctgtcc ttcagagact gacacggact ctgtattttt    2340
```

```
acaggatggg gtcccattta ttatttacaa attcacatat acaacaacgc cgtccccgt    2400 gcccgcagtt tttattaaac atagcgtggg atctccacgc gaatctcggg tacgtgttcc    2460
ggacatgggc tcttctccgg tagcggcgga gcttccacat ccgagccctg gtcccatgcc    2520
tccagcggct catggtcgct cggcagctcc ttgctcctaa cagtggaggc cagacttagg    2580
cacagcacaa tgcccaccac caccagtgtg ccgcacaagg ccgtggcggt agggtatgtg    2640
tctgaaaatg agctcggaga ttgggctcgc accgctgacg cagatggaag acttaaggca    2700
gcggcagaag aagatgcagg cagctgagtt gttgtattct gataagagtc agaggtaact    2760
cccgttgcgg tgctgttaac ggtggagggc agtgtagtct gagcagtact cgttgctgcc    2820
gcgcgcgcca ccagacataa tagctgacag actaacagac tgttcctttc catgggtctt    2880
ttctgcagtc accgtccaag cttgcggccg cggatctgca ggaattcggc acgagagtag    2940
tagactccgc aagaaacagc aaacacagat aaatatgggc gagctgtccc ctgtgtgcct    3000
gtacctgctg ctgcagggcc tgctgctgtg taacaccgga gccgccagga acctgaacga    3060
gctgaagatg gagtgccccc acaccatcag actgggccag ggcctggtgg tgggcagcgt    3120
ggagctgccc agcctgccca tccagcaggt ggagaccctg aagctggaga gcagctgtaa    3180
cttcgacctg cacaccagca cagccggcca gcagagcttc accaagtgga cctgggagat    3240
caagggcgac ctggccgaga cacccaggc cagcagcacc agcttccaga ccaagagcag    3300
cgaggtgaac ctgagaggcc tgtgcctgat ccccacactg gtggtggaga ccgccgccag    3360
aatgagaaag accatcgcct gctacgacct gagctgtaac cagaccgtgt gtcagcctac    3420
cgtgtacctg atgggcccta tccagacctg tatcaccacc aagagctgcc tgctgtccct    3480
gggcgatcag agaatccagg tgaactacga gaaaacctac tgtgtgagcg ccagctggt    3540 ggagggcatc tgcttcaacc ccatccacac catggccctg agccagccta gccacaccta    3600
cgacatcatg accatgatgg tgagatgctt tctggtgatc aagaaggtga ccagcggcga    3660
cagcatgaag atcgagaaga acttcgagac cctggtgcag aagaatggct gtaccgccaa    3720
caacttccag ggctactaca tctgcctgat cggcagcagc agcgagcccc tgtacgtgcc    3780
cgccctggac gactacagaa gcgccgaggt gctgtccaga atggccttcg ccccccacgg    3840
cgaggaccac gacatcgaga aaaacgccgt gtccgccatg agaatcgccg gcaaggtgac    3900
cggcaaggcc cccagcaccg agtccagcga caccgtgcag ggcatcgcct tcagcggcag    3960 cccctgtac acctccaccg gcgtgctgac cagcaaggac gaccccgtgt acatctgggc    4020
ccctggcatc atcatggagg gcaaccacag catctgtgag aagaaaaccc tgcccctgac    4080
ctggaccggc ttcatcagcc tgcccggcga gatcgagaaa accacccagt gtaccgtgtt    4140
ctgtaccctg gccggacctg cgccgactg tgaggcctac agcgagaccg gcatcttcaa    4200
catcagcagc cccacctgcc tgatcaaccg ggtgcagagg ttcagaggca gcgagcagca    4260
gatcaagttt gtgtgccagc gggtggacat ggacatcacc gtgtactgta cggcatgaa    4320 gaaggtgatc ctgaccaaga cactggtgat cggccagtgt atctacacct tcaccagcat    4380
cttctccctg atccccggcg tggcccacag cctggccgtg gagctgtgtg tgcccggcct    4440
gcacggctgg gccaccatgc tgctgctgct gaccttctgc ttcggctggg tgctgatccc    4500
taccatcacc atgatcctgc tgaagatcct gatcgccttc gcctacctgt gctccaagta    4560
caacaccgac agcaagttca gaatcctgat cgagaaagtg aagcgggagt accagaaaac    4620
catgggcagc atggtgtgtg aagtgtgcca gtacgagtgt gagaccgcca aggagctgga    4680
gtcccacaga aagagctgct ccatcggcag ctgcccctac tgcctgaacc ccagcgaggc    4740
```

-continued

```
caccacctcc gccctgcagg cccacttcaa agtgtgtaag ctgaccagcc ggttccagga    4800
gaacctgagg aagtccctga ccgtgtacga gcccatgcag ggctgctaca gaaccctgag    4860
cctgttccgg tacaggagcc ggttctttgt gggcctggtg tggtgtgtgc tgctggtgct    4920
ggagctgatt gtgtgggccg ccagcgccga gacccagaac ctgaatgccg gctggaccga    4980
caccgcccac ggcagcggca tcatccccat gaaaaccgac ctggagctgg acttcagcct    5040
gcctagcagc gcctcctaca cctacaggcg gcagctgcag aatcctgcca acgagcagga    5100
gaagatcccc ttccacctgc agctgtccaa gcaggtgatc cacgccgaga ttcagcacct    5160
gggccactgg atggacgcca ccttcaacct gaaaaccgcc ttccactgct acggcagctg    5220
tgagaagtac gcctacccct tggcagaccg cggctgcttc atcgagaagg actacgagta    5280
cgagaccggc tggggctgta atcctcctga ttgccccgga gtgggcaccg gctgtactgc    5340
atgtggcgtg tacctggaca agctgaagtc tgtgggcaag gtgttcaaga tcgtgtccct    5400
gaggtacacc cggaaagtgt gtatccagct gggcaccgag cagacctgta agaccgtgga    5460
cagcaacgat tgcctgatca caaccagcgt gaaagtgtgt ctgatcggca ccatcagcaa    5520
gttccagccc agcgataccc tgctgttttct gggcccctg cagcagggcg gcctgatctt    5580
caagcagtgg tgtaccacca cctgccagtt cggcgatccc ggcgatatca tgagcacccc    5640
caccggcatg aagtgccctg agctgaacgg cagcttccgg aagaagtgtg ccttcgccac    5700 caccctgtg tgtcagttcg acggcaacac catcagcggc tacaagcgga tgatcgccac    5760
caaggacagc ttccagtcct tcaacgtgac cgagccccac atcagcacca gcgccctgga    5820
gtggatcgat cccgacagca gcctgaggga ccacatcaac gtgatcgtgt ccagggacct    5880
gagcttccag gacctgagcg agacccctg ccagatcgac ctggccaccg ccagcatcga    5940
tggcgcctgg ggcagcggag tgggcttcaa cctggtgtgt acagtgagcc tgaccgagtg    6000
tagcgccttc ctgaccagca tcaaaagcctg tgacgccgcc atgtgttacg gcagcaccac    6060
cgccaacctg gtgagaggcc agaacaccat ccacattgtg ggcaaaggcg ccacagcgg    6120 cagcaagttt atgtgctgcc acgacaccaa gtgtagcagc accggcctgg tggccgctgc    6180
cccccacctg gacagagtga ccggctacaa ccaggccgac agcgacaaga ttttcgacga    6240
cggagcccct gagtgtggca tgagttgctg gttcaagaag agcggcgagt ggattctggg    6300
cgtgctgaac gggaattgga tggtggtggc cgtgctggtc gtgctgctga tcctgagcat    6360
cctgctgttc accctgtgct gccctaggag acccagctac cggaaggagc acaagccctg    6420
agttttgctt actaacataa ttattgtatt ctgtttattg acacaattac catatgatta    6480
actgtattcc cccatcttat atcttatata atattcttta tttaatcact atatagaaaa    6540
aaaactagca ctttactaat taaattaccc cataccgatt atgcctggac ttttgttcct    6600
gcggagcata ctactaggat ctacgtatga tcagcctcga ctgtgccttc tagttgccag    6660
ccatctgttg tttgcccctc cccgtgcctt ccttgaccc tggaaggtgc cactcccact    6720 gtccttttcct aataaaatga ggaaattgca tcgcattgtc tgagtaggtg tcattctatt    6780
ctggggggtg gggtggggca ggacagcaag ggggaggatt gggaagacaa tagcaggcat    6840
gctggggatg cggtgggctc tatggcttct gaggcggaaa gaaccagctg ggctcgaca    6900 gctcgactct agaattgctt cctcgctcac tgactcgctg cgctcggtcg ttcggctgcg    6960
gcgagcggta tcagctcact caaaggcggt aatacggtta tccacagaat caggggataa    7020
cgcaggaaag aacatgtgag caaaaggcca gcaaaaggcc aggaaccgta aaaaggccgc    7080
```

-continued

| | |
|---|---|
| gttgctggcg ttttttccata ggctccgccc ccctgacgag catcacaaaa atcgacgctc | 7140 |
| aagtcagagg tggcgaaacc cgacaggact ataaagatac caggcgtttc ccctggaag | 7200 |
| ctccctcgtg cgctctcctg ttccgaccct gccgcttacc ggatacctgt ccgcctttct | 7260 |
| cccttcggga agcgtggcgc tttctcatag ctcacgctgt aggtatctca gttcggtgta | 7320 |
| ggtcgttcgc tccaagctgg gctgtgtgca cgaacccccc gttcagcccg accgctgcgc | 7380 |
| cttatccggt aactatcgtc ttgagtccaa cccggtaaga cacgacttat cgccactggc | 7440 |
| agcagccact ggtaacagga ttagcagagc gaggtatgta ggcggtgcta cagagttctt | 7500 |
| gaagtggtgg cctaactacg gctacactag aagaacagta tttggtatct gcgctctgct | 7560 |
| gaagccagtt accttcggaa aaagagttgg tagctcttga tccggcaaac aaaccaccgc | 7620 |
| tggtagcggt ggtttttttg tttgcaagca gcagattacg cgcagaaaaa aaggatctca | 7680 |
| agaagatcct ttgatctttt ctacggggtc tgacgctcag tggaacgaaa actcacgtta | 7740 |
| agggattttg gtcatgagat tatcaaaaag gatcttcacc tagatccttt taaattaaaa | 7800 |
| atgaagtttt aaatcaatct aaagtatata tgagtaaact tggtctgaca gttaccaatg | 7860 |
| cttaatcagt gaggcaccta tctcagcgat ctgtctattt cgttcatcca tagttgcctg | 7920 |
| actc | 7924 |

<210> SEQ ID NO 12
<211> LENGTH: 7800
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 12

| | |
|---|---|
| gggggggggg ggcgctgagg tctgcctcgt gaagaaggtg ttgctgactc ataccaggcc | 60 |
| tgaatcgccc catcatccag ccagaaaagtg agggagccac ggttgatgag agctttgttg | 120 |
| taggtggacc agttggtgat tttgaacttt tgctttgcca cggaacggtc tgcgttgtcg | 180 |
| ggaagatgcg tgatctgatc cttcaactca gcaaaagttc gatttattca acaaagccgc | 240 |
| cgtcccgtca agtcagcgta atgctctgcc agtgttacaa ccaattaacc aattctgatt | 300 |
| agaaaaactc atcgagcatc aaatgaaact gcaatttatt catatcagga ttatcaatac | 360 |
| catatttttg aaaaagccgt ttctgtaatg aaggagaaaa ctcaccgagg cagttccata | 420 |
| ggatggcaag atcctggtat cggtctgcga ttccgactcg tccaacatca atacaaccta | 480 |
| ttaatttccc ctcgtcaaaa ataaggttat caagtgagaa atcaccatga gtgacgactg | 540 |
| aatccggtga gaatggcaaa agcttatgca tttctttcca gacttgttca acaggccagc | 600 |
| cattacgctc gtcatcaaaa tcactcgcat caaccaaacc gttattcatt cgtgattgcg | 660 |
| cctgagcgag acgaaatacg cgatcgctgt taaaaggaca attacaaaca ggaatcgaat | 720 |
| gcaaccggcg caggaacact gccagcgcat caacaatatt ttcacctgaa tcaggatatt | 780 |
| cttctaatac ctggaatgct gttttcccgg ggatcgcagt ggtgagtaac catgcatcat | 840 |
| caggagtacg gataaaatgc ttgatggtcg gaagaggcat aaattccgtc agccagttta | 900 |
| gtctgaccat ctcatctgta acatcattgg caacgctacc tttgccatgt ttcagaaaca | 960 |
| actctggcgc atcgggcttc ccatacaatc gatagattgt cgcacctgat tgcccgacat | 1020 |
| tatcgcgagc ccatttatac ccatataaat cagcatccat gttggaattt aatcgcggcc | 1080 |
| tcgagcaaga cgtttcccgt tgaatatggc tcataacacc ccttgtatta ctgtttatgt | 1140 |

```
aagcagacag ttttattgtt catgatgata tattttttatc ttgtgcaatg taacatcaga    1200
gattttgaga cacaacgtgg ctttcccccc cccccggca tgcctgcagg tcgacaatat    1260
tggctattgg ccattgcata cgttgtatct atatcataat atgtacattt atattggctc    1320
atgtccaata tgaccgccat gttgacattg attattgact agttattaat agtaatcaat    1380
tacggggtca ttagttcata gcccatatat ggagttccgc gttacataac ttacggtaaa    1440
tggcccgcct ggctgaccgc ccaacgaccc ccgcccattg acgtcaataa tgacgtatgt    1500
tcccatagta acgccaatag ggactttcca ttgacgtcaa tgggtggagt atttacggta    1560
aactgcccac ttggcagtac atcaagtgta tcatatgcca agtccgcccc ctattgacgt    1620
caatgacggt aaatggcccg cctggcatta tgcccagtac atgaccttac gggactttcc    1680
tacttggcag tacatctacg tattagtcat cgctattacc atggtgatgc ggttttggca    1740
gtacaccaat gggcgtggat agcggtttga ctcacgggga tttccaagtc tccacccat    1800 tgacgtcaat gggagtttgt tttggcacca aaatcaacgg gactttccaa aatgtcgtaa    1860
taaccccgcc ccgttgacgc aaatgggcgg taggcgtgta cggtgggagg tctatataag    1920
cagagctcgt ttagtgaacc gtcagatcgc ctggagacgc catccacgct gttttgacct    1980
gcatcgaaga caccgggacc gatccagcct ccgcggccgg gaacggtgca ttggaacgcg    2040
gattccccgt gccaagagtg acgtaagtac cgcctataga ctctataggc acaccccttt    2100
ggctcttatg catgctatac tgttttggc ttggggccta taccccccg cttccttatg    2160 ctataggtga tggtatagct tagcctatag gtgtgggtta ttgaccatta ttgaccactc    2220
ccctattggt gacgatactt ccattacta atccataaca tggctctttg ccacaactat    2280
ctctattggc tatatgccaa tactctgtcc ttcagagact gacacggact ctgtattttt    2340
acaggatggg gtcccatta ttatttacaa attcacatat acaacaacgc cgtccccgt    2400 gcccgcagtt tttattaaac atagcgtggg atctccacgc gaatctcggg tacgtgttcc    2460
ggacatgggc tcttctccgg tagcggcgga gcttccacat ccgagccctg gtcccatgcc    2520
tccagcggct catggtcgct cggcagctcc ttgctcctaa cagtggaggc cagacttagg    2580
cacagcacaa tgcccaccac caccagtgtg ccgcacaagg ccgtggcggt agggtatgtg    2640
tctgaaaatg agctcggaga ttgggctcgc accgctgacg cagatggaag acttaaggca    2700
gcggcagaag aagatgcagg cagctgagtt gttgtattct gataagagtc agaggtaact    2760
cccgttgcgg tgctgttaac ggtggagggc agtgtagtct gagcagtact cgttgctgcc    2820
gcgcgcgcca ccagacataa tagctgacag actaacagac tgttcctttc catgggtctt    2880
ttctgcagtc accgtccaag cttgcggccg cggatctgca ggaattcggc acgagagtag    2940
tagactccgc aagaaacagc agtcaatcag caacatgggg atatggaagt ggctagtgat    3000
ggccagttta gtatggcctg ttttgacact gagaaatgtc tatgacatga aaattgagtg    3060
cccccataca gtaagttttg gggaaaacag tgtgataggt tatgtagaat taccccccgt    3120
gccattggcc gacacagcac agatggtgcc tgagagttct tgtagcatgg ataatcacca    3180
atcgttgaat acaataacaa aatatcccca agtaagttgg agaggaaagg ctgatcagtc    3240
acagtctagt caaaattcat ttgagacagt gtccactgaa gttgacttga aggaacatg    3300 tgctctaaaa cacaaaatgg tggaagaatc ataccgtagt aggaaatcag taacctgtta    3360
cgacctgtct tgcaatagca cttactgcaa gccaacacta tacatgattg taccaattca    3420
tgcatgcaat atgatgaaaa gctgtttgat tgcattggga ccatacagag tacaggtggt    3480
ttatgagaga tcttattgca tgacaggagt cctgattgaa gggaaatgct tgtcccaga    3540
```

```
tcaaagtgtg gtcagtatta tcaagcatgg gatctttgat attgcaagtg ttcatattgt    3600
atgtttcttt gttgcagtta aagggaatac ttataaaatt tttgaacagg ttaagaaatc    3660
ctttgaatca acatgcaatg atacagagaa taaagtgcaa ggatattata tttgtattgt    3720 aggggggaaac tctgcaccaa tatatgttcc aacacttgat gatttcagat ccatggaagc    3780
atttacagga atcttcagat caccacatgg ggaagatcat gatctggctg gagaagaaat    3840
tgcatcttat tctatagtcg gacctgccaa tgcaaaagtt cctcatagtg ctagctcaga    3900
tacattgagc ttgattgcct attcaggtat accatcttat tcttccctta gcatcctaac    3960
aagttcaaca gaagctaagc atgtattcag ccctgggttg ttcccaaaac ttaatcacac    4020
aaattgtgat aaaagtgcca taccactcat atggactggg atgattgatt tacctggata    4080
ctacgaagct gtccacccct tgtacagtttt ttgcgtatta tcaggtcctg ggcatcatg    4140 tgaagccttt tctgaaggcg ggattttcaa cataacctct cccatgtgct tagtgtcaaa    4200
acaaaatcga ttccggttaa cagaacagca agtgaatttt gtgtgtcagc gagtggacat    4260
ggacattgtt gtgtactgca acgggcagag gaaagtaata ttaacaaaaa ctctagttat    4320
tggacagtgt atatatacta taacaagctt attctcatta ctacctggag tagcacattc    4380
tattgctgtt gaattgtgtg tacctgggtt ccatggttgg gccacagctg ctctgcttgt    4440
tacattctgt ttcggatggg ttcttatacc agcaattaca tttatcatac taacagtcct    4500
aaagttcatt gctaatattt ttcacacaag taatcaagag aataggctaa aatcagtact    4560
tagaaagata aaggaagagt ttgaaaaaac aaaaggctca atggtatgtg atgtctgcaa    4620
gtatgagtgt gaaacctata aagaattaaa ggcacacggg gtatcatgcc cccaatctca    4680
atgtccttac tgttttactc attgtgaacc cacagaagca gcattccaag ctcattacaa    4740
ggtatgccaa gttactcaca gattcaggga tgatctaaag aaaactgtta ctcctcaaaa    4800
ttttacacca ggatgttacc ggacactaaa tttatttaga tacaaaagca ggtgctacat    4860
ctttacaatg tggatatttc ttcttgtctt agaatccata ctgtgggctg caagtgcatc    4920
agagacacca ttaactcctg tctgaatga caatgcccat ggggtaggtt ctgttcctat    4980
gcatacagat ttagagcttg atttctcttt aacatccagt tccaagtata cataccgtag    5040
gaggttaaca aacccacttg aggaagcaca atccattgac ctacatattg aaatagaaga    5100
acagacaatt ggtgttgatg tgcatgctct aggacactgg tttgatggtc gtcttaacct    5160
taaaacatcc tttcactgtt atggtgcttg tacaaagtat gaataccctt ggcatactgc    5220
aaagtgccac tatgaaagag attaccaata tgagacgagc tggggttgta atccatcaga    5280
ttgtcctggg gtgggcacag gctgtacagc atgtggttta acctagatc aactgaaacc    5340 agttggtagt gcttataaaa ttatcacaat aaggtacagc aggagagtct gtgttcagtt    5400
tggggaggaa aaccttttgta agataataga catgaatgat tgtttttgtat ctaggcatgt    5460 taaggtctgc ataattggta cagtatctaa attctctcag ggtgatacct tattgttttt    5520
tggaccgctt gaaggtggtg gtctaatatt taaacactgg tgtacatcca catgtcaatt    5580
tggtgaccca ggagatatca tgagtccaag agacaaaggt tttttatgcc ctgagttttcc    5640 aggtagtttc aggaagaaat gcaactttgc tactaccccct atttgtgagt atgatggaaa    5700
tatggtctca ggttacaaga aagtgatggc cacaattgat tccttccaat ctttttaatac    5760 aagcactatg cacttcactg atgaaaggat agagtggaaa gaccctgatg gaatgctaag    5820
ggaccatata aacatttttag taacgaagga cattgacttt gataaccttg gtgaaaatcc    5880
```

```
ttgcaaaatt ggcctacaaa catcttctat tgagggggcc tggggttctg gtgtggggtt      5940
cacattaaca tgtctggtat cactaacaga atgtcctacc tttttgacct caataaaggc      6000
ttgtgataag gctatctgtt atggtgcaga gagtgtaaca ttgacaagag gacaaaatac      6060
agtcaaggta tcagggaaag gtggccatag tggttcaaca tttaggtgtt gccatgggga      6120
ggactgttca caaattggac tccatgctgc tgcacctcac cttgacaagg taaatgggat      6180
ttctgagata gaaaatagta aagtatatga tgatggggca ccgcaatgtg ggataaaatg      6240
ttggtttgtt aaatcagggg aatggatttc agggatattc agtggtaatt ggattgtact      6300
cattgtcctc tgtgtatttc tattgttctc cttggtttta ctaagcattc tctgtcccgt      6360
aaggaagcat aaaaaatcat agctaaattc tgtgactatc ctgttcttat gtatagcttt      6420
aacatatata ctaattttta tattccagta tactctatct aacacactaa aaaaaatagt      6480
agctttctaa ccacaaaacg gatctacgta tgatcagcct cgactgtgcc ttctagttgc      6540
cagccatctg ttgtttgccc ctcccccgtg ccttccttga ccctggaagg tgccactccc      6600
actgtccttt cctaataaaa tgaggaaatt gcatcgcatt gtctgagtag gtgtcattct      6660
attctggggg gtggggtggg gcaggacagc aaggggggagg attgggaaga caatagcagg      6720
catgctgggg atgcggtggg ctctatggct tctgaggcgg aaagaaccag ctggggctcg      6780
acagctcgac tctagaattg cttcctcgct cactgactcg ctgcgctcgg tcgttcggct      6840
gcggcgagcg gtatcagctc actcaaaggc ggtaatacgg ttatccacag aatcaggggga      6900
taacgcagga aagaacatgt gagcaaaagg ccagcaaaag gccaggaacc gtaaaaaggc      6960
cgcgttgctg gcgtttttcc ataggctccg ccccccctgac gagcatcaca aaaatcgacg      7020
ctcaagtcag aggtggcgaa acccgacagg actataaaga taccaggcgt ttccccctgg      7080
aagctccctc gtgcgctctc ctgttccgac cctgccgctt accggatacc tgtccgcctt      7140
tctcccttcg ggaagcgtgg cgctttctca tagctcacgc tgtaggtatc tcagttcggt      7200
gtaggtcgtt cgctccaagc tgggctgtgt gcacgaaccc cccgttcagc ccgaccgctg      7260
cgccttatcc ggtaactatc gtcttgagtc caacccggta agacacgact tatcgccact      7320
ggcagcagcc actggtaaca ggattagcag agcgaggtat gtaggcggtg ctacagagtt      7380
cttgaagtgg tggcctaact acggctacac tagaagaaca gtatttggta tctgcgctct      7440
gctgaagcca gttaccttcg gaaaaagagt tggtagctct tgatccggca acaaaccac      7500
cgctggtagc ggtggttttt tgtttgcaa gcagcagatt acgcgcagaa aaaaggatc      7560
tcaagaagat cctttgatct tttctacggg gtctgacgct cagtggaacg aaaactcacg      7620
ttaagggatt ttggtcatga gattatcaaa aaggatcttc acctagatcc ttttaaatta      7680
aaaatgaagt tttaaatcaa tctaaagtat atatgagtaa acttggtctg acagttacca      7740
atgcttaatc agtgaggcac ctatctcagc gatctgtcta tttcgttcat ccatagttgc      7800
```

<210> SEQ ID NO 13
<211> LENGTH: 8001
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
gggggggggg ggcgctgagg tctgcctcgt gaagaaggtg ttgctgactc ataccaggcc        60
tgaatcgccc catcatccag ccagaaagtg agggagccac ggttgatgag agctttgttg       120
```

```
taggtggacc agttggtgat tttgaacttt tgctttgcca cggaacggtc tgcgttgtcg    180
ggaagatgcg tgatctgatc cttcaactca gcaaaagttc gatttattca acaaagccga    240
cgtcccgtca agtcagcgta atgctctgcc agtgttacaa ccaattaacc aattctgatt    300
agaaaaactc atcgagcatc aaatgaaact gcaatttatt catatcagga ttatcaatac    360
catattttg  aaaaagccgt tctgtaatg  aaggagaaaa ctcaccgagg cagttccata    420
ggatggcaag atcctggtat cggtctgcga ttccgactcg tccaacatca atacaaccta    480
ttaatttccc ctcgtcaaaa ataaggttat caagtgagaa atcaccatga gtgacgactg    540
aatccggtga gaatggcaaa agcttatgca tttctttcca gacttgttca acaggccagc    600
cattacgctc gtcatcaaaa tcactcgcat caaccaaacc gttattcatt cgtgattgcg    660
cctgagcgag acgaaatacg cgatcgctgt taaaaggaca attacaaaca ggaatcgaat    720
gcaaccggcg caggaacact gccagcgcat caacaatatt tcacctgaa  tcaggatatt    780
cttctaatac ctggaatgct gttttcccgg ggatcgcagt ggtgagtaac catgcatcat    840
caggagtacg gataaaatgc ttgatggtcg aagaggcat  aaattccgtc agccagttta    900
gtctgaccat ctcatctgta acatcattgg caacgctacc tttgccatgt tcagaaaca    960
actctggcgc atcgggcttc ccatacaatc gatagattgt cgcacctgat tgccccacat    1020
tatcgcgagc ccatttatac ccatataaat cagcatccat gttggaattt aatcgcggcc    1080
tcgagcaaga cgtttcccgt tgaatatggc tcataacacc ccttgtatta ctgtttatgt    1140
aagcagacag ttttattgtt catgatgata tatttttatc ttgtgcaatg taacatcaga    1200
gattttgaga cacaacgtgg ctttccccc  cccccggca  tgcctgcagg tcgacataaa    1260
tcaatattgg ctattggcca ttgcatacgt tgtatctata tcataatatg tacatttata    1320
ttggctcatg tccaatatga ccgccatgtt gacattgatt attgactagt tattaatagt    1380
aatcaattac ggggtcatta gttcatagcc catatatgga gttccgcgtt acataactta    1440
cggtaaatgg cccgcctcgt gaccgcccaa cgacccccgc ccattgacgt caataatgac    1500
gtatgttccc atagtaacgc caatagggac tttccattga cgtcaatggg tggagtattt    1560
acggtaaact gccccacttgg cagtacatca agtgtatcat atgccaagtc cggcccccta    1620
tgacgtcaa  tgacggtaaa tggcccgcct ggcattatgc ccagtacatg accttacggg    1680
actttcctac ttggcagtac atctacgtat tagtcatcgc tattaccatg gtgatgcggt    1740
tttggcagta caccaatggg cgtggatagc ggtttgactc acggggattt ccaagtctcc    1800
accccattga cgtcaatggg agtttgtttt ggcaccaaaa tcaacgggac tttccaaaat    1860
gtcgtaataa ccccgccccg ttgacgcaaa tgggcggtag cgtgtacgg  tgggaggtct    1920
atataagcag agctcgttta gtgaaccgtc agatcgcctg gagacgccat ccacgctgtt    1980
ttgacctcca tagaagacac cgggaccgat ccagcctccg cggccgggaa cggtgcattg    2040
gaacgcggat tccccgtgcc aagagtgacg taagtaccgc ctatagactc tataggcaca    2100
cccctttggc tcttatgcat gctatactgt ttttggcttg ggcctatac  accccgctc     2160
cttatgctat aggtgatggt atagcttagc ctataggtgt gggttattga ccattattga    2220
ccactcccct attggtgacg atactttcca ttactaatcc ataacatggc tctttgccac    2280
aactatctct attggctata tgccaatact ctgtccttca gagactgaca cggactctgt    2340
atttttacag gatggggtcc catttattat ttacaaattc acatatacaa caacgccgtc    2400
cccgtgccc  gcagttttta ttaaacatag cgtgggatct ccacgcgaat ctcgggtacg    2460
tgttccggac atgggctctt ctccggtagc ggcggagctt ccacatccga gccctggtcc    2520
```

```
catgcctcca gcggctcatg gtcgctcggc agctccttgc tcctaacagt ggaggccaga    2580
cttaggcaca gcacaatgcc caccaccacc agtgtgccgc acaaggccgt ggcggtaggg    2640
tatgtgtctg aaaatgagct cggagattgg gctcgcaccg tgacgcagat ggaagactta    2700
aggcagcggc agaagaagat gcaggcagct gagttgttgt attctgataa gagtcagagg    2760
taactcccgt tgcggtgctg ttaacggtgg agggcagtgt agtctgagca gtactcgttg    2820
ctgccgcgcg cgccaccaga cataatagct gacagactaa cagactgttc ctttccatgg    2880
gtcttttctg cagtcaccgt ccaagcttgc ggccgcggat ctgcaggaat cggcacgag    2940
agtagtagac tccgcaagaa acagcagtta aagaacaata ggatcatgtg gagtttgcta    3000
ttactggccg ctttagttgg ccaaggcttt gcattaaaaa atgtatttga catgagaatt    3060
cagttgcccc actcagtcaa ctttggggaa acaagtgtgt caggctatac agaatttccc    3120
ccactctcat tacaggaggc agaacagcta gtgccagaga gctcatgcaa catggacaac    3180
caccagtcac tctcaacaat aaataaatta accaaggtca tatggcggaa aaaagcaaat    3240
caggaatcag caaaccagaa ttcatttgaa gttgtggaaa gtgaagtcag ctttaaaggg    3300
ttgtgtatgt taaagcatag aatggttgaa gaatcatata gaataggag atcagtaatc    3360
tgttatgatc tagcctgtaa tagtacattc tgtaaaccaa ctgtttatat gattgttcct    3420
atacatgctt gcaacatgat gaaaagctgt tgattggcc ttggccccta cagaatccag    3480
gttgtctatg aaaggacata ctgcactacg ggtatattga cagaaggaaa atgctttgtc    3540
cctgacaagg ctgttgtcag tgcattgaaa agaggcatgt atgctatagc aagcatagag    3600
acaatctgct ttttattca tcagaaaggg aatacatata agatagtgac tgccattaca    3660
tcagcaatgg gctccaaatg taataataca gatactaaag ttcaaggata ttatatctgt    3720
attattggtg gaaactccgc ccctgtatat gcccctgctg gtgaagactt cagagcaatg    3780
gaggttttt ctgggattat tacatcacca catggagaag accatgaccct acccggcgaa    3840
gaaatcgcaa cgtaccagat ttcagggcag atagaggcaa aaatccctca tacagtgagc    3900
tccaaaaact taaaattgac tgcttttgca ggtattccat catactcatc aactagtata    3960
ttggctgctt cagaagatgg tcgtttcata tttagtcctg gtttatttcc taacctaaat    4020
cagtcagtct gtgacaacaa tgcactccct ttaatctgga ggggcctaat tgatttaacg    4080
ggatactatg aggcagtcca cccttgcaat gtgttctgtg tcttatcagg accaggtgct    4140
tcatgtgagg ccttttcaga aggaggtatt ttcaatatta cttctccaat gtgtctggtg    4200
tctaagcaaa atagatttag agcagctgag cagcagatta gctttgtctg ccaaagagtt    4260
gatatggata ttatagtgta ctgtaatggt cagaaaaaaa caatcctaac aaaaacatta    4320
gttataggcc aatgtattta tactattaca agtctctttt cactgttacc aggggttgcc    4380
cattctattg ctattgagtt gtgtgttcca gggtttcatg gctgggccac agctgcactt    4440
ttgattacat tctgcttcgg ctgggtattg attcctgcat gtacattagc tattctttta    4500
gtccttaagt tctttgcaaa tatccttcat acaagcaatc aagagaaccg attcaaagcc    4560
attctacgga aaataaagga ggagtttgaa aaaacaaagg gttccatggt ttgtgagatc    4620
tgtaagtatg agtgtgaaac attaaaggaa ttgaaggcac ataacctatc atgtgttcaa    4680
ggagagtgcc catattgctt tacccactgt gaaccgacag aaactgcaat tcaggcacat    4740
tacaaagttt gtcaagccac ccaccgattc agagaagatt taaaaagac tgtaactcct    4800
caaaatattg ggccaggctg ttaccgaaca ctaaatcttt ttaggtataa aagtaggtgt    4860
```

```
tatattctga caatgtggac tcttcttctc attattgaat ccatcctctg gcagcaagt    4920 gcagcagaaa tccccccttgt ccctctctgg acagataatg ctcatggcgt tgggagtgtt    4980
cctatgcata cggatcttga attagacttc tctttgccat ccagttctaa gtacacatac    5040
aaaagacatc tcacaaaccc agttaatgac aacagagtg tctcattgca tatagaaatt    5100
gaaagtcaag gcattggtgc tgctgttcat catcttggac attggtatga tgcaagattg    5160
aatctaaaaa cctcatttca ttgttatggt gcctgcacaa atatcaata cccatggcac    5220 actgcaaaat gccattttga gaaagattat gagtatgaaa atagctgggc ttgcaacccc    5280
ccagattgcc caggggttgg tacaggttgt actgcttgtg gattatatct agatcaattg    5340
aagccggtag gaacagcctt taaaattata agtgtaagat acagtagaaa agtgtgcgtg    5400
cagtttggtg aagaacacct ttgtaaaaca attgatatga atgattgctt tgtgactagg    5460
catgccaaaa tatgtataat tgggactgta tctaagtttt ctcaaggtga cactctacta    5520
tttctggggc ccatggaagg aggtggtata atctttaaac actggtgtac atctacctgt    5580
cactttggag accctggtga tgtcatgggt ccaaaagata aaccatttat ttgccctgaa    5640
ttcccagggc aatttaggaa aaaatgtaac tttgccacaa ctccagtttg tgaatatgat    5700
ggaaacatta tatcaggcta taagaaagta cttgcaacaa ttgattcttt ccaatcattt    5760
aacacaagca atatacactt cactgatgag agaattgaat ggagagaccc tgatggcatg    5820
cttcgggatc atattaatat tgttatttct aaagatattg attttgaaaa tttggctgag    5880
aatccttgta agtagggct ccaggcagca acatagaag gtgcctgggg ttcaggtgtc    5940
gggtttacac tcacatgcaa ggtgtctctc acagaatgcc caacatttct tacatcaata    6000
aaggcctgtg acatggcaat ttgttatggt gcagaaagtg tgacactctc acgaggacaa    6060
aatactgtca aaattaccgg gaaggtggc catagtggtt cttcattcaa atgctgtcat    6120
gggaaagaat gttcatcaac tggcctccaa gccagtgcac cacatctgga taaggtaaat    6180
ggtatctctg agttagaaaa cgagaaagtt tatgatgacg gtgcacctga atgtggcatt    6240
acttgttggt ttaaaaaatc aggtgaatgg gttatgggta taatcaatgg gaactgggtt    6300
gtcctaattg tcttgtgtgt actgctgctc ttttctctta tcctgttgag catcttgtgt    6360
cctgttagaa agcataaaaa atcataaatc ccacctaaca atcttcacat catgtatcga    6420
ttttcaaaca ctttatcatt tagaacttaa cttggcacta ctatctgata actgactttc    6480
attttatttt ttatatggat taattactaa aaaaaatact ctctcgtgcc gaattcgata    6540
tcaagcttat cgataccgtc gacctcgagg ggggcccgg tacccgggat cctcgcaatc    6600
cctaggagga ttaggcaagg gcttgagctc acgctcttgt gagggacaga aatacaatca    6660
ggggcagtat atgaatactc catggagaaa cccagatcta cgtatgatca gcctcgactg    6720
tgccttctag ttgccagcca tctgttgttt gcccctcccc cgtgccttcc ttgaccctgg    6780
aaggtgccac tcccactgtc ctttcctaat aaaatgagga aattgcatcg cattgtctga    6840
gtaggtgtca ttctattctg ggggggtgggg tgggcagga cagcaagggg gaggattggg    6900
aagacaatag caggcatgct ggggatgcgg tgggctctat ggcttctgag gcggaaagaa    6960
ccagctgggg ctcgacagct cgactctaga attgcttcct cgctcactga ctcgctgcgc    7020
tcggtcgttc ggctgcggcg agcggtatca gctcactcaa aggcggtaat acggttatcc    7080
acagaatcag gggataacgc aggaaagaac atgtgagcaa aaggccagca aaaggccagg    7140
aaccgtaaaa aggccgcgtt gctggcgttt ttccataggc tccgcccccc tgacgagcat    7200
cacaaaaatc gacgctcaag tcagaggtgg cgaaacccga caggactata agataccag    7260
```

```
gcgtttcccc ctggaagctc cctcgtgcgc tctcctgttc cgaccctgcc gcttaccgga    7320
tacctgtccg ccttttctccc ttcgggaagc gtggcgcttt ctcaatgctc acgctgtagg    7380
tatctcagtt cggtgtaggt cgttcgctcc aagctgggct gtgtgcacga accccccgtt    7440
cagcccgacc gctgcgcctt atccggtaac tatcgtcttg agtccaaccc ggtaagacac    7500
gacttatcgc cactggcagc agccactggt aacaggatta gcagagcgag gtatgtaggc    7560
ggtgctacag agttcttgaa gtggtggcct aactacggct acactagaag gacagtattt    7620
ggtatctgcg ctctgctgaa gccagttacc ttcggaaaaa gagttggtag ctcttgatcc    7680
ggcaaacaaa ccaccgctgg tagcggtggt ttttttgttt gcaagcagca gattacgcgc    7740
agaaaaaaag gatctcaaga agatcctttg atcttttcta cggggtctga cgctcagtgg    7800
aacgaaaact cacgttaagg gattttggtc atcagattat caaaaaggat cttcacctag    7860
atccttttaa attaaaaatg aagttttaaa tcaatctaaa gtatatatga gtaaacttgg    7920
tctgacagtt accaatgctt aatcagtgag gcacctatct cagcgatctg tctatttcgt    7980
tcatccatag ttgcctgact c                                              8001

<210> SEQ ID NO 14
<211> LENGTH: 3447
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgggcgagc tgtcccctgt gtgcctgtac ctgctgctgc agggcctgct gctgtgtaac      60
accggagccg ccaggaacct gaacgagctg aagatggagt gccccacac catcagactg     120 ggccagggcc tggtggtggg cagcgtggag ctgcccagcc tgcccatcca gcaggtggag     180
accctgaagc tggagagcag ctgtaacttc gacctgcaca ccagcacagc cggccagcag     240
agcttcacca gtggacctg ggagatcaag ggcgacctgg ccgagaacac ccaggccagc     300
agcaccagct ccagaccaa gagcagcgag gtgaacctga gaggcctgtg cctgatcccc     360
acactggtgg tggagaccgc ccgccagaatg agaaagacca tcgcctgcta cgacctgagc     420
tgtaaccaga ccgtgtgtca gcctaccgtg tacctgatgg gccctatcca gacctgtatc     480
accaccaaga gctgcctgct gtccctgggc gatcagagaa tccaggtgaa ctacgagaaa     540
acctactgtg tgagcggcca gctggtggag ggcatctgct tcaaccccat ccacaccatg     600
gccctgagcc agcctagcca cacctacgac atcatgacca tgatggtgag atgctttctg     660
gtgatcaaga aggtgaccag cggcgacagc atgaagatcg agaagaactt cgagaccctg     720
gtgcagaaga atggctgtac cgccaacaac ttccagggct actacatctg cctgatcggc     780
agcagcagcg agcccctgta cgtgcccgcc ctggacgact acagaagcgc cgaggtgctg     840
tccagaatgg ccttcgcccc ccacggcgag gaccacgaca tcgagaaaaa cgccgtgtcc     900
gccatgagaa tcgccggcaa ggtgaccggc aaggccccca gcaccgagtc cagcgacacc     960
gtgcagggca tcgccttcag cggcagcccc ctgtacacct ccaccggcgt gctgaccagc    1020
aaggacgacc ccgtgtacat ctgggcccct ggcatcatca tggagggcaa ccacagcatc    1080
tgtgagaaga aaaccctgcc cctgacctgg accggcttca tcagcctgcc ggcgagatc    1140 gagaaaacca cccagtgtac cgtgttctgt accctggccg acctggcgc cgactgtgag    1200 gcctacagcg agaccggcat cttcaacatc agcagcccca cctgcctgat caaccgggtg    1260
```

```
cagagggttca gaggcagcga gcagcagatc aagtttgtgt gccagcgggt ggacatggac   1320
atcaccgtgt actgtaacgg catgaagaag gtgatcctga ccaagacact ggtgatcggc   1380
cagtgtatct acaccttcac cagcatcttc tccctgatcc ccggcgtggc ccacagcctg   1440
gccgtggagc tgtgtgtgcc cggcctgcac ggctgggcca ccatgctgct gctgctgacc   1500
ttctgcttcg gctgggtgct gatccctacc atcaccatga tcctgctgaa gatcctgatc   1560
gccttcgcct acctgtgctc caagtacaac accgacagca gttcagaat cctgatcgag   1620
aaagtgaagc gggagtacca gaaaaccatg ggcagcatgg tgtgtgaagt gtgccagtac   1680
gagtgtgaga ccgccaagga gctggagtcc cacagaaaga gctgctccat cggcagctgc   1740
ccctactgcc tgaaccccag cgaggccacc acctccgccc tgcaggccca cttcaaagtg   1800
tgtaagctga ccagccggtt ccaggagaac ctgaggaagt ccctgaccgt gtacgagccc   1860
atgcagggct gctacagaac cctgagcctg ttccggtaca ggagccggtt ctttgtgggc   1920
ctggtgtggt gtgtgctgct ggtgctggag ctgattgtgt gggccgccag cgccgagacc   1980
cagaacctga atgccggctg gaccgacacc gcccacggca gcggcatcat ccccatgaaa   2040
accgacctgg agctggactt cagcctgcct agcagcgcct cctacaccta caggcggcag   2100
ctgcagaatc ctgccaacga gcaggagaag atccccttcc acctgcagct gtccaagcag   2160
gtgatccacg ccgagattca gcacctgggc cactggatgg acgccacctt caacctgaaa   2220
accgccttcc actgctacgg cagctgtgag aagtacgcct acccttggca gaccgccggc   2280
tgcttcatcg agaaggacta cgagtacgag accggctggg gctgtaatcc tcctgattgc   2340
cccggagtgg gcaccggctg tactgcatgt ggcgtgtacc tggacaagct gaagtctgtg   2400
ggcaaggtgt tcaagatcgt gtccctgagg tacacccgga agtgtgtat ccagctgggc   2460
accgagcaga cctgtaagac cgtggacagc aacgattgcc tgatcacaac cagcgtgaaa   2520
gtgtgtctga tcggcaccat cagcaagttc cagcccagcg ataccctgct gtttctgggc   2580
cccctgcagc agggcggcct gatcttcaag cagtggtgta ccaccacctg ccagttcggc   2640
gatcccggcg atatcatgag caccccacc ggcatgaagt gccctgagct gaacggcagc   2700
ttccggaaga agtgtgcctt cgccaccacc cctgtgtgtc agttcgacgg caacaccatc   2760
agcggctaca gcggatgat cgccaccaag gacagcttcc agtccttcaa cgtgaccgag   2820
ccccacatca gcaccagcgc cctggagtgg atcgatcccg acagcagcct gagggaccac   2880
atcaacgtga tcgtgtccag ggacctgagc ttccaggacc tgagcgagac cccctgccag   2940
atcgacctgg ccaccgccag catcgatggc gcctggggca cggagtggg cttcaacctg   3000
gtgtgtacag tgagcctgac cgagtgtagc gccttcctga ccagcatcaa gcctgtgac   3060
gccgccatgt gttacggcag caccaccgcc aacctggtga gaggcagaa caccatccac   3120
attgtgggca aggcggcca cagcggcagc aagtttatgt gctgccacga caccaagtgt   3180
agcagcaccg gcctggtggc cgctgccccc cacctggaca gagtgaccgg ctacaaccag   3240
gccgacagcg acaagatttt cgacgacgga gcccctgagt gtggcatgag ttgctggttc   3300
aagaagagcg gcgagtggat tctgggcgtg ctgaacggga attggatggt ggtggccgtg   3360
ctggtcgtgc tgctgatcct gagcatcctg ctgttcaccc tgtgctgccc taggagaccc   3420
agctaccgga aggagcacaa gccctga                                      3447
```

<210> SEQ ID NO 15
<211> LENGTH: 1140
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 15

```
Met Val Gly Trp Val Cys Ile Phe Leu Val Val Leu Thr Thr Ala Thr
1               5                   10                  15

Ala Gly Leu Thr Arg Asn Leu Tyr Glu Leu Gln Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Gln Lys Tyr Asn Gln
65                  70                  75                  80

Val Asp Trp Thr Lys Lys Ser Ser Thr Glu Ser Thr Asn Ala Gly
                85                  90                  95

Ala Thr Thr Phe Glu Ala Lys Thr Lys Glu Val Asn Leu Lys Gly Thr
            100                 105                 110

Cys Asn Ile Pro Pro Thr Thr Phe Glu Ala Ala Tyr Lys Ser Arg Lys
            115                 120                 125

Thr Val Ile Cys Tyr Asp Leu Ala Cys Asn Gln Thr His Cys Leu Pro
        130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240

Ala Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Val Thr Ala
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
            340                 345                 350

Ser Val Cys Asp Lys Lys Thr Val Pro Leu Thr Trp Thr Gly Phe Leu
        355                 360                 365

Ala Val Ser Gly Glu Ile Glu Arg Ile Thr Gly Cys Thr Val Phe Cys
    370                 375                 380
```

```
Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Gly Val Val Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Val Thr Leu Ile Ile Leu Lys Ile
            500                 505                 510

Leu Arg Leu Leu Thr Phe Pro Cys Ser His Tyr Ser Thr Glu Ser Lys
        515                 520                 525

Phe Lys Val Ile Leu Glu Arg Val Lys Val Glu Tyr Gln Lys Thr Met
    530                 535                 540

Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Ile Thr Glu Ser Thr Glu Ser Ala Leu Gln Ala His Phe
            580                 585                 590

Ser Ile Cys Lys Leu Thr Asn Arg Phe Gln Glu Asn Leu Lys Lys Ser
        595                 600                 605

Leu Lys Arg Pro Glu Val Arg Lys Gly Cys Tyr Arg Thr Leu Gly Val
    610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Gln Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
```

```
                        805                 810                 815
Gln Thr Cys Lys His Ile Asp Val Asn Asp Cys Leu Val Thr Pro Ser
            820                 825                 830

Val Lys Val Cys Met Ile Gly Thr Ile Ser Lys Leu Gln Pro Gly Asp
            835                 840                 845

Thr Leu Leu Phe Leu Gly Pro Leu Glu Gln Gly Gly Ile Ile Leu Lys
            850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
                900                 905                 910

Thr Val Ser Gly Phe Gln Arg Met Met Ala Thr Arg Asp Ser Phe Gln
            915                 920                 925

Ser Phe Asn Val Thr Glu Pro His Ile Thr Ser Asn Arg Leu Glu Trp
            930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu Thr Glu Cys Ala Asn Phe Ile Thr
            995                 1000                1005

Ser Ile Lys Ala Cys Asp Ser Ala Met Cys Tyr Gly Ala Thr Val
            1010                1015                1020

Thr Asn Leu Leu Arg Gly Ser Asn Thr Val Lys Val Val Gly Lys
            1025                1030                1035

Gly Gly His Ser Gly Ser Leu Phe Lys Cys Cys His Asp Thr Asp
            1040                1045                1050

Cys Thr Glu Glu Gly Leu Ala Ala Ser Pro Pro His Leu Asp Arg
            1055                1060                1065

Val Thr Gly Tyr Asn Gln Ile Asp Ser Asp Lys Val Tyr Asp Asp
            1070                1075                1080

Gly Ala Pro Pro Cys Thr Ile Lys Cys Trp Phe Thr Lys Ser Gly
            1085                1090                1095

Glu Trp Leu Leu Gly Ile Leu Asn Gly Asn Trp Val Val Val Ala
            1100                1105                1110

Val Leu Ile Val Ile Leu Ile Leu Ser Ile Leu Leu Phe Ser Phe
            1115                1120                1125

Phe Cys Pro Val Arg Asn Arg Lys Asn Lys Ala Asn
            1130                1135                1140

<210> SEQ ID NO 16
<211> LENGTH: 1140
<212> TYPE: PRT
<213> ORGANISM: Sin Nombre virus
<220> FEATURE:
<223> OTHER INFORMATION: strain Convict Creek 107

<400> SEQUENCE: 16

Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
```

```
                      20                  25                  30
Thr Val Gly Leu Gly Gln Gly Tyr Val Thr Gly Ser Val Glu Thr Thr
             35                  40                  45
Pro Ile Leu Leu Thr Gln Val Ala Asp Leu Lys Ile Glu Ser Ser Cys
     50                  55                  60
Asn Phe Asp Leu His Val Pro Ala Thr Thr Gln Lys Tyr Asn Gln
65                  70                  75                  80
Val Asp Trp Thr Lys Lys Ser Ser Thr Glu Ser Thr Asn Ala Gly
                 85                  90                  95
Ala Thr Thr Phe Glu Ala Lys Thr Lys Glu Val Asn Leu Lys Gly Thr
            100                 105                 110
Cys Asn Ile Pro Pro Thr Thr Phe Glu Ala Ala Tyr Lys Ser Arg Lys
            115                 120                 125
Thr Val Ile Cys Tyr Asp Leu Ala Cys Asn Gln Thr His Cys Leu Pro
            130                 135                 140
Thr Val His Leu Ile Ala Pro Val Gln Thr Cys Met Ser Val Arg Ser
145                 150                 155                 160
Cys Met Ile Gly Leu Leu Ser Ser Arg Ile Gln Val Ile Tyr Glu Lys
                165                 170                 175
Thr Tyr Cys Val Thr Gly Gln Leu Ile Glu Gly Leu Cys Phe Ile Pro
            180                 185                 190
Thr His Thr Ile Ala Leu Thr Gln Pro Gly His Thr Tyr Asp Thr Met
            195                 200                 205
Thr Leu Pro Val Thr Cys Phe Leu Val Ala Lys Lys Leu Gly Thr Gln
            210                 215                 220
Leu Lys Leu Ala Val Glu Leu Glu Lys Leu Ile Thr Gly Val Ser Cys
225                 230                 235                 240
Thr Glu Asn Ser Phe Gln Gly Tyr Tyr Ile Cys Phe Ile Gly Lys His
                245                 250                 255
Ser Glu Pro Leu Phe Val Pro Thr Met Glu Asp Tyr Arg Ser Ala Glu
            260                 265                 270
Leu Phe Thr Arg Met Val Leu Asn Pro Arg Gly Glu Asp His Asp Pro
            275                 280                 285
Asp Gln Asn Gly Gln Gly Leu Met Arg Ile Ala Gly Pro Val Thr Ala
            290                 295                 300
Lys Val Pro Ser Thr Glu Thr Thr Glu Thr Met Gln Gly Ile Ala Phe
305                 310                 315                 320
Ala Gly Ala Pro Met Tyr Ser Ser Phe Ser Thr Leu Val Arg Lys Ala
                325                 330                 335
Asp Pro Glu Tyr Val Phe Ser Pro Gly Ile Ala Glu Ser Asn His
            340                 345                 350
Ser Val Cys Asp Lys Lys Thr Val Pro Leu Thr Trp Thr Gly Phe Leu
            355                 360                 365
Ala Val Ser Gly Glu Ile Glu Arg Ile Thr Gly Cys Thr Val Phe Cys
            370                 375                 380
Thr Leu Ala Gly Pro Gly Ala Ser Cys Glu Ala Tyr Ser Glu Thr Gly
385                 390                 395                 400
Ile Phe Asn Ile Ser Ser Pro Thr Cys Leu Val Asn Lys Val Gln Lys
                405                 410                 415
Phe Arg Gly Ser Glu Gln Arg Ile Asn Phe Met Cys Gln Arg Val Asp
            420                 425                 430
Gln Asp Val Val Val Tyr Cys Asn Gly Gln Lys Lys Val Ile Leu Thr
            435                 440                 445
```

```
Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Val Thr Leu Ile Ile Leu Lys Ile
                500                 505                 510

Leu Arg Leu Leu Thr Phe Ser Cys Ser His Tyr Ser Thr Glu Ser Lys
            515                 520                 525

Phe Lys Val Ile Leu Glu Arg Val Lys Val Glu Tyr Gln Lys Thr Met
    530                 535                 540

Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Ile Thr Glu Ser Thr Glu Ser Ala Leu Gln Ala His Phe
                580                 585                 590

Ser Ile Cys Lys Leu Thr Asn Arg Phe Gln Glu Ile Leu Lys Lys Ser
            595                 600                 605

Leu Lys Arg Pro Glu Val Arg Lys Gly Cys Tyr Arg Thr Leu Gly Val
    610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655

Met Glu Ser Gly Trp Ser Asp Thr Ala His Gly Val Gly Ile Val Pro
                660                 665                 670

Met Lys Thr Asp Leu Glu Leu Asp Phe Ala Leu Ala Ser Ser Ser Ser
            675                 680                 685

Tyr Ser Tyr Arg Arg Lys Leu Val Asn Pro Ala Asn Gln Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
                740                 745                 750

Ala Lys Cys Phe Phe Glu Lys Asp Tyr Gln Tyr Glu Thr Ser Trp Gly
            755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
                805                 810                 815

Gln Thr Cys Lys His Ile Asp Val Asn Asp Cys Leu Val Thr Pro Ser
                820                 825                 830

Val Lys Val Cys Met Ile Gly Thr Ile Ser Lys Leu Gln Pro Gly Asp
            835                 840                 845

Thr Leu Leu Phe Leu Gly Pro Leu Glu Gln Gly Gly Ile Ile Leu Lys
    850                 855                 860
```

```
Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
                900                 905                 910

Thr Val Ser Gly Phe Gln Arg Met Met Ala Thr Arg Asp Ser Phe Gln
                915                 920                 925

Ser Phe Asn Val Thr Glu Pro His Ile Thr Ser Asn Arg Leu Glu Trp
930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
                980                 985                 990

Thr Leu Val Cys Thr Val Gly Leu Thr Glu Cys Ala Asn Phe Ile Thr
                995                 1000                1005

Ser Ile Lys Ala Cys Asp Ser Ala Met Cys Tyr Gly Ala Thr Val
        1010                1015                1020

Thr Asn Leu Leu Arg Gly Ser Asn Thr Val Lys Val Val Gly Lys
        1025                1030                1035

Gly Gly His Ser Gly Ser Leu Phe Lys Cys Cys His Asp Thr Asp
        1040                1045                1050

Cys Thr Glu Glu Gly Leu Ala Ala Ser Pro Pro His Leu Asp Arg
        1055                1060                1065

Val Thr Gly Tyr Asn Gln Ile Asp Ser Asp Lys Val Tyr Asp Asp
        1070                1075                1080

Gly Ala Pro Pro Cys Thr Ile Lys Cys Trp Phe Thr Arg Ser Gly
        1085                1090                1095

Glu Trp Leu Leu Gly Ile Leu Asn Gly Asn Trp Val Val Val Ala
        1100                1105                1110

Val Leu Ile Val Ile Leu Ile Leu Ser Ile Leu Leu Phe Ser Phe
        1115                1120                1125

Phe Cys Pro Val Arg Asn Arg Lys Asn Lys Ala Asn
        1130                1135                1140

<210> SEQ ID NO 17
<211> LENGTH: 1140
<212> TYPE: PRT
<213> ORGANISM: Sin Nombre virus
<220> FEATURE:
<223> OTHER INFORMATION: strain Convict Creek 107 isolate 74

<400> SEQUENCE: 17

Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
                20                  25                  30

Thr Val Gly Leu Gly Gln Gly Tyr Val Thr Gly Ser Val Glu Thr Thr
            35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Thr Gln Lys Tyr Asn Gln
65                  70                  75                  80
```

```
Val Asp Trp Thr Lys Lys Ser Ser Thr Thr Glu Ser Thr Asn Ala Gly
                 85                  90                  95
Ala Thr Thr Phe Glu Ala Lys Thr Lys Glu Val Asn Leu Lys Gly Thr
            100                 105                 110
Cys Asn Ile Pro Pro Thr Thr Phe Glu Ala Ala Phe Lys Ser Arg Lys
        115                 120                 125
Thr Val Ile Cys Tyr Asp Leu Ala Cys Asn Gln Thr His Cys Leu Pro
    130                 135                 140
Thr Val His Leu Ile Ala Pro Val Gln Thr Cys Met Ser Val Arg Ser
145                 150                 155                 160
Cys Met Ile Gly Leu Leu Ser Ser Arg Ile Gln Val Ile Tyr Glu Lys
                165                 170                 175
Thr Tyr Cys Val Thr Gly Gln Leu Ile Glu Gly Leu Cys Phe Ile Pro
            180                 185                 190
Thr His Thr Ile Ala Leu Thr Gln Pro Gly His Thr Tyr Asp Thr Met
        195                 200                 205
Thr Leu Pro Val Thr Cys Phe Leu Val Ala Lys Lys Leu Gly Thr Gln
    210                 215                 220
Leu Lys Leu Ala Val Glu Leu Glu Lys Leu Ile Thr Gly Val Ser Cys
225                 230                 235                 240
Thr Glu Asn Ser Phe Gln Gly Tyr Tyr Ile Cys Phe Ile Gly Lys His
                245                 250                 255
Ser Glu Pro Leu Phe Val Pro Thr Met Glu Asp Tyr Arg Ser Ala Glu
            260                 265                 270
Leu Phe Thr Arg Met Val Leu Asn Pro Arg Gly Glu Asp His Asp Pro
        275                 280                 285
Asp Gln Asn Gly Gln Gly Leu Met Arg Ile Ala Gly Pro Val Thr Ala
    290                 295                 300
Lys Val Pro Ser Thr Glu Thr Thr Glu Thr Met Gln Gly Ile Ala Phe
305                 310                 315                 320
Ala Gly Ala Pro Met Tyr Ser Ser Phe Ser Thr Leu Val Arg Lys Ala
                325                 330                 335
Asp Pro Glu Tyr Val Phe Ser Pro Gly Ile Ile Ala Glu Ser Asn His
            340                 345                 350
Ser Val Cys Asp Lys Lys Thr Val Pro Leu Thr Trp Thr Gly Phe Leu
        355                 360                 365
Ala Val Ser Gly Glu Ile Glu Arg Ile Thr Gly Cys Thr Val Phe Cys
    370                 375                 380
Thr Leu Ala Gly Pro Gly Ala Ser Cys Glu Ala Tyr Ser Glu Thr Gly
385                 390                 395                 400
Ile Phe Asn Ile Ser Ser Pro Thr Cys Leu Val Asn Lys Val Gln Lys
                405                 410                 415
Phe Arg Gly Ser Glu Gln Arg Ile Asn Phe Met Cys Gln Arg Val Asp
            420                 425                 430
Gln Asp Val Val Tyr Cys Asn Gly Gln Lys Val Ile Leu Thr
        435                 440                 445
Lys Thr Leu Val Ile Gly Gln Cys Ile Tyr Thr Phe Thr Ser Leu Phe
    450                 455                 460
Ser Leu Ile Pro Gly Val Ala His Ser Leu Val Glu Leu Cys Val
465                 470                 475                 480
Pro Gly Leu His Gly Trp Ala Thr Thr Ala Leu Leu Ile Thr Phe Cys
                485                 490                 495
Phe Gly Trp Leu Leu Ile Pro Thr Val Thr Leu Ile Ile Leu Lys Ile
```

-continued

```
                500                 505                 510
Leu Arg Leu Leu Thr Phe Ser Cys Ser His Tyr Ser Thr Glu Ser Lys
            515                 520                 525
Phe Lys Val Ile Leu Glu Arg Val Lys Val Glu Tyr Gln Lys Thr Met
            530                 535                 540
Gly Ser Met Val Cys Asp Ile Cys His His Glu Cys Glu Thr Ala Lys
545                 550                 555                 560
Glu Leu Glu Thr His Lys Lys Ser Cys Pro Glu Gly Gln Cys Pro Tyr
                565                 570                 575
Cys Met Thr Ile Thr Glu Ser Thr Glu Ser Ala Leu Gln Ala His Phe
                580                 585                 590
Ser Ile Cys Lys Leu Thr Asn Arg Phe Gln Glu Ile Leu Lys Lys Ser
            595                 600                 605
Leu Lys Arg Pro Glu Val Arg Lys Gly Cys Tyr Arg Thr Leu Gly Val
            610                 615                 620
Phe Arg Tyr Lys Ser Arg Cys Tyr Val Gly Leu Val Trp Gly Ile Leu
625                 630                 635                 640
Leu Thr Thr Glu Leu Ile Ile Trp Ala Ala Ser Ala Asp Thr Pro Leu
                645                 650                 655
Met Glu Ser Gly Trp Ser Asp Thr Ala His Gly Val Gly Ile Val Pro
                660                 665                 670
Met Lys Thr Asp Leu Glu Leu Asp Phe Ala Leu Ala Ser Ser Ser Ser
            675                 680                 685
Tyr Ser Tyr Arg Arg Lys Leu Val Asn Pro Ala Asn Gln Glu Glu Thr
            690                 695                 700
Leu Pro Phe His Phe Gln Leu Asp Lys Gln Val Val His Ala Glu Ile
705                 710                 715                 720
Gln Asn Leu Gly His Trp Met Asp Gly Thr Phe Asn Ile Lys Thr Ala
                725                 730                 735
Phe His Cys Tyr Gly Glu Cys Lys Lys Tyr Ala Tyr Pro Trp Gln Thr
                740                 745                 750
Ala Lys Cys Phe Phe Glu Lys Asp Tyr Gln Tyr Glu Thr Ser Trp Gly
            755                 760                 765
Cys Asn Pro Pro Asp Cys Pro Gly Val Gly Thr Gly Cys Thr Ala Cys
            770                 775                 780
Gly Val Tyr Leu Asp Lys Leu Arg Ser Val Gly Lys Ala Tyr Lys Ile
785                 790                 795                 800
Val Ser Leu Lys Tyr Thr Arg Lys Val Cys Ile Gln Leu Gly Thr Glu
                805                 810                 815
Gln Thr Cys Lys His Ile Asp Val Asn Asp Cys Leu Val Thr Pro Ser
                820                 825                 830
Val Lys Val Cys Met Ile Gly Thr Ile Ser Lys Leu Gln Pro Gly Asp
            835                 840                 845
Thr Leu Leu Phe Leu Gly Pro Leu Glu Gln Gly Gly Ile Ile Leu Lys
            850                 855                 860
Gln Trp Cys Thr Thr Ser Cys Val Phe Gly Asp Pro Gly Asp Ile Met
865                 870                 875                 880
Ser Thr Thr Ser Gly Met Arg Cys Pro Glu His Thr Gly Ser Phe Arg
                885                 890                 895
Lys Ile Cys Gly Phe Ala Thr Thr Pro Thr Cys Glu Tyr Gln Gly Asn
                900                 905                 910
Thr Val Ser Gly Phe Gln Arg Met Met Ala Thr Arg Asp Ser Phe Gln
            915                 920                 925
```

Ser Phe Asn Val Thr Glu Pro His Ile Thr Ser Asn Arg Leu Glu Trp
            930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu Thr Glu Cys Ala Asn Phe Ile Thr
        995                 1000                1005

Ser Ile Lys Ala Cys Asp Ser Ala Met Cys Tyr Gly Ala Thr Val
    1010                1015                1020

Thr Asn Leu Leu Arg Gly Ser Asn Thr Val Lys Val Val Gly Lys
    1025                1030                1035

Gly Gly His Ser Gly Ser Leu Phe Lys Cys Cys His Asp Thr Asp
    1040                1045                1050

Cys Thr Glu Glu Gly Leu Ala Ala Ser Pro Pro His Leu Asp Arg
    1055                1060                1065

Val Thr Gly Tyr Asn Gln Ile Asp Ser Asp Lys Val Tyr Asp Asp
    1070                1075                1080

Gly Ala Pro Pro Cys Thr Ile Lys Cys Trp Phe Thr Lys Ser Gly
    1085                1090                1095

Glu Trp Leu Leu Gly Ile Leu Asn Gly Asn Trp Val Val Ala
    1100                1105                1110

Val Leu Ile Val Ile Leu Ile Leu Ser Ile Leu Leu Phe Ser Phe
    1115                1120                1125

Phe Cys Pro Val Arg Asn Arg Lys Asn Lys Ala Asn
    1130                1135                1140

<210> SEQ ID NO 18
<211> LENGTH: 1140
<212> TYPE: PRT
<213> ORGANISM: Sin Nombre virus
<220> FEATURE:
<223> OTHER INFORMATION: strain NMH10

<400> SEQUENCE: 18

Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Ile Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95

Ala Thr Thr Phe Glu Ala Lys Thr Lys Glu Ile Asn Leu Lys Gly Thr
            100                 105                 110

Cys Asn Ile Pro Pro Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

```
Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
            165                 170                 175

Thr Tyr Cys Val Thr Gly Gln Leu Ile Glu Gly Leu Cys Phe Ile Pro
        180                 185                 190

Thr His Thr Ile Ala Leu Thr Gln Pro Gly His Thr Tyr Asp Thr Met
    195                 200                 205

Thr Leu Pro Val Thr Cys Phe Leu Val Ala Lys Lys Leu Gly Thr Gln
210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
            245                 250                 255

Ser Glu Pro Leu Phe Val Pro Thr Met Glu Asp Tyr Arg Ser Ala Glu
        260                 265                 270

Leu Phe Thr Arg Met Val Leu Asn Pro Arg Gly Glu Asp His Asp Pro
    275                 280                 285

Asp Gln Asn Gly Gln Gly Leu Met Arg Ile Ala Gly Pro Val Thr Ala
290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
            325                 330                 335

Asp Pro Glu Tyr Val Phe Ser Pro Gly Ile Ile Ala Glu Ser Asn His
        340                 345                 350

Ser Val Cys Asp Lys Lys Thr Val Pro Leu Thr Trp Thr Gly Phe Leu
    355                 360                 365

Ala Val Ser Gly Glu Ile Glu Lys Ile Thr Gly Cys Thr Val Phe Cys
370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
            405                 410                 415

Phe Arg Gly Ser Glu Gln Arg Ile Asn Phe Met Cys Gln Arg Val Asp
        420                 425                 430

Gln Asp Val Val Val Tyr Cys Asn Gly Gln Lys Lys Val Ile Leu Thr
    435                 440                 445

Lys Thr Leu Val Ile Gly Gln Cys Ile Tyr Thr Phe Thr Ser Leu Phe
450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
            485                 490                 495

Phe Gly Trp Leu Leu Ile Pro Ala Val Thr Leu Ile Ile Leu Lys Ile
        500                 505                 510

Leu Arg Leu Leu Thr Phe Ser Cys Ser His Tyr Ser Thr Glu Ser Lys
    515                 520                 525

Phe Lys Val Ile Leu Glu Arg Val Lys Val Glu Tyr Gln Lys Thr Met
530                 535                 540

Gly Ser Met Val Cys Asp Ile Cys His His Glu Cys Glu Thr Ala Lys
545                 550                 555                 560
```

```
Glu Leu Glu Thr His Lys Lys Ser Cys Pro Gly Gln Cys Pro Tyr
                565                 570                 575

Cys Met Thr Ile Thr Glu Ser Thr Glu Ser Ala Leu Gln Ala His Phe
            580                 585                 590

Ala Ile Cys Lys Leu Thr Asn Arg Phe Gln Glu Asn Leu Lys Lys Ser
            595                 600                 605

Leu Lys Arg Pro Glu Val Arg Lys Gly Cys Tyr Arg Thr Leu Gly Val
        610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655

Met Glu Ser Gly Trp Ser Asp Thr Ala His Gly Val Gly Ile Ile Pro
            660                 665                 670

Met Lys Thr Asp Leu Glu Leu Asp Phe Ala Leu Ala Ser Ser Ser Ser
            675                 680                 685

Tyr Ser Tyr Arg Arg Lys Leu Val Asn Pro Ala Asn Gln Glu Glu Thr
        690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
            755                 760                 765

Cys Asn Pro Pro Asp Cys Pro Gly Val Gly Thr Gly Cys Thr Ala Cys
        770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
                805                 810                 815

Gln Thr Cys Lys His Ile Asp Val Asn Asp Cys Leu Val Thr Pro Ser
            820                 825                 830

Val Lys Val Cys Met Ile Gly Thr Ile Ser Lys Leu Gln Pro Gly Asp
            835                 840                 845

Thr Leu Leu Phe Leu Gly Pro Leu Glu Gln Gly Gly Ile Ile Leu Lys
        850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
            900                 905                 910

Thr Val Ser Gly Phe Gln Arg Met Met Ala Thr Arg Asp Ser Phe Gln
            915                 920                 925

Ser Phe Asn Val Thr Glu Pro His Ile Thr Ser Asn Arg Leu Glu Trp
        930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
```

```
                  980              985             990
Thr Leu Val Cys Thr Val Gly Leu Thr Glu Cys Ala Asn Phe Ile Thr
                995            1000           1005

Ser Ile Lys Ala Cys Asp Ser Ala Met Cys Tyr Gly Ala Thr Val
        1010            1015           1020

Thr Asn Leu Leu Arg Gly Ser Asn Thr Val Lys Val Val Gly Lys
        1025            1030           1035

Gly Gly His Ser Gly Ser Leu Phe Lys Cys Cys His Asp Thr Asp
        1040            1045           1050

Cys Thr Glu Glu Gly Leu Ala Ala Ser Pro Pro His Leu Asp Arg
        1055            1060           1065

Val Thr Gly Tyr Asn Gln Ile Asp Ser Asp Lys Val Tyr Asp Asp
        1070            1075           1080

Gly Ala Pro Pro Cys Thr Ile Lys Cys Trp Phe Thr Lys Ser Gly
        1085            1090           1095

Glu Trp Leu Leu Gly Ile Leu Asn Gly Asn Trp Val Val Val Ala
        1100            1105           1110

Val Leu Ile Val Ile Leu Ile Leu Ser Ile Leu Leu Phe Ser Phe
        1115            1120           1125

Phe Cys Pro Val Arg Ser Arg Lys Asn Lys Ala Asn
        1130            1135           1140

<210> SEQ ID NO 19
<211> LENGTH: 1140
<212> TYPE: PRT
<213> ORGANISM: New York virus

<400> SEQUENCE: 19

Met Val Gly Trp Val Cys Ile Ser Leu Val Val Leu Ala Thr Thr Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Thr Asp Leu Lys Ile Glu Ser Ser Cys
    50                  55                  60

Asn Phe Asp Leu His Val Pro Ser Thr Ser Ile Gln Lys Tyr Asn Gln
65                  70                  75                  80

Val Glu Trp Ala Lys Lys Ser Ser Thr Glu Ser Thr Ser Ala Gly
                85                  90                  95

Ala Thr Thr Phe Glu Ala Lys Thr Lys Glu Val Ser Leu Lys Gly Thr
            100                 105                 110

Cys Asn Ile Pro Val Thr Thr Phe Glu Ala Ala Tyr Lys Ser Arg Lys
            115                 120                 125

Thr Val Ile Cys Tyr Asp Leu Ala Cys Asn Gln Thr His Cys Leu Pro
        130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Val Glu Gly Leu Cys Phe Ile Pro
            180                 185                 190

Thr His Thr Ile Ala Leu Thr Gln Pro Gly His Thr Tyr Asp Thr Met
            195                 200                 205
```

```
Thr Leu Pro Ile Thr Cys Phe Leu Val Ala Lys Lys Leu Gly Thr Gln
210                 215                 220

Leu Lys Ile Ala Val Glu Leu Glu Lys Leu Ile Thr Ala Ser Gly Cys
225                 230                 235                 240

Thr Glu Asn Ser Phe Gln Gly Tyr Tyr Ile Cys Phe Leu Gly Lys His
                245                 250                 255

Ser Glu Pro Leu Phe Val Pro Met Met Asp Asp Tyr Arg Ser Ala Glu
                260                 265                 270

Leu Phe Thr Arg Met Val Leu Asn Pro Arg Gly Glu Asp His Asp Pro
            275                 280                 285

Asp Gln Asn Gly Gln Gly Leu Met Arg Ile Ala Gly Pro Ile Thr Ala
        290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Asp Tyr Val Phe Ser Pro Gly Ile Ile Ala Glu Ser Asn His
                340                 345                 350

Ser Val Cys Asp Lys Lys Thr Ile Pro Leu Thr Trp Thr Gly Phe Leu
            355                 360                 365

Ala Val Ser Gly Glu Ile Glu Lys Ile Thr Gly Cys Thr Val Phe Cys
        370                 375                 380

Thr Leu Val Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Ile Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Ile Thr Met Ile Ile Leu Lys Ile
                500                 505                 510

Leu Arg Leu Leu Thr Phe Ser Cys Ser His Tyr Ser Thr Glu Ser Lys
            515                 520                 525

Phe Lys Ala Ile Leu Glu Arg Val Lys Val Glu Tyr Gln Lys Thr Met
        530                 535                 540

Gly Ser Met Val Cys Asp Val Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Met Thr Glu Ser Thr Glu Ser Ala Leu Gln Ala His Phe
                580                 585                 590

Ser Ile Cys Lys Leu Thr Asn Arg Phe Gln Glu Asn Leu Lys Lys Ser
            595                 600                 605

Leu Lys Arg Pro Glu Val Lys Gln Gly Cys Tyr Arg Thr Leu Gly Val
        610                 615                 620

Phe Arg Tyr Lys Ser Arg Cys Tyr Val Gly Leu Val Trp Gly Val Leu
```

```
            625                 630                 635                 640
Leu Thr Thr Glu Leu Ile Val Trp Ala Ala Ser Ala Asp Thr Pro Leu
                    645                 650                 655
Met Glu Ser Gly Trp Ser Asp Thr Ala His Gly Val Gly Ile Val Pro
                660                 665                 670
Met Lys Thr Asp Leu Glu Leu Asp Phe Ala Leu Ala Ser Ser Ser Ser
                675                 680                 685
Tyr Ser Tyr Arg Arg Lys Leu Val Asn Pro Ala Asn Lys Glu Glu Thr
        690                 695                 700
Leu Pro Phe His Phe Gln Leu Asp Lys Gln Val Val His Ala Glu Ile
705                 710                 715                 720
Gln Asn Leu Gly His Trp Met Asp Gly Thr Phe Asn Ile Lys Thr Ala
                    725                 730                 735
Phe His Cys Tyr Gly Glu Cys Lys Lys Tyr Ala Tyr Pro Trp Gln Thr
                740                 745                 750
Ala Lys Cys Phe Phe Glu Lys Asp Tyr Gln Tyr Glu Thr Ser Trp Gly
                755                 760                 765
Cys Asn Pro Pro Asp Cys Pro Gly Val Gly Thr Gly Cys Thr Ala Cys
        770                 775                 780
Gly Val Tyr Leu Asp Lys Leu Arg Ser Val Gly Lys Ala Tyr Lys Ile
785                 790                 795                 800
Val Ser Leu Lys Phe Thr Arg Lys Val Cys Ile Gln Leu Gly Thr Glu
                    805                 810                 815
Gln Thr Cys Lys His Ile Asp Val Asn Asp Cys Leu Val Thr Pro Ser
                820                 825                 830
Val Lys Val Cys Leu Ile Gly Thr Ile Ser Lys Leu Gln Pro Gly Asp
                835                 840                 845
Thr Leu Leu Phe Leu Gly Pro Leu Glu Gln Gly Ile Ile Leu Lys
        850                 855                 860
Gln Trp Cys Thr Thr Ser Cys Val Phe Gly Asp Pro Gly Asp Ile Met
865                 870                 875                 880
Ser Thr Thr Thr Gly Met Lys Cys Pro Glu His Thr Gly Ser Phe Arg
                    885                 890                 895
Lys Ile Cys Gly Phe Ala Thr Thr Pro Thr Cys Glu Tyr Gln Gly Asn
                900                 905                 910
Thr Ile Ser Gly Phe Gln Arg Met Met Ala Thr Arg Asp Ser Phe Gln
                915                 920                 925
Ser Phe Asn Val Thr Glu Pro His Ile Thr Ser Asn Arg Leu Glu Trp
        930                 935                 940
Ile Asp Pro Asp Ser Ser Ile Lys Asp His Ile Asn Met Val Leu Asn
945                 950                 955                 960
Arg Asp Val Ser Phe Gln Asp Leu Ser Asp Asn Pro Cys Lys Val Asp
                    965                 970                 975
Leu His Thr Gln Ser Ile Asp Gly Ala Trp Gly Ser Gly Val Gly Phe
                980                 985                 990
Thr Leu Val Cys Thr Val Gly Leu  Thr Glu Cys Ala Asn  Phe Ile Thr
                995                  1000                 1005
Ser Ile  Lys Ala Cys Asp Ser  Ala Met Cys Tyr Gly  Ala Thr Val
        1010                 1015                 1020
Thr Asn  Leu Leu Arg Gly Ser  Asn Thr Val Lys Val  Val Gly Lys
        1025                 1030                 1035
Gly Gly  His Ser Gly Ser Leu  Phe Lys Cys Cys His  Asp Thr Asp
        1040                 1045                 1050
```

```
Cys Thr Glu Glu Gly Leu Ala Ala Ser Pro Pro His Leu Asp Arg
    1055                1060                1065

Val Thr Gly Tyr Asn Gln Ile Asp Ser Asp Lys Val Tyr Asp Asp
    1070                1075                1080

Gly Ala Pro Pro Cys Thr Ile Lys Cys Trp Phe Thr Lys Ser Gly
    1085                1090                1095

Glu Trp Leu Leu Gly Ile Leu Asn Gly Asn Trp Val Val Val Ala
    1100                1105                1110

Val Leu Ile Val Ile Leu Ile Leu Ser Ile Leu Leu Phe Ser Phe
    1115                1120                1125

Phe Cys Pro Ile Arg Gly Arg Lys Asn Lys Ser Asn
    1130                1135                1140

<210> SEQ ID NO 20
<211> LENGTH: 1140
<212> TYPE: PRT
<213> ORGANISM: New York virus

<400> SEQUENCE: 20

Met Val Gly Phe Val Cys Ile Phe Leu Val Val Leu Ala Thr Thr Thr
1               5                   10                  15

Ala Gly Leu Thr Arg Asn Leu Tyr Glu Leu Lys Ile Glu Cys Pro His
                20                  25                  30

Thr Val Gly Leu Gly Gln Gly Tyr Val Thr Gly Ser Val Gly Thr Thr
            35                  40                  45

Pro Ile Leu Leu Thr Gln Val Thr Asp Leu Lys Ile Glu Ser Ser Cys
50                  55                  60

Asn Phe Asp Leu His Val Pro Ser Thr Ser Ile Gln Lys Tyr Asn Gln
65                  70                  75                  80

Val Glu Trp Ala Lys Lys Ser Ser Thr Thr Glu Ser Thr Ser Ala Gly
                85                  90                  95

Ala Thr Thr Phe Glu Ala Lys Thr Lys Glu Val Ser Leu Lys Gly Thr
            100                 105                 110

Cys Asn Ile Pro Val Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Val Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Ile Thr Cys Phe Leu Val Ala Lys Lys Leu Gly Thr Gln
    210                 215                 220

Leu Lys Ile Ala Val Glu Leu Glu Lys Leu Ile Thr Ala Gly Gly Cys
225                 230                 235                 240

Thr Glu Asn Ser Phe Gln Gly Tyr Tyr Ile Cys Phe Leu Gly Lys His
                245                 250                 255

Ser Glu Pro Leu Phe Val Pro Met Met Asp Asp Tyr Arg Ser Ala Glu
            260                 265                 270

Leu Phe Thr Arg Met Val Leu Asn Pro Arg Gly Glu Asp His Asp Pro
```

-continued

```
             275                 280                 285
Asp Gln Asn Gly Gln Gly Leu Met Arg Ile Ala Gly Pro Ile Thr Ala
290                 295                 300

Lys Val Pro Ser Thr Glu Thr Thr Glu Ala Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Asp Tyr Val Phe Ser Pro Gly Ile Ile Ala Glu Ser Asn His
                340                 345                 350

Ser Val Cys Asp Lys Lys Thr Ile Pro Leu Thr Trp Thr Gly Phe Leu
                355                 360                 365

Ala Val Ser Gly Glu Ile Glu Lys Ile Thr Gly Cys Thr Val Phe Cys
370                 375                 380

Thr Leu Val Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
                420                 425                 430

Gln Asp Val Ile Val Tyr Cys Asn Gly Gln Lys Lys Val Ile Leu Thr
                435                 440                 445

Lys Thr Leu Val Ile Gly Gln Cys Ile Tyr Thr Phe Thr Ser Leu Phe
450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Ile Thr Met Ile Ile Leu Lys Ile
                500                 505                 510

Leu Arg Leu Leu Thr Phe Ser Cys Ser His Tyr Ser Thr Glu Ser Lys
                515                 520                 525

Phe Lys Ala Ile Leu Glu Arg Val Lys Val Glu Tyr Gln Lys Thr Met
530                 535                 540

Gly Ser Met Val Cys Asp Val Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Met Thr Glu Ser Thr Glu Ser Ala Leu Gln Ala His Phe
                580                 585                 590

Ser Ile Cys Lys Leu Thr Asn Arg Phe Gln Glu Asn Leu Lys Lys Ser
                595                 600                 605

Leu Lys Arg Pro Glu Val Lys Gln Gly Cys Tyr Arg Thr Leu Gly Val
                610                 615                 620

Phe Arg Tyr Lys Ser Arg Cys Tyr Val Gly Leu Val Trp Gly Val Leu
625                 630                 635                 640

Leu Thr Thr Glu Leu Ile Val Trp Ala Ala Ser Ala Asp Thr Pro Leu
                645                 650                 655

Met Glu Ser Gly Trp Ser Asp Thr Ala His Gly Val Gly Ile Val Pro
                660                 665                 670

Met Lys Thr Asp Leu Glu Leu Asp Phe Ala Leu Ala Ser Ser Ser Ser
                675                 680                 685

Tyr Ser Tyr Arg Arg Lys Leu Val Asp Pro Ala Asn Lys Glu Glu Thr
                690                 695                 700
```

```
Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
            725                 730                 735

Phe His Cys Tyr Gly Glu Cys Lys Lys Tyr Ala Tyr Pro Trp Gln Thr
        740                 745                 750

Ala Lys Cys Phe Phe Glu Lys Asp Tyr Gln Tyr Glu Thr Ser Trp Gly
    755                 760                 765

Cys Asn Pro Pro Asp Cys Pro Gly Val Gly Thr Gly Cys Thr Ala Cys
770                 775                 780

Gly Val Tyr Leu Asp Lys Leu Arg Ser Val Gly Lys Ala Tyr Lys Ile
785                 790                 795                 800

Val Ser Leu Lys Phe Thr Arg Lys Val Cys Ile Gln Leu Gly Thr Glu
            805                 810                 815

Gln Thr Cys Lys His Ile Asp Val Asn Asp Cys Leu Val Thr Pro Ser
        820                 825                 830

Val Lys Val Cys Leu Ile Gly Thr Ile Ser Lys Leu Gln Pro Gly Asp
    835                 840                 845

Thr Leu Leu Phe Leu Gly Pro Leu Glu Gln Gly Ile Ile Leu Lys
850                 855                 860

Gln Trp Cys Thr Thr Ser Cys Val Phe Gly Asp Pro Gly Asp Ile Met
865                 870                 875                 880

Ser Thr Thr Thr Gly Met Lys Cys Pro Glu His Thr Gly Ser Phe Arg
            885                 890                 895

Lys Ile Cys Gly Phe Ala Thr Thr Pro Thr Cys Glu Tyr Gln Gly Asn
        900                 905                 910

Thr Ile Ser Gly Phe Gln Arg Met Met Ala Thr Arg Asp Ser Phe Gln
    915                 920                 925

Ser Phe Asn Val Thr Glu Pro His Ile Thr Ser Asn Arg Leu Glu Trp
930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
            965                 970                 975

Leu His Thr Gln Ser Ile Asp Gly Ala Trp Gly Ser Gly Val Gly Phe
        980                 985                 990

Thr Leu Val Cys Thr Val Gly Leu Thr Glu Cys Ala Asn Phe Ile Thr
    995                 1000                1005

Ser Ile Lys Ala Cys Asp Ser Ala Met Cys Tyr Gly Ala Thr Val
    1010                1015                1020

Thr Asn Leu Leu Arg Gly Ser Asn Thr Val Lys Val Val Gly Lys
    1025                1030                1035

Gly Gly His Ser Gly Ser Leu Phe Lys Cys Cys His Asp Thr Asp
    1040                1045                1050

Cys Thr Glu Glu Gly Leu Ala Ala Ser Pro Pro His Leu Asp Arg
    1055                1060                1065

Val Thr Gly Tyr Asn Gln Ile Asp Ser Asp Lys Val Tyr Asp Asp
    1070                1075                1080

Gly Ala Pro Pro Cys Thr Ile Lys Cys Trp Phe Thr Lys Ser Gly
    1085                1090                1095

Glu Trp Leu Leu Gly Ile Leu Asn Gly Asn Trp Val Val Val Ala
    1100                1105                1110
```

```
Val Leu Ile Val Ile Leu Ile Leu Ser Ile Leu Leu Phe Ser Phe
    1115                1120                1125

Phe Cys Pro Ile Arg Gly Arg Lys Asn Lys Ser Asn
    1130                1135                1140

<210> SEQ ID NO 21
<211> LENGTH: 1140
<212> TYPE: PRT
<213> ORGANISM: New York virus
<220> FEATURE:
<223> OTHER INFORMATION: strain Rhode Island-1

<400> SEQUENCE: 21

Met Val Gly Trp Val Cys Ile Phe Leu Val Val Leu Ala Thr Thr Thr
  1               5                  10                  15

Ala Gly Leu Thr Arg Asn Leu Tyr Glu Leu Lys Ile Glu Cys Pro His
             20                  25                  30

Thr Val Gly Leu Gly Gln Gly Tyr Val Thr Gly Ser Val Glu Thr Thr
         35                  40                  45

Pro Ile Leu Leu Thr Gln Val Thr Asp Leu Lys Ile Glu Ser Ser Cys
     50                  55                  60

Asn Ph

```
Asp Pro Asp Tyr Val Phe Ser Pro Gly Ile Ile Ala Glu Ser Asn His
            340                 345                 350

Ser Val Cys Asp Lys Lys Ala Ile Pro Leu Thr Trp Thr Gly Phe Leu
        355                 360                 365

Ala Val Ser Gly Glu Ile Glu Lys Ile Thr Gly Cys Thr Val Phe Cys
    370                 375                 380

Thr Leu Val Gly Pro Gly Ala Ser Cys Lys Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Ile Val Tyr Cys Asn Gly Gln Lys Lys Val Ile Leu Thr
        435                 440                 445

Lys Thr Leu Ile Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Ala Ala Leu Leu Ile Thr Phe Cys
                485                 490                 495

Phe Gly Trp Leu Leu Ile Pro Thr Ile Thr Met Ile Ile Leu Lys Ile
            500                 505                 510

Leu Arg Leu Leu Thr Phe Ser Cys Ser His Tyr Ser Thr Glu Ser Lys
        515                 520                 525

Phe Lys Ala Ile Leu Glu Arg Val Lys Val Glu Tyr Gln Lys Thr Met
    530                 535                 540

Gly Ser Met Val Cys Asp Ala Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Met Thr Glu Ser Thr Glu Ser Ala Leu Leu Ala His Phe
            580                 585                 590

Ser Ile Cys Lys Leu Thr Asn Arg Phe Gln Glu Asn Leu Lys Lys Ser
        595                 600                 605

Leu Lys Arg Pro Glu Val Lys Gln Gly Arg Tyr Arg Thr Leu Gly Val
    610                 615                 620

Phe Arg Tyr Lys Ser Arg Cys Tyr Val Gly Leu Val Trp Gly Val Leu
625                 630                 635                 640

Leu Thr Thr Glu Leu Ile Val Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Lys Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
```

```
                755                 760                 765
Cys Asn Pro Pro Asp Cys Pro Gly Val Gly Thr Gly Cys Thr Ala Cys
770                 775                 780

Gly Val Tyr Leu Asp Lys Leu Arg Ser Gly Gly Lys Ala Tyr Lys Ile
785                 790                 795                 800

Val Ser Leu Lys Phe Thr Arg Lys Val Cys Ile Gln Leu Gly Thr Glu
                805                 810                 815

Gln Thr Cys Lys His Ile Asp Val Asn Asp Cys Leu Val Thr Pro Ser
                820                 825                 830

Val Lys Val Cys Leu Ile Gly Thr Ile Ser Lys Leu Gln Pro Gly Asp
                835                 840                 845

Thr Leu Leu Phe Leu Gly Pro Leu Glu Gln Gly Ile Ile Leu Lys
850                 855                 860

Gln Trp Cys Thr Thr Ser Cys Val Phe Gly Asp Pro Gly Asp Ile Met
865                 870                 875                 880

Ser Thr Thr Thr Gly Met Lys Cys Pro Glu His Thr Gly Ser Phe Arg
                885                 890                 895

Lys Ile Cys Gly Phe Ala Thr Thr Pro Thr Cys Glu Tyr Gln Gly Asn
                900                 905                 910

Thr Ile Ser Gly Phe Gln Arg Met Met Ala Thr Arg Asp Ser Phe Gln
                915                 920                 925

Ser Phe Asn Val Thr Glu Pro His Ile Thr Ser Asn Arg Leu Glu Trp
930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
                980                 985                 990

Thr Leu Val Cys Thr Val Gly Leu Thr Glu Cys Ala Asn Phe Ile Thr
                995                 1000                1005

Ser Ile Lys Ala Cys Asp Ser Ala Met Cys Tyr Gly Ala Thr Val
1010                1015                1020

Thr Asn Leu Leu Arg Gly Ser Asn Thr Val Lys Val Val Gly Lys
1025                1030                1035

Gly Gly His Ser Ser Ser Leu Phe Lys Cys Cys His Asp Thr Asp
1040                1045                1050

Cys Thr Glu Glu Gly Leu Ala Ala Ser Pro Pro His Leu Asp Arg
1055                1060                1065

Val Thr Gly Tyr Asn Gln Ile Asp Ser Asp Lys Val Tyr Asp Asp
1070                1075                1080

Gly Ala Pro Pro Cys Thr Ile Lys Cys Trp Phe Thr Lys Ser Gly
1085                1090                1095

Glu Trp Leu Leu Gly Ile Leu Asn Gly Asn Trp Val Val Val Ala
1100                1105                1110

Val Leu Ile Val Ile Leu Ile Leu Ser Ile Leu Leu Phe Ser Phe
1115                1120                1125

Phe Cys Pro Ile Arg Gly Arg Lys Asn Lys Ser Asn
1130                1135                1140

<210> SEQ ID NO 22
<211> LENGTH: 3733
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 22

```
gcggccgcgg atctgcagga attcggcacg agagtagtag actccgcacg aagaagcaaa      60
cactgaataa aggatataca gaatggtagg gtgggtttgc atcttcctcg tggtccttac     120
tactgcaact gctggattga cacggaatct ctatgaatta cagatagaat gtccacatac     180
tgtgggtcta ggtcaaggtt atgtgacagg ttctgtagaa actacaccta ttctcttaac     240
acaggtagct gacctcaaga ttgagagttc ttgcaatttt gacttgcatg tcccagccac     300
tactactcag aaatacaatc aagttgactg gactaaaaaa agttctacta cagaaagcac     360
gaatgcaggt gcaactacat ttgaggctaa aacaaaagag gtaaatttaa aaggcacatg     420
taatattcct ccaactacgt tgaggctgc atacaagtca aggaagacag tgatttgtta      480
tgatttggcc tgtaatcaaa cacattgtct tcctacagtc catctgattg ctcctgttca     540
aacatgtatg tctgtacgga gctgtatgat aggtctgtta tctagcagga tccaggttat     600
ctacgagaag acatattgtg tcacgggtca gttaatagaa gggctatgtt tcattccaac     660
acatacaatt gcacttacac agcctggtca tacttatgat actatgacat gcctgtgac      720
ttgttttta gtagccaaaa agttggggac gcagcttaag ctggctgttg agttagagaa      780
attgattact ggtgtgagct gcgcagagaa tagcttccaa ggttattaca tctgttttat     840
tggaaaacat tcagagccct tatttgtacc aacaatggaa gattatagat cagctgagtt     900
atttactcgt atggttttaa atccaagagg tgaagatcat gaccctgatc aaaatggaca     960
agggttgatg agaatagctg gacctgttac tgccaaggta ccatctacag aaacgactga    1020
aacaatgcaa ggaattgcat ttgctggggc accaatgtat agttcattct caactcttgt    1080
gagaaaagct gatcctgaat atgtcttttc tccaggtata attgcagaat caaatcatag    1140
tgtttgtgat aaaagacag tgcccctaac atggactggg tttctagcag tttcaggaga     1200
gatagaaagg ataacaggct gtacagtttt ctgtacattg gctggacctg gtgccagttg    1260
tgaagcatac tcagaaacag gaatcttcaa cataagctcc ccaacttgct tggtaaataa    1320
agtccaaaaa tttagaggtt cagaacaaag aattaatttt atgtgtcaaa gggttgatca    1380
aggtgttgtg gtttactgta atggacagaa gaaagtcatt cttaccaaaa ccctagtaat    1440
aggtcaatgt atctacacat ttactagtct gttttcactg atccctggag ttgctcattc    1500
ccttgctgtg gagttatgtg ttccaggtct tcatggctgg gctacaacag cactacttat    1560
tactttctgc tttggctggc ttctcatacc aacagttact ttaattatac taaaaatctt    1620
aaggctattg accttcccat gctcgcacta ttctacagaa tcaaaattca agtcattttt    1680
agaaagagtc aaggtggagt atcaaaagac aatgggttca atggtgtgtg acatttgtca    1740
ccatgaatgt gagacggcaa aagagctcga acacataag aaaagttgcc cagaaggtca     1800
atgcccatac tgcatgacaa taactgagtc cactgagagt gcattacaag ctcattttc     1860
aatctgtaag ctaacgaaca ggttccagga aaatctaaaa aaatcattaa aacgtccaga    1920
agtaaggaaa ggttgttaca ggacattagg agtattccgc tacaagagca ggtgctatgt    1980
tggcttagta tgggggatcc tcttgacgac agagctgatt atatgggctg ctagtgcaga    2040
taccccctcta atggagtctg gttggtcaga tacagcacat ggtgtaggta tagtccctat    2100
gaaaacagat ttagagcttg actttgcctt ggcctcatca tcttcttata gttatagaag    2160
aaagcttgta aaccctgcca atcaagagga gacactccct tttcatttcc agttagataa    2220
```

```
gcaagtagtg catgcagaaa tacagaacct agggcattgg atggatggca cattcaacat    2280
aaagactgct ttccattgct atggagaatg taaaaaatat gcctatcctt ggcagacagc    2340
caagtgtttc tttgaaaaag attatcagta tgaaacaagc tggggctgta acccaccaga    2400
ttgcccagga gtagggacag gttgtacagc ctgtggggta tacttagaca agctccgttc    2460
agttgggaaa gcctataaaa ttgtatcact caaatacacg cgaaaggtgt gtattcaatt    2520
ggggacagaa caaacctgta aacatataga tgttaatgat tgtttggtca ccccgtctgt    2580
taaagtttgc atgataggta ccatctcgaa gcttcagcca ggtgacacct tattgttttt    2640
gggcccttta gagcaaggtg ggattattct aaaacaatgg tgcacaacat catgtgtgtt    2700
tggagaccct ggtgatatca tgtcaacaac aagtgggatg agatgccctg agcacacagg    2760
gtcttttaga aaaatctgtg gatttgctac aacacctaca tgtgaatatc aaggtaatac    2820
agtgtctgga ttccaacgca tgatggcaac tcgagattct tttcaatcat tcaatgtgac    2880
agaaccacat attaccagca atcgactgga atggattgat ccagatagta gtattaaaga    2940
ccatatcaac atggttttga atagagatgt ttccttccaa gatctaagtg ataatccatg    3000
taaggttgat ttgcatacac aatctattga tggggcttgg ggatcaggag tgggctttac    3060
attagtatgt actgtaggtc ttacagagtg tgcaaatttc ataacttcaa ttaaggcgtg    3120
tgattctgct atgtgttatg gggccacagt tacaaatcta ctcagagggt ctaacacagt    3180
taaagttgtc ggtaaaggtg ggcattctgg gtccttgttc aagtgctgcc atgatactga    3240
ctgtactgaa gaaggtttag cagcatcacc acctcattta gatagggtta ctggttacaa    3300
tcaaatagat tctgataagg tttatgatga cggtgcaccg ccctgtacaa ttaaatgttg    3360
gttcacaaag tcaggtgagt ggttgctagg aattcttaat ggcaattggg tagtagttgc    3420
tgttttgatt gtaattttga tactatcaat actcctgttc agcttctttt gtcctgttag    3480
aaatagaaaa aataaggcca attagcaaac atatatgtaa gtaagggtat gatcatatta    3540
tatcattatg cgtatactct tatatctata atatctatgt atccttatac tctaactatt    3600
tatattaatt tttactttta tacaagtatt aactaaccca ttaccagcta aaaaaaacaa    3660
acccttaaca cctatataat cccatttgct tattacgagg cttttgttcc tgcggagtct    3720
actactattc gaa                                                       3733
```

NUCLEIC ACIDS CONTAINING A SYNTHETIC CODON-OPTIMIZED SIN NOMBRE VIRUS FULL-LENGTH M GENE

BACKGROUND OF THE INVENTION

Hantaviruses are considered Category A Priority Pathogens by the National Institute of Allergies and Infectious Disease. These viruses cause a spectrum of vascular-leak syndromes including hantavirus pulmonary syndrome (HPS) and hemorrhagic fever with renal syndrome (HFRS). Many HPS and HFRS hantaviruses pose a natural threat to persons working, living or traveling in endemic regions, including military personnel. There is one hantavirus (Andes virus) that has unique properties that make amenable to use as a biological weapon.

Andes virus (ANDV) and Sin Nombre virus (SNV) are the predominant causes of HPS in South and North America, respectively. These rodent-borne viruses were discovered in the early 1990's and have caused severe disease in several hundred persons.

Since the discovery of SNV in 1993, it has caused severe disease in ~500 persons in the United States and Canada, resulting in ~200 deaths (35% case-fatality rate). SNV is carried by the deer mouse and transmitted via inhalation or ingestion of contaminated secreta/excreta, or by rodent bite. Most of the fatalities occurred in previously healthy working-age males. HPS is a disease with rapid onset, and rapid progression from mild to severe disease (i.e., can occur over the weekend). The disease begins as an influenza-like illness including fever, headache, nausea, cough, and can progress rapidly to respiratory failure and cardiogenic shock. There is no specific therapeutic or vaccine to treat or prevent HPS. Hammerbeck, C. D., Wahl-Jensen, V., Hooper, J. W. Hantavirus. In: Vaccines for Biodefense and Emerging and Neglected Diseases (A. D. T. Barrett and L. R. Stanberry, Eds.), pp. 379-411. London: Academic Press, 2009; Jonsson C. B, J. Hooper, and G. Mertz (2008). Treatment of hantavirus pulmonary syndrome. Antiviral Res. Antiviral Res. 78:162-169.

There is no population with pre-existing immunity to SNV or ANDV and this virus is lethal in 35-40% of the people it infects. Note that this 35-40% case-fatality rate occurs despite treatment in modern intensive care units. All ages and both sexes are susceptible to ANDV and SNV. Most cases occur in previously healthy working-age males. The incubation period is approximately two weeks. Disease onset-to-death is rapid (over the weekend). In an animal model of HPS (Syrian hamsters), ANDV is highly lethal by all routes tested including the oral route. SNV is highly infectious (infectious dose 50% is 2 plaque forming units in Syrian hamsters but does cause lethal disease (Hooper et al., 2001). Thus, an infection model, rather than a lethal disease model, is used to evaluate medical countermeasures to prevent SNV infection.

New-World hantaviruses have been associated with outbreaks of a highly lethal disease, hantavirus pulmonary syndrome (HPS), in the Americas (reviewed in Schmaljohn and Hjelle, 1997, Emerg. Infect Dis. 3, 95-104). The disease is characterized by fever and vascular leakage resulting in non-cardiogenic pulmonary edema followed by shock. Case-fatality for HPS cuased by the most prevalent North American and South American hantaviruses, Sin Nombre virus (SNV) and Andes virus (ANDV), respectively is 30-50%.

Currently, there are four known hantaviruses associated with hemorrhagic fever with renal syndrome (HFRS): Hantaan virus (HTNV), Dobrava-Belgrade virus (DOBV), Puumala virus (PUUV), and Seoul virus (SEOV). Because distinct hantaviruses are usually carried by only one principal rodent host species, their distribution is generally limited to the range of that host (reviewed in Schmaljohn and Hjelle, 1997, Emerg. Infect. Dis. 3, 95-104). HTNV, carried by *Apodemus agrarius*, is found in Asia; DOBV, carried by *Apodemus flavicollis*, and PUUV, carried by *Clethrionomys glareolus*, are found in Europe. SEOV is more widely disseminated than any other recognized hantaviruses because its host, the common urban rat (Rattus norvegicus), is found throughout the world.

There is an alarming paucity of existing medical countermeasures to prevent or treat HPS. There is no vaccine against SNV, ANDY or any other HPS-associated hantavirus. Moreover, aside from basic research, there are no funded HPS vaccine development efforts. There is no specific drug to prevent or treat HPS. The treatment for HPS is extracorporeal membrane oxygenation therapy (ECMO) with costs as much as $500,000 per patient. Expertise at performing adult ECMO resides at only a few hospitals in the world. Thus, we are poorly prepared to deal with naturally occurring HPS cases (there have been ~2500 cases including ~500 in the US since 1993), or the use of hantaviruses as biological weapons.

Viruses in the Hantavirus genus (family Bunyaviridae) are enveloped and contain a genome comprised of three single-stranded RNA segments designated large (L), medium (M), and small (S) based on size (reviewed in Schmaljohn, 1996, In *The Bunyaviridae* Ed. R. M. Elliott. New York, Plenum Press p. 63-90). The hantavirus L segment encodes the RNA dependent RNA polymerase, M encodes two envelope glycoproteins (G1 and G2, also known as $G_n$ and $G_c$), and S encodes the nucleocapsid protein (N).

A number of inactivated HFRS vaccines derived from cell culture or rodent brain were developed and tested in Asia (Lee et al., 1990, *Arch. Virol., Suppl.* 1, 35-47; Song et al., 1992, *Vaccine* 10, 214-216; Lu et al., 1996, *J. Med. Virol.* 49, 333-335). Drawbacks of these traditional killed-virus vaccines include a requirement for appropriate containment for the growth and manipulation of virus, and the necessity to ensure complete inactivation of infectivity without destroying epitopes on the virion important for protective immunity. In order to overcome these drawbacks, vaccine approaches involving recombinant DNA technology were developed including: vaccinia-vectored vaccines (Schmaljohn et al. 1990, *J Virol.* 64, 3162-3170; Schmaljohn et al. 1992, *Vaccine* 10, 10-13; Xu et al. 1992, *Am. J. Trop. Med. Hyg.* 47, 397-404), protein subunit vaccines expressed in bacteria or insect cells (Schmaljohn et al. 1990, supra; Yoshimatsu et al., 1993, *Arch. Virol.* 130, 365-376; Lundkvist et al., 1996, *Virology* 216, 397-406), and a hepatitis core antigen-based recombinant vaccine (Ulrich et al., 1998, *Vaccine* 16, 272-280). For a review of hantavirus vaccine efforts see the review by Hooper and Li (Hooper and Li, 2001). ; Hammerbeck, C. D., Wahl-Jensen, V., Hooper, J.W. Hantavirus. In: Vaccines for Biodefense and Emerging and Neglected Diseases (A. D. T. Barrett and L. R. Stanberry, Eds.), pp. 379-411).

Vaccination with vaccinia recombinants expressing the M segment of either HTNV or SEOV elicited neutralizing antibodies and protected rodents against infection with both HTNV and SEOV, suggesting that an immune response to Gn-Gc alone can confer protection (Schmaljohn et al. 1990, supra; Xu et al. 1992, supra; Chu et al. 1995, *J. Virol.* 69, 6417-6423). Similarly, vaccination with Gn-Gc protein expressed in insect cells (baculovirus recombinant virus system) elicited neutralizing antibodies and protected hamsters from infection with HTNV (Schmaljohn et al. 1990, supra). In both the vaccinia and baculovirus systems, vaccination with Gn-Gc provided more complete protection than Gn or Gc alone (Schmaljohn et al. 1990, supra). There are reports that candidate DNA vaccines comprised of around 500 nucleotide stretches of the Sin Nombre virus (SNV) M gene, or the full-length S gene, are immunogenic in mice (Bharadwaj, et al., 1999, Vaccine 17, 2836,43) and conferred some protection against infection with SNV in a deer mouse infection model (Bharadwaj, et al., 2002, J. Gen. Virol. 83, 1745-1751). The protection was surmised to be cell-mediated because there was no convincing evidence that these constructs elicited a neutralizing, or otherwise protective, antibody response.

There have been several publications reporting the successful use of plasmid DNA vaccines containing the full-length M gene of SEOV, HTNV, ANDV, including the following reports:
1. Hooper, J. W., K. I. Kamrud, F. Elgh, D. Custer, and C. S. Schmaljohn (1999). DNA vaccination with hantavirus M segment elicits neutralizing antibodies and protects against Seoul virus infection. Virology, 255:269-278.
2. Hooper, J. W., D. Custer, E. Thompson, and C. S. Schmaljohn (2001). DNA Vaccination with the Hantaan virus M gene protects hamsters against three of four HFRS hantaviruses and elicits a high-titer neutralizing antibody response in rhesus monkeys. Journal of Virology 75:8469-8477.
3. Custer, D. M., E. Thompson, C. S. Schmaljohn, T. G. Ksiazek, and J. W. Hooper (2003). Active and passive vaccination against hantavirus pulmonary syndrome using Andes virus M genome segment-based DNA vaccine. Journal of Virology 79:9894:9905.
4. Hooper, J. W., D. M. Custer, J. Smith, and Victoria Wahl-Jensen. Hantaan/Andes virus DNA vaccine elicits a broadly cross-reactive neutralizing antibody response in nonhuman primates (2006). Virology 347:208-216.

In all cases high titer neutralizing antibodies were detected in animals (including nonhuman primates) vaccinated with the full-length M gene DNA vaccines, and protection from infection was achieved in rodent models. Neutralizing antibody responses to Gn-Gc in the aforementioned vaccine studies correlated with protection, suggesting that neutralizing antibodies not only play an important role in preventing hantavirus infection, but also might be sufficient to confer protection. Passive transfer of neutralizing monoclonal antibodies (MAbs) specific to either Gn or Gc protected hamsters against HTNV infection (Schmaljohn et al., 1990, supra; Arikawa et al., 1992, J. Gen. Virol. 70, 615-624), supporting the idea that neutralizing antibodies alone can confer protection. This is further supported by the finding that serum from nonhuman primates vaccinated using a gene gun with DNA vaccines containing the HTNV or ANDY full-length M genes protected hamsters from infection with HTNV or lethal disease caused by ANDY Custer, D. M., E. Thompson, C. S. Schmaljohn, T. G. Ksiazek, and J. W. Hooper (2003). Active and passive vaccination against hantavirus pulmonary syndrome using Andes virus M genome segment-based DNA vaccine. Journal of Virology 79:9894:9905). Similarly, sera from rabbits vaccinated with the ANDY M gene-based DNA vaccine using electroporation protected hamsters from a lethal challenge with ANDY (Hooper J. W., A. M. Ferro, and V. Wahl-Jensen. Immune Serum Produced by DNA Vaccination Protects Hamsters Against Lethal Respiratory Challenge with Andes Virus (2008). Journal of Virology 82:1332-1338.)

Hitherto, attempts to produce vaccines that produce neutralizing antibodies against SNV have been unsuccessful. For instance, Hjelle etal. (U.S. Pat. No. 6,316,250) attempted to vaccinate with the entire SNV Gn or fragments of G1 to generated antibodies. However, their vaccine did not produce high titer neutralizing antibodies. There are currently no serious efforts to develop an HPS vaccine anywhere in the world, including SNV vaccine. (refs 17, 18 below) NIH is currently funding a handful of academic laboratories working on hantavirus basic research.

The inventors have produced DNA vaccines against other hantaviruses including Seoul virus (SEOV), Hantaan virus, (HTNV) Puumala virus (PUUV) and Andes virus (ANDY) (refs 1, 5 and 6 below). There are a number of issued and pending patents related to these vaccines (refs 23-26 below). SEOV, HTNV, and PUUV cause hemorrhagic fever with renal syndrome (HFRS). All of these DNA vaccines are based on the full-length M gene open reading frame that encodes the Gn and Gc proteins, and all of these DNA vaccines elicit neutralizing antibodies in animal models. Neutralizing antibodies produced by DNA vaccination have been shown to protect against infection and disease in passive transfer studies (refs 3,4 below). In addition, the Hantaan and Puumala DNA vaccines have been tested in a phase 1 clinical trial (ongoing). The immunogenicity data generated in this phase 1 trial demonstrates that DNA vaccines against hantaviruses were capable of eliciting neutralizing antibodies in humans. This was the first time hantavirus neutralizing antibodies have been produced in humans using plasmid DNA. The overall seroconversion rate in this phase 1 trial was 43% (12 of 28). One of the most notable findings was that very high titers of neutralizing antibodies were achievable. Two of the peak anti-Hantaan virus titers were >1,000 and four of the peak anti-Puumala virus titers were >1,000. Neutralizing antibody titers as high as 10,240 were achieved for both Hantaan virus and Puumala virus.

The antibody response elicited by the hantavirus M gene-based DNA vaccines have been shown to cross-neutralize some, but not other hantaviruses. For example, the HTNV DNA vaccine was shown to elicit neutralizing antibodies against Seoul virus and Dobrava virus (a major cause of HFRS in the Balkans)(ref 1 below). In some cases the cross-neutralizing antibody response is produced in certain species using certain delivery technologies, but not others. This was the case with our ANDV DNA vaccine. When nonhuman primates were vaccinated with the ANDV DNA vaccine using a gene gun the sera contained antibodies that not only neutralized ANDV but also neutralized SNV and Black Creek Canal virus (ref. 3 below). Based on those results we concluded that the development of a SNV-specific DNA vaccine was unnecessary. However, recently we found that when rabbits were vaccinated with the ANDY DNA vaccine using muscle electroporation the sera was unable to neutralize SNV despite exhibiting very high titer ANDY-neutralizing activity (ref 4 below). It is speculated that this could be due to antibody specificity differences, antibody avidity differences, or antibody isotype differences.

This finding prompted us to reinitiate the development of a SNV M gene-based DNA vaccine rather than depend on the ANDV DNA vaccine to cross-protect against SNV.

The inventor is named as an inventor on other U.S. patents and publications, related to vaccines for hantaviruses and poxviruses, namely U.S. Pat. Nos. 6,451,309; 6,620,412; 6,562,376, 7,217,812, and U.S Patent application publication US-2010-03203024 A1. The entire contents of these patents are incorporated herein by reference.

SUMMARY OF THE INVENTION

Key to the invention is a novel synthetic, codon-optimized Sin Nombre virus full-length M gene open reading frame (ORF). To date, there are no reports of a full-length M gene, or SNV M gene ORF, being successfully engineered into a DNA vaccine plasmid or other mammalian expression vector.

This SNV M gene DNA sequence has been altered (or optimized) in such a way as to increase the stability of the mRNA and to, theoretically, eliminate sequences that destabilize the plasmid in E. col. In addition, four amino acids that were unique to our full-length clone were changed to consensus amino acids based on alignments with five hantavirus M gene seuquences from GeneBank. The ORF nucleic acid sequence was changed without altering the coded amino acid sequence of the Sin Nombre M gene product, other than the four aforementioned amino acids. This was accomplished by codon optimizing the ORF. The process of codon optimization not only changed the nucleic sequence, but also it was intended to allow more efficient codon usage and increased stability of the mRNA produced by the plasmid. An algorithm called GeneOptimizer (patent pending), owned by GeneArt was used to allow more efficient codon usage and stabilization of the mRNA. It is noted that, while the ORF was codon optimized, the flanking sequence was unchanged.

This synthetic M gene has been engineered into a plasmid-based vaccine system, (i.e, pWRG/SN-M(opt)), and is believed could be subcloned into a virus-vectored vaccine. The preferred DNA plasmid containing this sequence is designated pWRG/SN-M(opt), and its DNA sequence is described in detail below. pWRG/SN-M(opt) is capable of eliciting good neutralizing antibody responses against Sin Nombre virus. In fact, pWRG/SN-M(opt), as a DNA vaccine delivered by gene gun, is the first vaccine of any kind that has elicited convincing levels of neutralizing antibodies against Sin Nombre virus in animals.

The development of this novel SNV full-length M segment and its use as a vaccine can be summarized as follows. As mentioned above, it had been hoped that an Andes virus M gene-based DNA vaccine would cross—neutralize with the other HPS virus, Sin Nombre virus. In fact, early results gave indication that this would be the case. When nonhuman primates were vaccinated with the ANDY DNA vaccine using a gene gun the sera contained antibodies that not only neutralized ANDY but also neutralized SNV and Black Creek Canal virus (6). Based on those results the inventor concluded that the development of a SNV-specific DNA vaccine was unnecessary. However, recently the inventor found that when rabbits were vaccinated with the ANDY DNA vaccine using muscle electroporation the sera was unable to neutralize SNV despite exhibiting very high titer ANDV-neutralizing activity (11). The data is published in Hooper J. W., A. M. Ferro, and V. Wahl-Jensen. Immune Serum Produced by DNA Vaccination Protects Hamsters Against Lethal Respiratory Challenge with Andes Virus (2008). Journal of Virology 82:1332-1338. The inventor realized that the ANDV DNA vaccine would not be suitable as a vaccine to cross-protect against SNV, so sought a vaccine specifically for SNV.

The inventor cloned the full-length M gene from SNV, strain CC107 into a DNA vaccine vector, producing a plasmid with an intact open reading frame—pWRG/SN-M(2a). pWRG/SNV-M(2a) was tested for immunogenicity in rabbits, and it was discovered that high-titer neutralizing antibodies were produced after 4 vaccinations. This represented the first time high-titer SNV neutralizing antibodies were ever produced by any vaccine.

However, it required more vaccinations than the inventor would have preferred, so pWRG/SNV-M(2a) was re-designed for optimization. It was found that the M gene sequence in pWRG/SNV-M(2a) produced amino acids that were unique to our clone (i.e., not in published GeneBank SNV M sequences). This is shown in the Table 1 below, by identifying possible cloning errors in pWRG/SN-M(2a) M gene ORF and determining consensus amino acid sequence. In Table 1, SN-M(2a) is the amino acid sequence of the SNV M open reading frame (ORF) cloned into pWRG/SN-M(2a). This sequence as aligned with several SNV M gene ORFs from Genebank: AAA68036 (SNV strain CC107), AAA68036 (SNV strain CC107 isolate 74), NP_941974 (SNV strain NMH10), 083887 (New York virus), AAC54561 (NY-2 virus), and AC54559 (Rhode Island 1 virus). The four amino acids so identified were changed to the consensus amino acids in the synthetic gene cloned into pWRG/SN-N (opt), see below.

These consensus amino acids were identified at these positions and then an optimized version of this gene was synthesized. Next, we cloned the synthetic M gene (SN-M(2a)) into a DNA vaccine vector and named the plasmid pWRG/SN-M (opt). This plasmid pWRG/SN-M(opt) was deposited on January 26, 2011 in the American Type Culture Collection, located at 10801 University Blvd.Manassas, Va. 20110. The deposit was made under the terms of the Budapest Treaty.

Table 2 shows the nucleic acid differences between the original cloned M gene (SN-M[2a]) and the optimized M gene (SN-M[opt]).

TABLE 1

The amino acid sequence encoded by the ORF cloned into pWRG/SN-M(2a) (SEQ ID NO: 15) was aligned with six SNV M sequences (SEQ ID NOS 16-21, respectively, in order of appearance) from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
SN-M(2a)     1   MVGWVCIFLVVLTTATAGLTRNLYELQIECPHTVGLGQGYVTGSVETTPILLTQVADLKI
AAA6800      1   ..............................K.............................
AAA68036     1   ..............................K.............................
NP_941974    1   ..............................K...................I.........
Q83887       1   .......S....A.T...............K...........................T....
AAC54561     1   ...F........A.T...............K..................G........T....
AAC54559     1   ............A.T...............K...........................T....
consensus    1   ***.***.****.*.************.*******************..********.****

SN-M (2a)   61   ESSCNFDLHVPATTTQKYNQVDWTKKSSTTESTNAGATTFEAKTKEVNLKGTCNIPPTTF
AAA6800     61   ............................................................
AAA68036    61   ............................................................
NP_941974   61   .........................................................I...
Q83887      61   ...........S.SI......E.A.........S..............S.........V...
```

TABLE 1-continued

The amino acid sequence encoded by the ORF cloned into pWRG/SN-M(2a) (SEQ ID NO: 15) was aligned with six SNV M sequences (SEQ ID NOS 16-21, respectively, in order of appearance) from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
AAC54561    61  ..........S.SI......E.A.........S..............S.........V...
AAC54559    61  ..........S.SI......E.A.........S..............S.........V...
consensus   61  **********.*..******.*.*********.*************..*********.***

SN-M(2a)   121  EAAYKSRKTVICYDLACNQTHCLPTVHLIAPVQTCMSVRSCMIGLLSSRIQVIYEKTYCV
AAA6800    121  ............................................................
AAA68036   121  ...F........................................................
NP_941974  121  ............................................................
Q83887     121  ............................................................
AAC54561   121  ............................................................
AAC54559   121  ....................Y.......................................
consensus  121  ***.********************.***********************************

SN-M(2a)   181  TGQLIEGLCFIPTHTIALTQPGHTYDTMTLPVTCFLVAKKLGTQLKLAVELEKLITGVSC
AAA6800    181  ............................................................
AAA68036   181  ............................................................
NP_941974  181  ............................................................
Q83887     181  ....V......................I.............I.........ASG.
AAC54561   181  ....V......................I.............I.........ASG.
AAC54559   181  ....V......................I.............I.........ASG.
consensus  181  ****.**********************.*************.*********...*

SN-M(2a)   241  AENSFQGYYICFIGKHSEPLFVPTMEDYRSAELFTRMVLNPRGEDHDPDQNGQGLMRIAG
AAA6800    241  T...........................................................
AAA68036   241  T...........................................................
NP_941974  241  T...........................................................
Q83887     241  T...........L.........M.D...................................
AAC54561   241  T...........L.........M.D...................................
AAC54559   241  T...........L.......S..M.D..................................
consensus  241  .***********.*******.**.*.**********************************

SN-M(2a)   301  PVTAKVPSTETTETMQGIAFAGAPMYSSFSTLVRKADPEYVFSPGIIAESNHSVCDKKTV
AAA6800    301  ............................................................
AAA68036   301  ............................................................
NP_941974  301  ............................................................
Q83887     301  .I........................D....................I
AAC54561   301  .I.........A..............D....................I
AAC54559   301  .I...............T........D....................AI
consensus  301  *.**********.*************.*******************..

SN-M(2a)   361  PLTWTGFLAVSGEIERITGCTVFCTLAGPGASCEAYSETGIFNISSPTCLVNKVQKFRGS
AAA6800    361  ............................................................
AAA68036   361  ............................................................
NP_941974  361  ..............K.............................................
Q83887     361  ..............K.........V...................................
AAC54561   361  ..............K.........V...................................
AAC54559   361  ..............K.........V.....K.............................
consensus  361  **************.*********.******.*****************************

SN-M(2a)   421  EQRINFMCQRVDQGVVVYCNGQKKVILTKTLVIGQCIYTFTSLFSLIPGVAHSLAVELCV
AAA6800    421  .............D..............................................
AAA68036   421  .............D..............................................
NP_941974  421  .............D..............................................
Q83887     421  .............D.I............................................
AAC54561   421  .............D.I............................................
AAC54559   421  .............D.I............................................
consensus  421  *************.*.*********************************************

SN-M(2a)   481  PGLHGWATTALLITFCFGWLLIPTVTLIILKILRLLTFPCSHYSTESKFKVILERVKVEY
AAA6800    481  .....................................S.....................
AAA68036   481  .....................................S.....................
NP_941974  481  ..............A.......................S.....................
Q83887     481  ...................I.M...............S.........A...........
AAC54561   481  ...................I.M...............S.........A...........
AAC54559   481  ........A..........I.M...............S.........A...........
consensus  481  ********.*********.*.*.*************.*********.*************

SN-M(2a)   541  QKTMGSMVCDICHHECETAKELETHKKSCPEGQCPYCMTITESTESALQAHFSICKLTNR
AAA6800    541  ............................................................
AAA68036   541  ............................................................
```

TABLE 1-continued

The amino acid sequence encoded by the ORF cloned into pWRG/SN-M(2a) (SEQ ID NO: 15) was aligned with six SNV M sequences (SEQ ID NOS 16-21, respectively, in order of appearance) from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
NP_941974   541 ......................................A.......
Q83887      541 .........V..........................M........
AAC54561    541 .........V..........................M........
AAC54559    541 .........A..........................M........L.........
consensus   541 *********.*************************.********.***.*******

SN-M(2a)    601 FQENLKKSLKRPEVRKGCYRTLGVFRYKSRCYVGLVWGILLTTELIIWAASADTPLMESG
AAA6800     601 ...I........................................................
AAA68036    601 ...I........................................................
NP_941974   601 ............................................................
Q83887      601 .............KQ.......................V........V...........
AAC54561    601 .............KQ.......................V........V...........
AAC54559    601 .............KQ.R.....................V........V...........
consensus   601 ***.**********..*.*********************.*******.************

SN-M(2a)    661 WSDTAHGVGIVPMKTDLELDFALASSSSYSYRRKLVNPANQEETLPFHFQLDKQVVHAEI
AAA6800     661 ............................................................
AAA68036    661 ............................................................
NP_941974   661 ..........I.................................................
Q83887      661 .............................................K.............
AAC54561    661 ............................................D...K..........
AAC54559    661 .............................................K.............
consensus   661 **********.*************************.***.*******************

SN-M (2a)   721 QNLGHWMDGTFNIKTAFHCYGECKKYAYPWQTAKCFFEKDYQYETSWGCNPPDCPGVGTG
AAA6800     721 ............................................................
AAA68036    721 ............................................................
NP_941974   721 ............................................................
Q83887      721 ............................................................
AAC54561    721 ............................................................
AAC54559    721 ............................................................
consensus   721 ************************************************************

SN-M (2a)   781 CTACGVYLDKLRSVGKAYKIVSLKYTRKVCIQLGTEQTCKHIDVNDCLVTPSVKVCMIGT
AAA6800     781 ............................................................
AAA68036    781 ............................................................
NP_941974   781 ............................................................
Q83887      781 ..................F..............................L...
AAC54561    781 ..................F..............................L...
AAC54559    781 ..........G.......F..............................L...
consensus   781 *************.**********.***********************.***

SN-M (2a)   841 ISKLQPGDTLLFLGPLEQGGIILKQWCTTSCVFGDPGDIMSTTSGMRCPEHTGSFRKICG
AAA6800     841 ............................................................
AAA68036    841 ............................................................
NP_941974   841 ............................................................
Q83887      841 .............................................T..K.........
AAC54561    841 .............................................T..K.........
AAC54559    841 .............................................T..K.........
consensus   841 *********************************************.**.*********

SN-M (2a)   901 FATTPTCEYQGNTVSGFQRMMATRDSFQSFNVTEPHITSNRLEWIDPDSSIKDHINMVLN
AAA6800     901 ............................................................
AAA68036    901 ............................................................
NP_941974   901 ............................................................
Q83887      901 ...........I................................................
AAC54561    901 ...........I................................................
AAC54559    901 ...........I................................................
consensus   901 ***********.************************************************

SN-M (2a)   961 RDVSFQDLSDNPCKVDLHTQSIDGAWGSGVGFTLVCTVGLTECANFITSIKACDSAMCYG
AAA6800     961 ............................................................
AAA68036    961 ............................................................
NP_941974   961 ............................................................
Q83887      961 ............................................................
AAC54561    961 ............................................................
AAC54559    961 ............................................................
consensus   961 ************************************************************
```

TABLE 1-continued

The amino acid sequence encoded by the ORF cloned into pWRG/SN-M(2a) (SEQ ID NO: 15) was aligned with six SNV M sequences (SEQ ID NOS 16-21, respectively, in order of appearance) from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
SN-M(2a)   1021 ATVTNLLRGSNTVKVVGKGGHSGSLFKCCHDTDCTEEGLAASPPELDRVTGYNQIDSDKV
AAA6800    1021 ............................................................
AAA68036   1021 ............................................................
NP_941974  1021 ............................................................
Q83887     1021 ............................................................
AAC54561   1021 ............................................................
AAC54559   1021 ....................S.......................................
consensus  1021 ********************.***************************************

SN-M(2a)   1081 YDDGAPPCTIKCWFTKSGEWLLGILNGNWVVVAVLIVILILSILLFSFFCPVRNRKNKAN
AAA6800    1081 ..............R.............................................
AAA68036   1081 ............................................................
NP_941974  1081 .......................................................S....
Q83887     1081 .....................................................I.G....S.
AAC54561   1081 .....................................................I.G....S.
AAC54559   1081 .....................................................I.G....S.
consensus  1081 **************.*****************************************.*.****.*
```

TABLE 2

The sequence starts at the Not 1 site and ends at the BstB1 or BglII site depending on the construct (BstB1 for SN-M(2a) and BglII for SN-M(opt)) (SEQ ID NO: 2).

```
SN-M(2a)    1 GCGGCCGCGGATCTGCAGGAATTCGGCACGAGAGTAGTAGACTCCGCACGAAGAAGCAAA
SN-M(opt)   1 ............................................................

SN-M(2a)   61 CACTGAATAAAGGATATACAGAATGGTAGGGTGGGTTTGCATCTTCCTCGTGGTCCTTAC
SN-M(opt)  61 .........................G..C.....G...........G.....G..G..

SN-M(2a)  121 TACTGCAACTGCTGGATTGACACGGAATCTCTATGAATTACAGATAGAATGTCCACATAC
SN-M(opt) 121 C..C...C...A..C..CC.....C.....C..G..C..GC.GA.....C...G..C...C..C..

SN-M(2a)  181 TGTGGGTCTAGGTCAAGGTTATGTGACAGGTTCTGTAGAAACTACACCTATTCTCTTAAC
SN-M(opt) 181 C.....C...G..C..G..C..C.....CAGC..G..G..A..C...C..C..GC.G..

SN-M(2a)  241 ACAGGTAGCTGACCTCAAGATTGAGAGTTCTTGCAATTTTGACTTGCATGTCCCAGCCAC
SN-M(opt) 241 C.....G..C.....G...........CAGC.....C...C....C...C..G..C.....

SN-M(2a)  301 TACTACTCAGAAATACAATCAAGTTGACTGGACTAAAAAAGTTCTACTACAGAAAGCAC
SN-M(opt) 301 C..C...C...........C..G..G.........C..G..G..CAGC..C...C..G.....

SN-M(2a)  361 GAATGCAGGTGCAACTACATTTGAGGCTAAAACAAAGAGGTAAATTTAAAAGGCACATG
SN-M(opt) 361 C..C...C..A..C..C..C..C.....C..G..C.....A..G..CC.G..G.....C...

SN-M(2a)  421 TAATATTCCTCCAACTACGTTTGAGGCTGCATACAAGTCAAGGAAGACAGTGATTTGTTA
SN-M(opt) 421 C..C...C..C..C...C..A........C..C......AGC..A.....C......C..C..

SN-M(2a)  481 TGATTTGGCCTGTAATCAAACACATTGTCTTCCTACAGTCCATCTGATTGCTCCTGTTCA
SN-M(opt) 481 C..CC.......C...C..G..C...C...C...G..C...C...G..C.....C..C..G...

SN-M(2a)  541 AACATGTATGTCTGTACGGAGCTGTATGATAGGTCTGTTATCTAGCAGGATCCAGGTTAT
SN-M(opt) 541 G..C...C...AGC..G.........C...C...C.....C.G..C....C...........G...

SN-M(2a)  601 CTACGAGAAGACATATTGTGTCACGGGTCAGTTAATAGAAGGGCTATGTTTCATTCCAAC
SN-M(opt) 601 .........A..C...C...C..G..C...C.....C.G..C...G..C...G..C.....C..C..

SN-M(2a)  661 ACATACAATTGCACTTACACAGCCTGGTCATACTTATGATACTATGACATTGCCTGTGAC
SN-M(opt) 661 C..C.....C...C..G..C.....C...C...C...C...C...C......CC....C.....

SN-M(2a)  721 TTGTTTTTTAGTAGCCAAAAAGTTGGGGACGCAGCTTAAGCTGGCTGTTGAGTTAGAGAA
SN-M(opt) 721 C..C....C.G..G.....G....C.....C..C.....G..........C..G...C.G..A...

SN-M(2a)  781 ATTGATTACTGGTGTGAGCTGCGCAGAGAATAGCTTCCAAGGTTATTACATCTGTTTTAT
SN-M(opt) 781 GC.....C...C...C.........A..C.....C.........G..C..C..........C..C..
```

TABLE 2-continued

The sequence starts at the Not 1 site and ends at the BstB1 or BglII site depending on the construct (BstB1 for SN-M(2a) and BglII for SN-M(opt)) (SEQ ID NO: 2).

```
SN-M(2a)   841 TGGAAAACATTCAGAGCCCTTATTTGTACCAACAATGGAAGATTATAGATCAGCTGAGTT
SN-M(opt)  841 C..C..G..CAGC......C.G..C..G..C...C............C...AGC..C...C.

SN-M(2a)   901 ATTTACTCGTATGGTTTTAAATCCAAGAGGTGAAGATCATGACCCTGATCAAAATGGACA
SN-M(opt)  901 G..C..C..G.....GC.G..C..C..G..C..G..C..C.....C..C..G..C..C...

SN-M(2a)   961 AGGGTTGATGAGAATAGCTGGACCTGTTACTGCCAAGGTACCATCTACAGAAACGACTGA
SN-M(opt)  961 G..CC.....C.G..C..C.....C..G..C........G..CAGC..C..G..A..C..

SN-M(2a)  1021 AACAATGCAAGGAATTGCATTTGCTGGGGCACCAATGTATAGTTCATTCTCAACTCTTGT
SN-M(opt) 1021 ...C.....G..C.....C..C..C..A..C..C.....C..CAGC...AGC..C..G..

SN-M(2a)  1081 GAGAAAAGCTGATCCTGAATATGTCTTTTCTCCAGGTATAATTGCAGAATCAAATCATAG
SN-M(opt) 1081 .C.G..G..C..C..C..G..C..G..CAGC..C..C..C.....C..GAGC..C..C..

SN-M(2a)  1141 TGTTTGTGATAAAAAGACAGTGCCCCTAACATGGACTGGGTTTCTAGCAGTTTCAGGAGA
SN-M(opt) 1141 C..G..C..C..G..A..C........G..C.....C..C..C..G..C..GAGC..C...

SN-M(2a)  1201 GATAGAAAGGATAACAGGCTGTACAGTTTTCTGTACATTGGCTGGACCTGGTGCCAGTTG
SN-M(opt) 1201 ...C..GC.....C..C.....C..C..G.....C..CC.....C.........C.....C..

SN-M(2a)  1261 TGAAGCATACTCAGAAACAGGAATCTTCAACATAAGCTCCCCAACTTGCTTGGTAAATAA
SN-M(opt) 1261 C..G..C...AGC..G.....C...........C....AG..C..C...C..G..C..

SN-M(2a)  1321 AGTCCAAAAATTTAGAGGTTCAGAACAAAGAATTAATTTTATGTGTCAAAGGGTTGATCA
SN-M(opt) 1321 G..G..G..C..CC.G..CAGC..G..GC.G..C..C..C.....C..GC....G..C..

SN-M(2a)  1381 AGGTGTTGTGGTTTACTGTAATGGACAGAAGAAAGTCATTCTTACCAAAACCCTAGTAAT
SN-M(opt) 1381 G.AC..G.....G.....C..C..C.....A.....G..C..G.....G.....G..G...

SN-M(2a)  1441 AGGTCAATGTATCTACACATTTACTAGTCTGTTTTCACTGATCCCTGGAGTTGCTCATTC
SN-M(opt) 1441 C..C..G..C.........C..C..C..C.....CAGC............C..G......AG SN-M(2a)  1501 CCTTGCTGTGGAGTTATGTGTTCCAGGTCTTCATGGCTGGGCTACAACAGCACTACTTAT
SN-M(opt) 1501 ...G..A..C..AC.G..C..G..T..C..G..C..A.....C..C..C..C..G..G...

SN-M(2a)  1561 TACTTTCTGCTTTGGCTGGCTTCTCATACCAACAGTTACTTTAATTATACTAAAAATCTT
SN-M(opt) 1561 C..C........C........G..G..C..C.....G..CC.G..C..C..G..G...C.

SN-M(2a)  1621 AAGGCTATTGACCTTCCCATGCTCGCACTATTCTACAGAATCAAAATTCAAAGTCATTTT
SN-M(opt) 1621 GC.....GC........AGC...AGC.....CAGC..C..G..C..G.........G...C.

SN-M(2a)  1681 AGAAAGAGTCAAGGTGGAGTATCAAAAGACAATGGGTTCAATGGTGTGTGACATTTGTCA
SN-M(opt) 1681 G...C.C..G...........C..G..A...C.....CAGC......C......C..C..

SN-M(2a)  1741 CCATGAATGTGAGACGGCAAAAGAGCTCGAAACACATAAGAAAAGTTGCCCAGAAGGTCA
SN-M(opt) 1741 ...C..G..C.....A..C........G.....C..C.....G..C.....C..G..C..

SN-M(2a)  1801 ATGCCCATACTGCATGACAATAACTGAGTCCACTGAGAGTGCATTACAAGCTCATTTTTC
SN-M(opt) 1801 G.....C...........C..C..A...AG...C.....C..CC.G..G..C..C..CAG SN-M(2a)  1861 AATCTGTAAGCTAACGAACAGGTTCCAGGAAAATCTAAAAAAATCATTAAAACGTCCAGA
SN-M(opt) 1861 C.....C.....G..C...C............C..G..G..GAGCC.G..G..G..C..

SN-M(2a)  1921 AGTAAGGAAAGGTTGTTACAGGACATTAGGAGTATTCCGCTACAAGAGCAGGTGCTATGT
SN-M(opt) 1921 ...GC....G..C..C.....C....CC.G..C..G.....G.........C...........

SN-M(2a)  1981 TGGCTTAGTATGGGGGATCCTCTTGACGACAGAGCTGATTATATGGGCTGCTAGTGCAGA
SN-M(opt) 1981 G...C.G..G.....C..T..GC.....C.........C..C.....C..C..C..C..

SN-M(2a)  2041 TACCCCTCTAATGGAGTCTGGTTGGTCAGATACAGCACATGGTGTAGGTATAGTCCCTAT
SN-M(opt) 2041 C.....C..G.....AAGC..G...AGC..C..C..T.....C..G..A..C..G..C..

SN-M(2a)  2101 GAAAACAGATTTAGAGCTTGACTTTGCCTTGGCCTCATCATCTTCTTATAGTTATAGAAG
SN-M(opt) 2101 ......C..CC.G..A..G.....C....C.....AGCAGCAGCAGC..C..C..CC.GC.

SN-M(2a)  2161 AAAGCTTGTAAACCCTGCCAATCAAGAGGAGACACTCCCTTTTCATTTCCAGTTAGATAA
SN-M(opt) 2161 G.....G..G.....C.....C..G..A........G..C..C..C.....AC.G..C..

SN-M(2a)  2221 GCAAGTAGTGCATGCAGAAATACAGAACCTAGGGCATTGGATGGATGGCACATTCAACAT
SN-M(opt) 2221 ...G..G.....C..C..G..C........G..C..C........C.....C.....T..

SN-M(2a)  2281 AAAGACTGCTTTCCATTGCTATGGAGAATGTAAAAAATATGCCTATCCTTGGCAGACAGC
SN-M(opt) 2281 C.....C..C.....C.....C..C..C..G..C..G..G..C.....C..C.........C..
```

TABLE 2-continued

The sequence starts at the Not 1 site and ends at the BstB1 or BglII site depending on the construct (BstB1 for SN-M(2a) and BglII for SN-M(opt)) (SEQ ID NO: 2).

```
SN-M(2a)   2341 CAAGTGTTTCTTTGAAAAAGATTATCAGTATGAAACAAGCTGGGGCTGTAACCCACCAGA
SN-M(opt)  2341 ......C.....C...G..G..C..C.....C..G.............C.....C..C..

SN-M(2a)   2401 TTGCCCAGGAGTAGGGACAGGTTGTACAGCCTGTGGGGTATACTTAGACAAGCTCCGTTC
SN-M(opt)  2401 C..T..T..C..G..C..C..C.....C.....C..C..G...C.G........G..GAG SN-M(2a)   2461 AGTTGGGAAAGCCTATAAAATTGTATCACTCAAATACACGCGAAAGGTGTGTATTCAATT
SN-M(opt)  2461 C..G..C..G.....C..G..C..G..C..G..G.....C..G..A.....C..C..GC.

SN-M(2a)   2521 GGGGACAGAACAAACCTGTAAACATATAGATGTTAATGATTGTTTGGTCACCCCGTCTGT
SN-M(opt)  2521 ...C.....G..G..A..C..G..C..C..C..G..C.....CC....G.....CAGC..

SN-M(2a)   2581 TAAAGTTTGCATGATAGGTACCATCTCGAAGCTTCAGCCAGGTGACACCTTATTGTTTTT
SN-M(opt)  2581 G.....C..T.....T..C.......AGC.....G.....C..C..T...C.GC....CC.

SN-M(2a)   2641 GGGCCCTTTAGAGCAAGGTGGGATTATTCTAAAACAATGGTGCACAACATCATGTGTGTT
SN-M(opt)  2641 ......CC.G..A...G..C..C..C.....G..G..G.....T..C..C..C..C.....

SN-M(2a)   2701 TGGAGACCCTGGTGATATCATGTCAACAACAAGTGGGATGAGATGCCCTGAGCACACAGG
SN-M(opt)  2701 C..C.....C..C..C......AGC..C..CTCC..C...C.G.....C........C...

SN-M(2a)   2761 GTCTTTTAGAAAAATCTGTGGATTTGCTACAACACCTACATGTGAATATCAAGGTAATAC
SN-M(opt)  2761 CAGC..CC.G...G..T.....C..C..C..C..C.....C..C..G..C..G..C..C..

SN-M(2a)   2821 AGTGTCTGGATTCCAACGCATGATGGCAACTCGAGATTCTTTTCAATCATTCAATGTGAC
SN-M(opt)  2821 C.....C..C.....G..G........C..C..G...AGC..C..GAGC.....C.....

SN-M(2a)   2881 AGAACCACATATTACCAGCAATCGACTGGAATGGATTGATCCAGATAGTAGTATTAAAGA
SN-M(opt)  2881 C..G..C..C..C........C..G............C..C..C..C..C..C..C..G..

SN-M(2a)   2941 CCATATCAACATGGTTTTGAATAGAGATGTTTCCTTCCAAGATCTAAGTGATAATCCATG
SN-M(opt)  2941 ...C..........GC.C...C.G..C..GAG......G..C..G..C..C..C..C...

SN-M(2a)   3001 TAAGGTTGATTTGCATACACAATCTATTGATGGGGCTTGGGGATCAGGAGTGGGCTTTAC
SN-M(opt)  3001 C.....G..CC....C..C..GAGC..C..C..C..C.....CAGC..C.........C..

SN-M(2a)   3061 ATTAGTATGTACTGTAGGTCTTACAGAGTGTGCAAATTTCATAACTTCAATTAAGGCGTG
SN-M(opt)  3061 .C.G..G..C..A..G..C..G..C.....C..C..C.....C..C..C..C.....C..

SN-M(2a)   3121 TGATTCTGCTATGTGTTATGGGGCCACAGTTACAAATCTACTCAGAGGGTCTAACACAGT
SN-M(opt)  3121 C..CAGC..C.....C..C..C.....C..G..C..C..G..GC.G..C..C........

SN-M(2a)   3181 TAAAGTTGTCGGTAAAGGTGGGCATTCTGGGTCCTTGTTCAAGTGCTGCCATGATACTGA
SN-M(opt)  3181 G..G..G..G..C..G..C..C..CAGC..CAG.C....T............C..C..C..

SN-M(2a)   3241 CTGTACTGAAGAAGGTTTAGCAGCATCACCACCTCATTTAGATAGGGTTACTGGTTACAA
SN-M(opt)  3241 ...C..C..G.....CC.G..C..CAGC..C.....CC.G..C..A..G..C.....

SN-M(2a)   3301 TCAAATAGATTCTGATAAGGTTTATGATGACGGTGCACCGCCCTGTACAATTAAATGTTG
SN-M(opt)  3301 C..G..C..CAGC..C.....G..C..C..T..C..C..T.....C..C..C..G..C..

SN-M(2a)   3361 GTTCACAAAGTCAGGTGAGTGGTTGCTAGGAATTCTTAATGGCAATTGGGTAGTAGTTGC
SN-M(opt)  3361 ......C...AGC..C.....C....G..C..C..G..C.....C.....C..C..G...

SN-M(2a)   3421 TGTTTTGATTGTAATTTTGATACTATCAATACTCCTGTTCAGCTTCTTTTGTCCTGTTAG
SN-M(opt)  3421 C..GC....C..G..CC....C..G..T..C..G.............C..C..C..GC.

SN-M(2a)   3481 AAATAGAAAAAATAAGGCCAATTAGCAAACATATATGTAAGTAAGGGTATGATCATATTA
SN-M(opt)  3481 G..CC.G..G..C.......C......................................

SN-M(2a)   3541 TATCATTATGCGTATACTCTTATATCTATAATATCTATGTATCCTTATACTCTAACTATT
SN-M(opt)  3541 ............................................................

SN-M(2a)   3601 TATATTAATTTTTACTTTTATACAAGTATTAACTAACCCATTACCAGCTAAAAAAACAA
SN-M(opt)  3601 ............................................................

SN-M(2a)   3661 ACCCTTAACACCTATATAATCCCATTTGCTTATTACGAGGCTTTTGTTCCTGCGGAGTCT
SN-M(opt)  3661 ............................................................

SN-M(2a)   3721 ACTACTATTCGAA
SN-M(opt)  3721 .......AGATCT
```

This new SNV vaccine was tested for a capacity to elicit neutralzing antibodies by vaccinating rabbits with the pWRG/SN-M(opt) using muscle electroporation. Very high titers of SNV neutralizing antibodies were produced after only a single vaccination.

The term "antibody" is art-recognized terminology and is intended to include molecules or active fragments of molecules that bind to known antigens. These active fragments can be derived from an antibody of the present invention by a number of techniques. For further description of general techniques for the isolation of active fragments of antibodies, see for example, Khaw, B. A. et al. *J. Nucl. Med.* 23:1011-1019 (1982). The term "antibody" also includes bispecific and chimeric antibodies and antibodies in nonmammalian species.

By neutralizing antibodies, or NAb, it is meant an antibody which defends a cell from an antigen or infectious body by inhibiting or neutralizing any effect it has biologically. For instance, a neutralizing antibody for SNV is an antibody which can inhibit or reduce the biological effects of SNV infection, that is, it binds to the virus and interferes with its ability to infect a cell.

By "high titer" it is meant meant neutralizing anibody titers similar to those produced in individuals that were infected with the virus and survived. As described in greater detail in the examples, the present inventors have found that serum from a vaccinee immunized with a DNA vaccine comprising the M segment of Sin Nombre virus contains antibodies able to neutralize Sin Nombre virus.

As used herein the term "immunogenically active" designates the ability to stimulate an immune response, i.e., to stimulate the production of antibodies, particularly humoral antibodies, or to stimulate a cell-mediated response. For example, the ability to stimulate the production of circulating or secretory antibodies or the production of a cell-mediated response in local mucosal regions, (e.g., intestinal mucosa), peripheral blood, cerebral spinal fluid or the like. The effective immunizing amount of the immunogenically active component(s) of this invention may vary and may be any amount sufficient to evoke an immune response and provide immunological protection against Sin Nombre virus infection. Amounts where a dosage unit comprises at least about 5 micrograms to about 5 milligrams of plasmid DNA are contemplated. At least one dosage unit per patient is contemplated herein as a vaccination regimen. In some embodiments, two or more dosage units may be especially useful. The skilled artisan will quickly recognize that a particular quantity of vaccine composition per dosage unit, as well as the total number of dosage units per vaccination regimen, may be optimized, so long as an effective immunizing amount of the virus or a component thereof is ultimately delivered to the animal.

We next combined the SNV DNA vaccine with an Andes virus construct, pWRG/AND-M, and a mixture of the two plasmids was used to vaccinate rabbits using muscle electroporation. High titer neutralizing antibodies against both SNV and ANDV were produced after 1 or 2 vaccinations. The SNV neutralizing activity was especially potent (titers >10,000 after 1 vaccination). Thus, the combination of the pWRG/SN-M(opt) DNA vaccine and pWRG/AND-M DNA vaccine effectively elicited high-titer neutralizing antibodies against the most prevalent and lethal hantavirus in North and South America. The novelty and potency of this SNV DNA vaccine and its utility in alone or in combination with other hantavirus DNA vaccine plasmids is a main focus of this application.

The amino acid one letter code is defined as the following: A=Alanine (Ala), I=Isoleucine (Ile), L=Leucine (Leu), M=Methionine (Met), F=Phenylalanine (Phe), P=Proline (Pro), W=Tryptophan (Trp), V=Valine (Val), N=Asparagine (Asn), C=Cysteine (Cys), Q=Glutamine (Q), G=Glycine (Gly), S=Serine (Ser), T=Threonine (Thr), Y=Tyrosine (Tyr), R=Arginine (Arg), H=Histidine (His), K=Lysine (Lys), D=Aspartic acid (Asp), and E=Glutamic acid (Glu).

As would be understood by someone having skill in this art, this invention covers sequences that are not necessarily physically derived from the nucleotide sequence itself, but may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use.

It is also understood in the art that certain changes to the nucleotide sequence employed in a genetic construct have little or no bearing on the proteins encoded by the construct, for example due to the degeneracy of the genetic code. Such changes result either from silent point mutations or point mutations that encode different amino acids that do not appreciably alter the behavior of the encoded protein. It is understood that portions of the coding region can be eliminated without affecting the ability of the construct to achieve the desired effect, namely induction of a protective immune response against Sin Nombre virus. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the M segment of Sin Nombre virus are equivalents within the scope of the present invention.

The DNA encoding the desired antigen can be introduced into the cell in any suitable form including, a linearized plasmid, a circular plasmid, a plasmid capable of replication, an episome, RNA, etc. Preferably, the gene is contained in a plasmid. In a particularly preferred embodiment, the plasmid is an expression vector, such as pWRG7077. In another embodiment, the DNA encoding the desired antigen can be introduced into virus-based vaccine vectors such as recombinant adenovirus, recombinant vesicular stomatitis virus, or alphavirus replicons. Individual expression vectors capable of expressing the genetic material can be produced using standard recombinant techniques.

This invention entails new recombinant SNV DNA sequences which are useful to elicit neutralizing antibodies against SNV. The DNA sequences include the codon-optimized full-length M segment [designated SN-M(opt)] (SEQ ID NO:1), the optimized ORF plus M gene flanking sequences (SEQ ID NO:2), and the optimized open reading frame (ORF) (SEQ ID NO:3).

Thus in one embodiment the invention entails an isolated nucleic acid sequence set forth in SEQ ID NO:1, which is as follows. The Sin Nombre virus M gene (optimized) open reading frame is underlined. The synthetic open reading frame and flanking sequence was cloned into the Not I, Bgl II site of pWRG7077 (published). The Not 1 cloning site (GCG-GCCGCGG) (SEQ ID NO:7) and the Bgl II cloning site (GATCT) (SEQ ID NO:8) are in bold. An extraneous sequence having the sequence "ATCTGCAGGAATTCG-GCACGAG" (SEQ ID NO:9) is in italics. The flanking sequences include 5' and 3' non-translated sequence from the SNV M genome segment, and a 24-base sequence (the extraneous sequence) between the Not I site and position +2 of the M gene (not +1 because the first nucleotide is missing). This sequence was found to be essential for expression of the Gn protein from the Hantaan virus and Seoul virus full-length M gene-based DNA vaccine plasmids, pWRG/HTN-M(x) and pWRG/SEO-M, respectably. (See U.S. Pat. No. 7,217,812) It is noted that experiments demonstrated that this 24-base sequence was not essential for expression of Gn from the Puumala M gene-based DNA vaccine plasmid or the Andes M gene-based DNA vaccine plasmid, but was retained in those constructs (See US Patent Application Publication No. 20100323024 and U.S. Pat. No. 7,217,812, respectively).

Two SNV M segment nontranslated regions are indicated by wavy underline, and are between the extraneous sequence and the beginning of the ORF, and between the end of the ORF and the Bgl II cloning site.

GGGGGGGGGGGGCGCTGAGGTCTGCCTCGTGAAGAAGGTGTTGCTGACTC

ATACCAGGCCTGAATCGCCCCATCATCCAGCCAGAAAGTGAGGGAGCCAC

GGTTGATGAGAGCTTTGTTGTAGGTGGACCAGTTGGTGATTTTGAACTTT

TGCTTTGCCACGGAACGGTCTGCGTTGTCGGGAAGATGCGTGATCTGATC

CTTCAACTCAGCAAAAGTTCGATTTATTCAACAAAGCCGCCGTCCCGTCA

AGTCAGCGTAATGCTCTGCCAGTGTTACAACCAATTAACCAATTCTGATT

AGAAAAACTCATCGAGCATCAAATGAAACTGCAATTTATTCATATCAGGA

TTATCAATACCATATTTTTGAAAAAGCCGTTTCTGTAATGAAGGAGAAAA

CTCACCGAGGCAGTTCCATAGGATGGCAAGATCCTGGTATCGGTCTGCGA

TTCCGACTCGTCCAACATCAATACAACCTATTAATTTCCCCTCGTCAAAA

ATAAGGTTATCAAGTGAGAAATCACCATGAGTGACGACTGAATCCGGTGA

GAATGGCAAAAGCTTATGCATTTCTTTCCAGACTTGTTCAACAGGCCAGC

CATTACGCTCGTCATCAAAATCACTCGCATCAACCAAACCGTTATTCATT

CGTGATTGCGCCTGAGCGAGACGAAATACGCGATCGCTGTTAAAAGGACA

ATTACAAACAGGAATCGAATGCAACCGGCGCAGGAACACTGCCAGCGCAT

CAACAATATTTTCACCTGAATCAGGATATTCTTCTAATACCTGGAATGCT

GTTTTCCCGGGGATCGCAGTGGTGAGTAACCATGCATCATCAGGAGTACG

GATAAAATGCTTGATGGTCGGAAGAGGCATAAATTCCGTCAGCCAGTTTA

GTCTGACCATCTCATCTGTAACATCATTGGCAACGCTACCTTTGCCATGT

TTCAGAAACAACTCTGGCGCATCGGGCTTCCCATACAATCGATAGATTGT

CGCACCTGATTGCCCGACATTATCGCGAGCCCATTTATACCCATATAAAT

CAGCATCCATGTTGGAATTTAATCGCGGCCTCGAGCAAGACGTTTCCCGT

TGAATATGGCTCATAACACCCCTTGTATTACTGTTTATGTAAGCAGACAG

TTTTATTGTTCATGATGATATATTTTTATCTTGTGCAATGTAACATCAGA

GATTTTGAGACACAACGTGGCTTTCCCCCCCCCCCGGCATGCCTGCAGG

TCGACAATATTGGCTATTGGCCATTGCATACGTTGTATCTATATCATAAT

ATGTACATTTATATTGGCTCATGTCCAATATGACCGCCATGTTGACATTG

ATTATTGACTAGTTATTAATAGTAATCAATTACGGGGTCATTAGTTCATA

GCCCATATATGGAGTTCCGCGTTACATAACTTACGGTAAATGGCCCGCCT

GGCTGACCGCCCAACGACCCCCGCCCATTGACGTCAATAATGACGTATGT

TCCCATAGTAACGCCAATAGGGACTTTCCATTGACGTCAATGGGTGGAGT

ATTTACGGTAAACTGCCCACTTGGCAGTACATCAAGTGTATCATATGCCA

AGTCCGCCCCCTATTGACGTCAATGACGGTAAATGGCCCGCCTGGCATTA

TGCCCAGTACATGACCTTACGGGACTTTCCTACTTGGCAGTACATCTACG

TATTAGTCATCGCTATTACCATGGTGATGCGGTTTTGGCAGTACACCAAT

GGGCGTGGATAGCGGTTTGACTCACGGGGATTTCCAAGTCTCCACCCCAT

TGACGTCAATGGGAGTTTGTTTTGGCACCAAAATCAACGGGACTTTCCAA

AATGTCGTAATAACCCCGCCCCGTTGACGCAAATGGGCGGTAGGCGTGTA

CGGTGGGAGGTCTATATAAGCAGAGCTCGTTTAGTGAACCGTCAGATCGC

CTGGAGACGCCATCCACGCTGTTTTGACCTCCATAGAAGACACCGGGACC

GATCCAGCCTCCGCGGCCGGGAACGGTGCATTGGAACGCGGATTCCCCGT

GCCAAGAGTGACGTAAGTACCGCCTATAGACTCTATAGGCACACCCCTTT

GGCTCTTATGCATGCTATACTGTTTTTGGCTTGGGGCCTATACACCCCCG

CTTCCTTATGCTATAGGTGATGGTATAGCTTAGCCTATAGGTGTGGGTTA

TTGACCATTATTGACCACTCCCCTATTGGTGACGATACTTTCCATTACTA

ATCCATAACATGGCTCTTTGCCACAACTATCTCTATTGGCTATATGCCAA

TACTCTGTCCTTCAGAGACTGACACGGACTCTGTATTTTTACAGGATGGG

GTCCCATTTATTATTTACAAATTCACATATACAACAACGCCGTCCCCCGT

GCCCGCAGTTTTTATTAAACATAGCGTGGGATCTCCACGCGAATCTCGGG

TACGTGTTCCGGACATGGGCTCTTCTCCGGTAGCGGCGGAGCTTCCACAT

CCGAGCCCTGGTCCCATGCCTCCAGCGGCTCATGGTCGCTCGGCAGCTCC

TTGCTCCTAACAGTGGAGGCCAGACTTAGGCACAGCACAATGCCCACCAC

CACCAGTGTGCCGCACAAGGCCGTGGCGGTAGGGTATGTGTCTGAAAATG

AGCTCGGAGATTGGGCTCGCACCGCTGACGCAGATGGAAGACTTAAGGCA

GCGGCAGAAGAAGATGCAGGCAGCTGAGTTGTTGTATTCTGATAAGAGTC

AGAGGTAACTCCCGTTGCGGTGCTGTTAACGGTGGAGGGCAGTGTAGTCT

GAGCAGTACTCGTTGCTGCCGCGCGCGCCACCAGACATAATAGCTGACAG

ACTAACAGACTGTTCCTTTCCATGGGTCTTTTCTGCAGTCACCGTCCAAG

CTT

GCGGCCGCGGATCTGCAGGAATTCGGCACGAGAGTAGTAGACTCCGCACG

AAGAAGCAAACACTGAATAAAGGATATACAGAATGGTGGGCTGGGTGTGC

ATCTTCCTGGTGGTGCTGACCACCGCCACAGCCGGCCTGACCCGGAACCT

GTACGAGCTGAAGATCGAGTGCCCCCACACCGTGGGCCTGGCCAGGGCT

ACGTGACCGGCAGCGTGGAGACAACCCCCATCCTGCTGACCCAGGTGGCC

GACCTGAAGATTGAGAGCAGCTGCAACTTCGACCTGCACGTGCCCGCCAC

CACCACCCAGAAATACAACCAGGTGGACTGGACCAAGAAGAGCAGCACCA

CCGAGAGCACCAACGCCGGAGCCACCACCTTCGAGGCCAAGACCAAAGAA

GTGAACCTGAAGGGCACCTGCAACATCCCCCCCACCACATTTGAGGCCGC

CTACAAGAGCAGAAAGACCGTGATCTGCTACGACCTGGCCTGCAACCAGA

CCCACTGCCTGCCCACCGTGCACCTGATCGCCCCCGTGCAGACCTGCATG

AGCGTGCGGAGCTGCATGATCGGCCTGCTGTCCAGCCGGATCCAGGTGAT

CTACGAGAAACCTACTGCGTGACCGGCCAGCTGATCGAGGGCCTGTGCT

TCATCCCCACCCACACAATCGCCCTGACCCAGCCCGGCCACACCTACGAC
ACCATGACCCTGCCCGTGACCTGCTTTCTGGTGGCCAAGAAGCTGGGCAC
CCAGCTGAAGCTGGCCGTGGAGCTGGAAAAGCTGATCACCGGCGTGAGCT
GCACCGAGAACAGCTTCCAGGGCTACTACATCTGCTTCATCGGCAAGCAC
AGCGAGCCCCTGTTCGTGCCCACCATGGAAGATTACAGAAGCGCCGAGCT
GTTCACCCGGATGGTGCTGAACCCCAGGGGCGAGGACCACGACCCCGACC
AGAACGGCCAGGGCCTGATGCGGATCGCCGGACCCGTGACCGCCAAGGTG
CCCAGCACCGAGACAACCGAAACCATGCAGGGCATTGCCTTCGCCGGAGC
CCCCATGTACAGCAGCTTCAGCACCCTGGTGCGGAAGGCCGACCCCGAGT
ACGTGTTCAGCCCCGGCATCATTGCCGAGAGCAACCACAGCGTGTGCGAC
AAGAAAACCGTGCCCCTGACCTGGACCGGCTTCCTGGCCGTGAGCGGCGA
GATCGAGCGGATCACCGGCTGCACCGTGTTCTGCACCCTGGCCGGACCTG
GCGCCAGCTGCGAGGCCTACAGCGAGACAGGCATCTTCAACATCAGCAGC
CCCACCTGCCTGGTGAACAAGGTGCAGAAGTTCCGGGGCAGCGAGCAGCG
GATCAACTTCATGTGCCAGCGGGTGGACCAGGACGTGGTGGTGTACTGCA
ACGGCCAGAAAAAAGTGATCCTGACCAAGACCCTGGTGATCGGCCAGTGC
ATCTACACCTTCACCAGCCTGTTCAGCCTGATCCCTGGCGTGGCTCATAG
CCTGGCAGTCGAACTGTGCGTGCCTGGCCTGCACGGATGGGCCACCACCG
CCCTGCTGATCACCTTCTGCTTCGGCTGGCTGCTGATCCCCACAGTGACC
CTGATCATCCTGAAGATCCTGCGGCTGCTGACCTTCAGCTGCAGCCACTA
CAGCACCGAGTCCAAGTTCAAAGTGATTCTGGAACGCGTGAAGGTGGAGT
ACCAGAAAACCATGGGCAGCATGGTGTGCGACATCTGCCACCACGAGTGC
GAGACAGCCAAAGAGCTGGAAACCCACAAGAAGAGCTGCCCCGAGGGCCA
GTGCCCCTACTGCATGACCATCACAGAGAGCACCGAGAGCGCCCTGCAGG
CCCACTTCAGCATCTGCAAGCTGACCAACCGGTTCCAGGAAAACCTGAAG
AAGAGCCTGAAGCGGCCCGAAGTGCGGAAGGGCTGCTACCGGACCCTGGG
CGTGTTCCGGTACAAGAGCCGGTGCTATGTGGGCCTGGTGTGGGGCATTC
TGCTGACCACAGAGCTGATCATCTGGGCCGCCAGCGCCGACACCCCCCTG
ATGGAAAGCGGGTGGAGCGACACCGCTCATGGCGTGGGAATCGTGCCCAT
GAAAACCGACCTGGAACTGGACTTCGCCCTGGCCAGCAGCAGCAGCTACA
GCTACCGGCGGAAGCTGGTGAACCCCGCCAACCAGGAAGAGACACTGCCC
TTCCACTTCCAACTGGACAAGCAGGTGGTGCACGCCGAGATCCAGAACCT
GGGCCACTGGATGGACGGCACCTTCAATATCAAGACCGCCTTCCACTGCT
ACGGCGAGTGCAAGAAGTACGCCTACCCCTGGCAGACCGCCAAGTGCTTC
TTCGAGAAGGACTACCAGTACGAGACAAGCTGGGGCTGCAACCCCCCCGA
CTGTCCTGGCGTGGGCACCGGCTGTACCGCCTGCGGCGTGTACCTGGACA
AGCTGCGGAGCGTGGGCAAGGCCTACAAGATCGTGTCCTGAAGTACACC
CGGAAAGTGTGCATCCAGCTGGGCACAGAGCAGACATGCAAGCACATCGA
CGTGAACGATTGCCTGGTGACCCCCAGCGTGAAAGTCTGTATGATTGGCA
CCATCAGCAAGCTGCAGCCCGGCGATACCCTGCTGTTCCTGGGCCCCCTG

GAACAGGGCGGCATCATTCTGAAGCAGTGGTGTACCACCTCCTGCGTGTT
CGGCGACCCCGGCGACATCATGAGCACCACCTCCGGCATGCGGTGCCCCG
AGCACACCGGCAGCTTCCGGAAGATTTGTGGCTTCGCCACCACCCCTACC
TGCGAGTACCAGGGCAACACCGTGTCCGGCTTCCAGCGGATGATGGCCAC
CCGGGATAGCTTCCAGAGCTTCAACGTGACCGAGCCCCACATCACCAGCA
ACCGGCTGGAATGGATCGACCCCGACAGCAGCATCAAGGACCACATCAAC
ATGGTGCTCAATCGGGACGTGAGCTTCCAGGACCTGAGCGACAACCCCTG
CAAGGTGGACCTGCACACCCAGAGCATCGACGGCGCCTGGGGCAGCGGCG
TGGGCTTCACACTGGTGTGCACAGTGGGCCTGACCGAGTGCGCCAACTTC
ATCACCTCCATCAAGGCCTGCGACAGCGCCATGTGCTACGGCGCCACCGT
GACCAACCTGCTGCGGGGCTCCAACACAGTGAAGGTGGTGGGCAAGGGCG
GCCACAGCGGCAGCCTGTTTAAGTGCTGCCACGACACCGACTGCACCGAG
GAAGGCCTGGCCGCCAGCCCCCCTCACCTGGACAGAGTGACCGGCTACAA
CCAGATCGACAGCGACAAGGTGTACGACGATGGCGCCCCTCCCTGCACCA
TCAAGTGCTGGTTCACCAAGAGCGGCGAGTGGCTGCTGGGCATCCTGAAC
GGCAACTGGGTCGTCGTGGCCGTGCTGATCGTGATCCTGATCCTGTCTAT
CCTGCTGTTCAGCTTCTTCTGCCCCGTGCGGAACCGGAAGAACAAGGCCA
ACTAGCAAACATATATGTAAGTAAGGGTATGATCATATTATATCATTATG
CGTATACTCTTATATCTATAATATCTATGTATCCTTATACTCTAACTATT
TATATTAATTTTTACTTTTATACAAGTATTAACTAACCCATTACCAGCTA
AAAAAAACAAACCCTTAACACCTATATAATCCCATTTGCTTATTACGAGG
CTTTTGTTCCTGCGGAGTCTACTACTAAGATCT
ACGTATGATCAGCCTGACTGTGCCTTCTAGTTGCCAGCCATCTGTTGTT
TGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGG
GAAGACAATAGCAGGCATGCTGGGGATGCGGTGGGCTCTATGGCTTCTGA
GGCGGAAAGAACCAGCTGGGGCTCGACAGCTCGACTCTAGAATTGCTTCC
TCGCTCACTGACTCGCTGCGCTCGGTCGTTCGGCTGCGGCGAGCGGTATC
AGCTCACTCAAAGGCGGTAATACGGTTATCCACAGAATCAGGGGATAACG
CAGGAAAGAACATGTGAGCAAAAGGCCAGCAAAAGGCCAGGAACCGTAAA
AAGGCCGCGTTGCTGGCGTTTTTCCATAGGCTCCGCCCCCCTGACGAGCA
TCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGAC
CGCTGCGCCTTATCCGGTAACTATCGTCTTGAGTCCAACCCGGTAAGACA
CGACTTATCGCCACTGGCAGCAGCCACTGGTAACAGGATTAGCAGAGCGA
GGTATGTAGGCGGTGCTACAGAGTTCTTGAAGTGGTGGCCTAACTACGGC
TACACTAGAAGAACAGTATTTGGTATCTGCGCTCTGCTGAAGCCAGTTAC

CTTCGGAAAAAGAGTTGGTAGCTCTTGATCCGGCAAACAAACCACCGCTG

GTAGCGGTGGTTTTTTTGTTTGCAAGCAGCAGATTACGCGCAGAAAAAA

GGATCTCAAGAAGATCCTTTGATCTTTTCTACGGGGTCTGACGCTCAGTG

GAACGAAAACTCACGTTAAGGGATTTTGGTCATGAGATTATCAAAAGGA

TCTTCACCTAGATCCTTTTAAATTAAAAATGAAGTTTTAAATCAATCTAA

AGTATATATGAGTAAACTTGGTCTGACAGTTACCAATGCTTAATCAGTGA

GGCACCTATCTCAGCGATCTGTCTATTTCGTTCATCCATAGTTGCCTGAC

TC

This is the full-length optimized SNV M gene of pWRG/SN-M(opt). The nucleic acids outside the Not 1 and Bgl II cloning sites are not considered significant to the use of the SNV M gene.

Another valuable sequence is the isolated nucleic acid sequence of the SNV M gene (optimized) open reading frame plus the flanking sequence, as shown in SEQ ID NO:2, as follows:

GCGGCCGCGGATCTGCAGGAATTCGGCACGAGAGTAGTAGACTCCGCACG

AAGAAGCAAACACTGAATAAAGGATATACAGA<u>ATGGTGGGCTGGGTGTGC</u>

<u>ATCTTCCTGGTGGTGCTGACCACCGCCACAGCCGGCCTGACCCGGAACCT</u>

<u>GTACGAGCTGAAGATCGAGTGCCCCCACACCGTGGGCCTGGGCCAGGGCT</u>

<u>ACGTGACCGGCAGCGTGGAGACAACCCCCATCCTGCTGACCCAGGTGGCC</u>

<u>GACCTGAAGATTGAGAGCAGCTGCAACTTCGACCTGCACGTGCCCGCCAC</u>

<u>CACCACCCAGAAATACAACCAGGTGGACTGGACCAAGAAGAGCAGCACCA</u>

<u>CCGAGAGCACCAACGCCGGAGCCACCACCTTCGAGGGCAAGACCAAAGAA</u>

<u>GTGAACCTGAAGGGCACCTGCAACATCCCCCCCACCACATTTGAGGCCGC</u>

<u>CTACAAGAGCAGAAAGACCGTGATCTGCTACGACCTGGCCTGCAACCAGA</u>

<u>CCCACTGCCTGCCCACCGTGCACCTGATCGCCCCCGTGCAGACCTGCATG</u>

<u>AGCGTGCGGAGCTGCATGATCGGCCTGCTGTCCAGCCGGATCCAGGTGAT</u>

<u>CTACGAGAAAACCTACTGCGTGACCGGCCAGCTGATCGAGGGCCTGTGCT</u>

<u>TCATCCCCACCCACACAATCGCCCTGACCCAGCCCGGCCACACCTACGAC</u>

<u>ACCATGACCCTGCCCGTGACCTGCTTTCTGGTGGCCAAGAAGCTGGGCAC</u>

<u>CCAGCTGAAGCTGGCCGTGGAGCTGGAAAAGCTGATCACCGGCGTGAGCT</u>

<u>GCACCGAGAACAGCTTCCAGGGCTACTACATCTGCTTCATCGGCAAGCAC</u>

<u>AGCGAGCCCCTGTTCGTGCCCACCATGGAAGATTACAGAAGCGCCGAGCT</u>

<u>GTTCACCCGGATGGTGCTGAACCCCAGGGGCGAGGACCACGACCCCGACC</u>

<u>AGAACGGCCAGGGCCTGATGCGGATCGCCGGACCCGTGACCGCCAAGGTG</u>

<u>CCCAGCACCGAGACAACCGAAACCATGCAGGGCATTGCCTTCGCCGGAGC</u>

<u>CCCCATGTACAGCAGCTTCAGCACCCTGGTGCGGAAGGCCGACCCCGAGT</u>

<u>ACGTGTTCAGCCCCGGCATCATTGCCGAGAGCAACCACAGCGTGTGCGAC</u>

<u>AAGAAAACCGTGCCCCTGACCTGGACCGGCTTCCTGGCCGTGAGCGGCGA</u>

<u>GATCGAGCGGATCACCGGCTGCACCGTGTTCTGCACCCTGGCCGGACCTG</u>

<u>GCGCCAGCTGCGAGGCCTACAGCGAGACAGGCATCTTCAACATCAGCAGC</u>

<u>CCCACCTGCCTGGTGAACAAGGTGCAGAAGTTCCGGGGCAGCGAGCAGCG</u>

<u>GATCAACTTCATGTGCCAGCGGGTGGACCAGGACGTGGTGGTGTACTGCA</u>

<u>ACGGCCAGAAAAAGTGATCCTGACCAAGACCCTGGTGATCGGCCAGTGC</u>

<u>ATCTACACCTTCACCAGCCTGTTCAGCCTGATCCCTGGCGTGGCTCATAG</u>

<u>CCTGGCAGTCGAACTGTGCGTGCCTGGCCTGCACGGATGGGCCACCACCG</u>

<u>CCCTGCTGATCACCTTCTGCTTCGGCTGGCTGCTGATCCCCACAGTGACC</u>

<u>CTGATCATCCTGAAGATCCTGCGGCTGCTGACCTTCAGCTGCAGCCACTA</u>

<u>CAGCACCGAGTCCAAGTTCAAAGTGATTCTGGAACGCGTGAAGGTGGAGT</u>

<u>ACCAGAAAACCATGGGCAGCATGGTGTGCGACATCTGCCACCACGAGTGC</u>

<u>GAGACAGCCAAAGAGCTGGAAACCCACAAGAAGAGCTGCCCCGAGGGCCA</u>

<u>GTGCCCCTACTGCATGACCATCACAGAGAGCACCGAGAGCGCCCTGCAGG</u>

<u>CCCACTTCAGCATCTGCAAGCTGACCAACCGGTTCCAGGAAAACCTGAAG</u>

<u>AAGAGCCTGAAGCGGCCCGAAGTGCGGAAGGGCTGCTACCGGACCCTGGG</u>

<u>CGTGTTCCGGTACAAGAGCCGGTGCTATGTGGGCCTGGTGTGGGGCATTC</u>

<u>TGCTGACCACAGAGCTGATCATCTGGGCCGCCAGCGCCGACACCCCCCTG</u>

<u>ATGGAAAGCGGGTGGAGCGACACCGCTCATGGCGTGGGAATCGTGCCCAT</u>

<u>GAAAACCGACCTGGAACTGGACTTCGCCCTGGCCAGCAGCAGCAGCTACA</u>

<u>GCTACCGGCGGAAGCTGGTGAACCCCGCCAACCAGGAAGAGACACTGCCC</u>

<u>TTCCACTTCCAACTGGACAAGCAGGTGGTGCACGCCGAGATCCAGAACCT</u>

<u>GGGCCACTGGATGGACGGCACCTTCAATATCAAGACCGCCTTCCACTGCT</u>

<u>ACGGCGAGTGCAAGAAGTACGCCTACCCCTGGCAGACCGCCAAGTGCTTC</u>

<u>TTCGAGAAGGACTACCAGTACGAGACAAGCTGGGGCTGCAACCCCCCCGA</u>

<u>CTGTCCTGGCGTGGGCACCGGCTGTACCGCCTGCGGCGTGTACCTGGACA</u>

<u>AGCTGCGGAGCGTGGGCAAGGCCTACAAGATCGTGTCCCTGAAGTACACC</u>

<u>CGGAAAGTGTGCATCCAGCTGGGCACAGAGCAGACATGCAAGCACATCGA</u>

<u>CGTGAACGATTGCCTGGTGACCCCCAGCGTGAAAGTCTGTATGATTGGCA</u>

<u>CCATCAGCAAGCTGCAGCCCGGCGATACCCTGCTGTTCCTGGGCCCCCTG</u>

<u>GAACAGGGCGGCATCATTCTGAAGCAGTGGTGTACCACCTCCTGCGTGTT</u>

<u>CGGCGACCCCGGCGACATCATGAGCACCACCTCCGGCATGCGGTGCCCCG</u>

<u>AGCACACCGGCAGCTTCCGGAAGATTTGTGGCTTCGCCACCACCCCTACC</u>

<u>TGCGAGTACCAGGGCAACACCGTGTCCGGCTTCCAGCGGATGATGGCCAC</u>

<u>CCGGGATAGCTTCCAGAGCTTCAACGTGACCGAGCCCCACATCACCAGCA</u>

<u>ACCGGCTGGAATGGATCGACCCCGACAGCAGCATCAAGGACCACATCAAC</u>

<u>ATGGTGCTCAATCGGGACGTGAGCTTCCAGGACCTGAGCGACAACCCCTG</u>

<u>CAAGGTGGACCTGCACACCCAGAGCATCGACGGCGCCTGGGGCAGCGGCG</u>

<u>TGGGCTTCACACTGGTGTGCACAGTGGGCCTGACCGAGTGCGCCAACTTC</u>

<u>ATCACCTCCATCAAGGCCTGCGACAGCGCCATGTGCTACGGCGCCACCGT</u>

<u>GACCAACCTGCTGCGGGGCTCCAACACAGTGAAGGTGGTGGGCAAGGGCG</u>

<u>GCCACAGCGGCAGCCTGTTTAAGTGCTGCCACGACACCGACTGCACCGAG</u>

<u>GAAGGCCTGGCCGCCAGCCCCCCTCACCTGGACAGAGTGACCGGCTACAA</u>

-continued

CCAGATCGACAGCGACAAGGTGTACGACGATGGCGCCCCTCCCTGCACCA

TCAAGTGCTGGTTCACCAAGAGCGGCGAGTGGCTGCTGGGCATCCTGAAC

GGCAACTGGGTCGTCGTGGCCGTGCTGATCGTGATCCTGATCCTGTCTAT

CCTGCTGTTCAGCTTCTTCTGCCCCGTGCGGAACCGGAAGAACAAGGCCA

ACTAGCAAACATATATGTAAGTAAGGGTATGATCATATTATATCATTATG

CGTATACTCTTATATCTATAATATCTATGTATCCTTATACTCTAACTATT

TATATTAATTTTTACTTTTATACAAGTATTAACTAACCCATTACCAGCTA

AAAAAAACAAACCCTTAACACCTATATAATCCCATTTGCTTATTACGAGG

CTTTTGTTCCTGCGGAGTCTACTACTAAGATCT

The flanking sequences are the cloning sites plus the SNV M segment non-translated regions of SEQ ID NO:1, and also includes the "extraneous sequence" at the 5' end. The first flanking sequence is:
ATCTGCAGGAATTCGGCACGAGAGTAG-TAGACTCCGCACGAAGAAGCAAA CACT-GAATAAAGGATATACAGA (SEQ ID:NO 5); the second flanking sequence is (SEQ ID NO: 6)
CAAACATATATGTAAGTAAGGGTATGATCATATTATATCATTATGCGTAT

ACTCTTATATCTATAATATCTATGTATCCTTATACTCTAACTATTTATAT

TAATTTTTACTTTTATACAAGTATTAACTAACCCATTACCAGCTAAAAAA

AACAAACCCTTAACACCTATATAATCCCATTTGCTTATTACGAGGCTTTT

GTTCCTGCGGAGTCTACTACTAA

Another valuable sequence is the isolated nucleic acid sequence of the SNV M gene (optimized) open reading frame by itself, as shown in SEQ ID NO:3. As a point of reference, the ORF begins with the ATG start codon and ends with the TAG stop codon. SEQ ID NO:3 is as follows:

ATGGTGGGCTGGGTGTGCATCTTCCTGGTGGTGCTGACCACCGCCACAGC

CGGCCTGACCCGGAACCTGTACGAGCTGAAGATCGAGTGCCCCACACCG

TGGGCCTGGGCCAGGGCTACGTGACCGGCAGCGTGGAGACAACCCCCAT

CCTGCTGACCCAGGTGGCCGACCTGAAGATTGAGAGCAGCTGCAACTTC

GACCTGCACGTGCCCGCCACCACCACCCAGAAATACAACCAGGTGGAC

TGGACCAAGAAGAGCAGCACCACCGAGAGCACCAACGCCGGAGCCACC

ACCTTCGAGGCCAAGACCAAAGAAGTGAACCTGAAGGGCACCTGCAA

CATCCCCCCACCACATTTGAGGCCGCCTACAAGAGCAGAAAGACCG

TGATCTGCTACGACCTGGCCTGCAACCAGACCCACTGCCTGCCCACC

GTGCACCTGATCGCCCCCGTGCAGACCTGCATGAGCGTGCGGAGCTGC

ATGATCGGCCTGCTGTCCAGCCGGATCCAGGTGATCTACGAGAAAAC

CTACTGCGTGACCGGCCAGCTGATCGAGGGCCTGTGCTTCATCCCC

ACCCACACAATCGCCCTGACCCAGCCCGGCCACACCTACGACACCAT

GACCCTGCCCGTGACCTGCTTTCTGGTGGCCAAGAAGCTGGGCAC

CCAGCTGAAGCTGGCCGTGGAGCTGGAAAAGCTGATCACCGGCGT

GAGCTGCACCGAGAACAGCTTCCAGGGCTACTACATCTGCTTCA

TCGGCAAGCACAGCGAGCCCCTGTTCGTGCCCACCATGGAAGATTA

CAGAAGCGCCGAGCTGTTCACCCGGATGGTGCTGAACCCCAGGGGCGAG

GACCACGACCCCGACCAGAACGGCCAGGGCCTGATGCGGATCGCCGGACC

CGTGACCGCCAAGGTGCCCAGCACCGAGACAACCGAAACCATGCAGGGCA

TTGCCTTCGCCGGAGCCCCCATGTACAGCAGCTTCAGCACCCTGGTGCGG

AAGGCCGACCCCGAGTACGTGTTCAGCCCCGGCATCATTGCCGAGAGCAA

CCACAGCGTGTGCGACAAGAAAACCGTGCCCCTGACCTGGACCGGCTTCC

TGGCCGTGAGCGGCGAGATCGAGCGGATCACCGGCTGCACCGTGTTCTGC

ACCCTGGCCGGACCTGGCGCCAGCTGCGAGGCCTACAGCGAGACAGGCAT

CTTCAACATCAGCAGCCCCACCTGCCTGGTGAACAAGGTGCAGAAGTTCC

GGGGCAGCGAGCAGCGGATCAACTTCATGTGCCAGCGGGTGGACCAGGAC

GTGGTGGTGTACTGCAACGGCCAGAAAAAAGTGATCCTGACCAAGACCCT

GGTGATCGGCCAGTGCATCTACACCTTCACCAGCCTGTTCAGCCTGATCC

CTGGCGTGGCTCATAGCCTGGCAGTCGAACTGTGCGTGCCTGGCCTGCAC

GGATGGGCCACCACCGCCCTGCTGATCACCTTCTGCTTCGGCTGGCTGCT

GATCCCCACAGTGACCCTGATCATCCTGAAGATCCTGCGGCTGCTGACCT

TCAGCTGCAGCCACTACAGCACCGAGTCCAAGTTCAAAGTGATTCTGGAA

CGCGTGAAGGTGGAGTACCAGAAAACCATGGGCAGCATGGTGTGCGACAT

CTGCCACCACGAGTGCGAGACAGCCAAAGAGCTGGAAACCCACAAGAAGA

GCTGCCCCGAGGGCCAGTGCCCCTACTGCATGACCATCACAGAGAGCACC

GAGAGCGCCCTGCAGGCCCACTTCAGCATCTGCAAGCTGACCAACCGGTT

CCAGGAAAACCTGAAGAAGAGCCTGAAGCGGCCCGAAGTGCGGAAGGGCT

GCTACCGGACCCTGGGCGTGTTCCGGTACAAGAGCCGGTGCTATGTGGGC

CTGGTGTGGGGCATTCTGCTGACCACAGAGCTGATCATCTGGGCCGCCAG

CGCCGACACCCCCCTGATGGAAAGCGGGTGGAGCGACACCGCTCATGGCG

TGGGAATCGTGCCCATGAAAACCGACCTGGAACTGGACTTCGCCCTGGCC

AGCAGCAGCAGCTACAGCTACCGGCGAAGCTGGTGAACCCCGCCAACCA

GGAAGAGACACTGCCCTTCCACTTCCAACTGGACAAGCAGGTGGTGCACG

CCGAGATCCAGAACCTGGGCCACTGGATGGACGGCACCTTCAATATCAAG

ACCGCCTTCCACTGCTACGGCGAGTGCAAGAAGTACGCCTACCCCTGGCA

GACCGCCAAGTGCTTCTTCGAGAAGGACTACCAGTACGAGACAAGCTGGG

GCTGCAACCCCCCGACTGTCCTGGCGTGGGCACCGGCTGTACCGCCTGC

GGCGTGTACCTGGACAAGCTGCGGAGCGTGGGCAAGGCCTACAAGATCGT

GTCCCTGAAGTACACCCGGAAAGTGTGCATCCAGCTGGGCACAGAGCAGA

CATGCAAGCACATCGACGTGAACGATTGCCTGGTGACCCCCAGCGTGAAA

GTCTGTATGATTGGCACCATCAGCAAGCTGCAGCCCGGCGATACCCTGCT

GTTCCTGGGCCCCCTGGAACAGGGCGGCATCATTCTGAAGCAGTGGTGTA

CCACCTCCTGCGTGTTCGGCGACCCCGGCGACATCATGAGCACCACCTCC

GGCATGCGGTGCCCCGAGCACACCGGCAGCTTCCGGAAGATTTGTGGCTT

CGCCACCACCCCTACCTGCGAGTACCAGGGCAACACCGTGTCCGGCTTCC

-continued

```
AGCGGATGATGGCCACCCGGGATAGCTTCCAGAGCTTCAACGTGACCGAG

CCCCACATCACCAGCAACCGGCTGGAATGGATCGACCCCGACAGCAGCAT

CAAGGACCACATCAACATGGTGCTCAATCGGGACGTGAGCTTCCAGGACC

TGAGCGACAACCCCTGCAAGGTGGACCTGCACACCCAGAGCATCGACGGC

GCCTGGGGCAGCGGCGTGGGCTTCACACTGGTGTGCACAGTGGGCCTGAC

CGAGTGCGCCAACTTCATCACCTCCATCAAGGCCTGCGACAGCGCCATGT

GCTACGGCGCCACCGTGACCAACCTGCTGCGGGGCTCCAACACAGTGAAG

GTGGTGGGCAAGGGCGGCCACAGCGGCAGCCTGTTTAAGTGCTGCCACGA

CACCGACTGCACCGAGGAAGGCCTGGCCGCCAGCCCCCCTCACCTGGACA

GAGTGACCGGCTACAACCAGATCGACAGCGACAAGGTGTACGACGATGGC

GCCCCTCCCTGCACCATCAAGTGCTGGTTCACCAAGAGCGGCGAGTGGCT

GCTGGGCATCCTGAACGGCAACTGGGTCGTCGTGGCCGTGCTGATCGTGA

TCCTGATCCTGTCTATCCTGCTGTTCAGCTTCTTCTGCCCCGTGCGGAAC

CGGAAGAACAAGGCCAACTAG
```

SEQ ID NO:2 and SEQ ID NO:3 are especially useful as a DNA cassette. The preferred cassette is the SNV optimized M gene cassette in the SNV-M (opt) (preferably taken from the Not 1 site to the BglII site, or minimally the ORF (SEQ ID NO:3) operably linked to a promoter) which can be subcloned into any other vaccine/expression system available, and used to generate active or passive immunity against SN virus. The DNA cassette specifically includes at least SEQ ID NO:2 linked to a promoter operable in a eukaryotic expression system. Alternatively, the DNA cassette includes the sequence in SEQ ID NO:3 (within pWRG/SN-M(opt)) from the ATG start codon to the TAG stop codon.

The peptide encoded by DNA sequence SEQ ID NO:3 is as follows: SN-M(opt) amino acid sequence

```
MVGWVCIFLVVLTTATAGLTRNLYELKIECPHTVGLGQGYVTGSVETTP

ILLTQVADLKIESSCNFDLHVPATTTQKYNQVDWTKKSSTTESTNAGAT

TFEAKTKEVNLKGTCNIPPTTFEAAYKSRKTVICYDLACNQTHCLPTVH

LIAPVQTCMSVRSCMIGLLSSRIQVIYEKTYCVTGQLIEGLCFIPTHTI

ALTQPGHTYDTMTLPVTCFLVAKKLGTQLKLAVELEKLITGVSCTENSF

QGYYICFIGKHSEPLFVPTMEDYRSAELFTRMVLNPRGEDHDPDQNGQG

LMRIAGPVTAKVPSTETTETMQGIAFAGAPMYSSFSTLVRKADPEYVFS

PGIIAESNHSVCDKKTVPLTWTGFLAVSGEIERITGCTVFCTLAGPGAS

CEAYSETGIFNISSPTCLVNKVQKFRGSEQRINFMCQRVDQDVVVYCNG

QKKVILTKTLVIGQCIYTFTSLFSLIPGVAHSLAVELCVPGLHGWATTA

LLITFCFGWLLIPTVTLIILKILRLLTFSCSHYSTESKFKVILERVKVE

YQKTMGSMVCDICHHECETAKELETHKKSCPEGQCPYCMTITESTESAL

QAHFSICKLTNRFQENLKKSLKRPEVRKGCYRTLGVFRYKSRCYVGLVW

GILLTTELIIWAASADTPLMESGWSDTAHGVGIVPMKTDLELDFALASS

SSYSYRRKLVNPANQEETLPFHFQLDKQVVHAEIQNLGHWMDGTFNIKT

AFHCYGECKKYAYPWQTAKCFFEKDYQYETSWGCNPPDCPGVGTGCTAC

GVYLDKLRSVGKAYKIVSLKYTRKVCIQLGTEQTCKHIDVNDCLVTPSV

KVCMIGTISKLQPGDTLLFLGPLEQGGIILKQWCTTSCVFGDPGDIMST

TSGMRCPEHTGSFRKICGFATTPTCEYQGNTVSGFQRMMATRDSFQSFN

VTEPHITSNRLEWIDPDSSIKDHINMVLNRDVSFQDLSDNPCKVDLHTQ

SIDGAWGSGVGFTLVCTVGLTECANFITSIKACDSAMCYGATVTNLLRG

SNTVKVVGKGGHSGSLFKCCHDTDCTEEGLAASPPHLDRVTGYNQIDSD

KVYDDGAPPCTIKCWFTKSGEWLLGILNGNWVVVAVLIVILILSILLFS

FFCPVRNRKNKAN
```

There are four residues that are altered in the M(opt) from the M(2a): K at position 27, T at position 241, D at position 434, and S at position 519. The enhanced immunogenicity of pWRG/SN-M(opt) vs pWRG/SN-M(2a) is speculated to be due to the nucleic acid changes, one or more of the four amino acid changes, or a combination thereof.

In another embodiment, the invention entails a recombinant DNA construct comprising:
(i) a vector, and
(ii) the DNA fragment comprising the nucleic acid sequence set forth in
SEQ ID NO:1, SEQ ID NO:2 or SEQ ID NO:3, or a DNA fragment comprising a nucleic acid sequence that encodes the amino acid sequence set forth in SEQ ID NO:4, operably linked to a promoter sequence.

As would be understood by someone having skill in this art, the DNA constructs of our invention will have all necessary structural components for expression of the DNA fragment of interest (e.g., promoters functional in mammals, and the like). The vector can take the form of a plasmid such as pCRII (Invitrogen) or pJW4303 (Konishi, E. et al., 1992, *Virology* 188:714), or any expression vector such as viral vectors e.g. adenovirus or Venezuelan equine encephalitis virus and others known in the art. Preferably the vector is a recombinant adenovirus or recombinant vesicular stomatitis virus, or alphavirus replicon. Preferably, a promoter sequence operable in the target cell is operably linked to the DNA sequence. Several such promoters are known for mammalian systems which may be joined 5', or upstream, of the coding sequence for the encoded protein to be expressed. A suitable and preferred promoter is the human cytomegalovirus immediate early promoter, preferably operably linked to intron A. Another preferred promoter is the beta-actin promoter or the SV40 promoter. A downstream transcriptional terminator, or polyadenylation sequence, such as the polyA addition sequence of the bovine growth hormone gene, may also be added 3' to the protein coding sequence.

Preferably, the construct is the pWRG/SN-M(opt) DNA vaccine plasmid, whose sequence is set forth above and referred to as SEQ ID NO:1.

In a further embodiment, the present invention relates to host cells stably transformed or transfected with the above-described recombinant DNA constructs. The host cell can be prokaryotic such as *Bacillus* or *E. coli*, or eukaryotic such a *Saccharomyces* or *Pichia*, or mammalian cells or insect cells. The vector containing the Sin Nombre virus M gene sequence is expressed in the bacteria and the expressed product used for diagnostic procedures or as a vaccine. Please see e.g., Maniatis et al., 1985 *Molecular Cloning: A Laboratory Manual* or *DNA Cloning*, Vol. I and II (D. N. Glover, ed., 1985) for general cloning methods. The DNA sequence can be present in the vector operably linked to a highly purified IgG molecule, an adjuvant, a carrier, or an agent for aid in purification of Sin Nombre virus proteins or peptides. The transformed or transfected host cells can be used as a source of DNA sequences described above. When the recombinant molecule takes the form of an expression system, the transformed or transfected cells can be used as a source of the protein or peptide encoded by the DNA. The DNA can be used as circular or linear, or linearized plasmid as long as the Sin Nombre virus sequences are operably linked to a promoter which can be expressed in the transfected cell.

In another embodiment, the invention entails vaccines against infection with Sin Nombre virus. In a method for eliciting in a subject an immune response against Sin Nombre virus, the method comprises administering to a subject a DNA fragment comprising a genome segment of hantavirus. In one preferred embodiment, the vaccine composition comprises an effective immunizing amount of SNV plasmid DNA, which plasmid DNA comprises one or more of the recombinant DNA constructs described above, and a pharmacologically acceptable carrier. That is, the recombinant DNA construct should minimally include (i) a vector, and (ii) the DNA fragment comprising the nucleic acid sequence set forth in SEQ ID NO:1, SEQ ID NO:2 or SEQ ID NO:3, or a DNA fragment comprising a nucleic acid sequence that encodes the amino acid sequence set forth in SEQ ID NO:4. The DNA fragment is operably linked to a promoter sequence. The pharmacologically acceptable carrier may be any carrier that is known in the art, which is safe and effective for a SNV DNA vaccine. Examples of such carriers include PBS, water, saline, Tris-EDTA, and mixtures of these.

The vaccine composition may which further comprise an adjuvant. The adjuvant may be any one that is known in the art, which is safe and effective for a SNV DNA vaccine. As used herein the term "adjuvant" refers to any component which improves the body's response to a vaccine. The adjuvant will typically comprise about 0.1 to 50% vol/vol of the vaccine formulation of the invention, more preferably about 1 to 50% of the vaccine, and even more desirably about 1 to 20% thereof. Examples of such adjuvants include CpG (cystein-phosphate-guanine) oligodeoxynucleic acid, or plasmid DNA-encoded heat labile enterotoxins, or alum.

The immunizing amount of SNV plasmid DNA is preferably between about 5 micrograms (e.g., with gene gun administration) and about 5 milligrams (e.g., electroporation or other forms of administration). By "immunizing amount", it is meant the amount of vaccine or immunogenic composition that is needed to raise high titers of neutralizing antibodies in response to the composition.

One unique aspect of our invention is that it can further comprise one or more additional vaccine components of other hantaviruses, to make a bi-valent, tri-valent, multivalent or pan-virus vaccine. In one embodiment, a DNA vaccine is contemplated that elicits an immune response against multiple HPS-associated hantaviruses and protects against more than one HPS virus. Such a DNA vaccine comprises one of the SNV sequences described above (SEQ ID NO:1, SEQ ID NO:2 or SEQ ID NO:3), in combination with an HPS hantavirus M gene DNA vaccine (such as M gene DNA vaccine from one or more of Black Creek Canal virus, Bayou virus, New York virus, Andes virus and Laguna Negra virus) such that each M gene is expressed in the subject. The respective M gene DNA sequences may each be part of respective recombinant constructs that each include (i) a vector and (ii) the desired DNA fragment that is operably linked to a promoter sequence. A preferred HPS virus is Andes virus.

In another embodiment, a DNA vaccine elicits an immune response against both HFRS and HPS hantavirus and protects against all the hantaviruses causing severe disease by providing to a subject a DNA vaccine comprising one of the SNV sequences described above (SEQ ID NO:1, SEQ ID NO:2 or SEQ ID NO:3), in combination with at least one HFRS hantavirus M gene DNA vaccine (such as Hantaan M gene DNA vaccine, Puumala M gene DNA vaccine, Seoul M gene DNA vaccine and Dobrava M gene DNA) such that each M gene is expressed in the subject. Furthermore, the M gene DNA vaccine from one or more of another HPS-associated virus (such as Black Creek Canal virus, Bayou virus, New York virus, Andes virus and Laguna Negra virus) may be included, to strengthen the HPS component. The respective M gene DNA sequences may each be part of respective recombinant constructs that each include (i) a vector and (ii) the desired DNA fragment that is operably linked to a promoter sequence.

The SNV M gene or the other HPS or HFRS M gene may be administered separately, i.e. on seperate vectors, or may be combined on the same vector as is described in one aspect of this invention. For instance, a pan-HPS virus vaccine can include any of SEQ ID NO:1, SEQ ID NO:2, or SEQ ID NO:3, and a suitable Andes M gene sequence (in whole, or an ORF with flanking sequences, or simply the ORF). A preferred Andes M gene sequence is SEQ ID NO:10, which is the full-length ANDV M gene described in U.S. Pat. No. 7,217,812 (and the sequence is referred to as SEQ ID NO:8 therein). A preferred Puumala M gene sequence is SEQ ID NO:11, which is the full-length PUUV M gene described in U.S. patent publication number 20100323024 (and the sequence is referred to as SEQ ID NO: 1 therein). A preferred Hantaan M gene sequence is SEQ ID NO:12, which is the full-length HNTV M gene described in U.S. Pat. No. 7,217,812 (and the sequence is referred to as SEQ ID NO:7 therein). A preferred Seoul M gene sequence is SEQ ID NO:13, which is the full-length Seoul M gene described in U.S. Pat. No. 7,217,812 (and the sequence is referred to as SEQ ID NO:3 therein). The preferred HPS/HFRS vaccine combination includes Hantaan, Puumala, Andes, and Sin Nombre DNA vaccines, although Seoul DNA vaccine is also a good component for the combined vaccine. Any of these M genes can be used in full-length, or just the ORF with flanking sequences, or simply the ORF. As someone skilled in this art would understand, this invention entailing the combination of hantavirus M genes is not limited at all to these specific M genes—these are merely examples, and any M gene isolated or derived or improved or otherwise altered from the hantavirus (e.g., an altered Seoul M gene, or a non-optimized Puumala M gene).

The vaccine may involve the delivery of pWRG/SN-M (opt) DNA (SEQ ID NO:1), or the DNA of SEQ ID NO:2 or SEQ ID NO:3 (or, if a multivalent vaccine is employed, one or more of the above-described sequences of the other HPS- or HFRS-associated viruses) by any of several platforms used to deliver gene-based vaccines. For example, the vaccine could comprise a composition comprising inert particles and a nucleic acid coated onto the inert particles producing nucleic acid coated particles. The nucleic acid will comprise a promoter operative in the cells of a mammal and further comprise (or even consist essentially of or consist of) SEQ ID NO:1, SEQ ID NO:2 or SEQ ID NO:3. As would be understood by someone having skill in this art, the ORF sequence (SEQ ID NO:3) is essential (and for the other HPS- or HFRS-associated viruses, the ORF of the respective M gene). The flanking region between the cloning sites and the ORF are preferably included, as they may be helpful for efficient expression. The inert particle may be gold particles, silver particles, platinum particles, tungsten particles, polystyrene particles, polypropylene particles, polycarbonate particles, and the like, as would be understood by someone having ordinary skill in this art. In particular, it is preferred that the inert particle is suitable for use in a gene gun.

The invention further encompasses a method for inducing a protective immune response against Sin Nombre virus infection in a mammal, comprising the step of accelerating into epidermal cells of the mammal in vivo a composition comprising inert particles and a nucleic acid coated onto the inert particles producing nucleic acid coated particles, such that said nucleic acid is expressed (e.g., gene gun administration). The nucleic acid will comprise a promoter effective and functional in the cells of a mammal and SEQ ID NO:1, SEQ ID NO:2 or SEQ ID NO:3.

Electroporation is another method of administration. Electroporation involves injecting plasmid DNA into a tissue (e.g. muscle or skin) and then applying micropulses of an electric field causeing transient permeability of the cells of the vaccinee. This transient permeability allows for a more efficient take-up of the DNA vaccine plasmid.

In a more general method for inducing a protective immune response against Sin Nombre virus infection in a mammal, a composition is administered to a mammal comprising a nucleic acid comprising a promoter operative in the cells of a mammal and one of SEQ ID NO: 1, SEQ ID NO:2 or SEQ ID NO:3. It is generally preferred that the chosen sequence be inserted into a plasmid, and the plasmid administered. To that end, preferably the nucleic acid is a component of one of the above-referenced DNA constructs. However, it is known that a linear piece of DNA consisting of only a promoter and the gene-of-interest can elicit an immune response. Thus, one option for the composition is that it comprises SEQ ID NO: 1, SEQ ID NO:2 or SEQ ID NO:3 plus an appropriate promoter. One preferred method comprises the step of administering a composition comprising an effective immunizing amount of SNV plasmid DNA, which plasmid DNA comprises one of the recombinant DNA construct described above; and a pharmacologically acceptable carrier. Another preferred method comprises the step of administering a composition comprising an effective immunizing amount of EQ ID NO: 1, SEQ ID NO:2 or SEQ ID NO:3 operably linked to a promoter operative in the cells of a mammal plus an appropriate promoter; and a pharmacologically acceptable carrier. Appropriate pharmacologically acceptable carriers are discussed elsewhere in this document. Preferably, the immunizing amount of SNV plasmid DNA is between about 5 micrograms and about 5 milligrams.

In another embodiment, this invention provides a method for raising high titers of neutralizing antibodies against Sin Nombre virus in a mammal or a bird. The method comprises the step of administering a composition comprising a SNV plasmid DNA which comprises one or more of the recombinant DNA constructs described above (including SEQ ID NO:1, SEQ ID NO:2 or SEQ ID NOT:3); and a pharmacologically acceptable carrier. Preferably, the titers are at least 100, and more preferably are at least 10,000. As someone having ordinary skill in this art would recognize, in the context of hantavirus infection, titers with a level of at least 100 are significant, and considered "high" because they are 10 times higher than the minimal titer of 10 that has been used to evaluate vaccines against HFRS (a titer of 10 indicates there was a 50% reduction in plaque forming units when virus was combined with serum for a final dilution of 1:10). Titers of >10,000 are similar to those produced in person who have developed HPS and survived.

High titers are obtained even with only one dose or administration of the composition, although additional doses or vaccinations can boost titers even higher. The pharmacologically acceptable carrier can be any such carrier known in the art which is safe and does not hamper effectiveness of the composition. Examples are mentioned above, and throughout this document. The amount of the composition required for raising high titers of neutralizing antibodies is between about 5 micrograms and about 5 milligrams. The inventors discovered that the composition was effective in both mammals and birds.

The invention also encompasses post-exposure prophylactics, or passive vaccines, for treating or preventing Sin Nombre virus infections, for someone who has already been exposed to Sin Nombre virus and may be infected. Polyclonal antibodies may be obtained using methods known in the art, from a population of vaccinees (human or animal) vaccinated with a Sin Nombre virus DNA vaccine comprised of a plasmid expressing SEQ ID NO:1, SEQ ID NO:2 or SEQ ID NO;3, such as pWRG/SN-M(opt). Alternatively, polyclonal or monoclonal antibodies could be produced in animals using the pWRG/SN-M(opt) plasmid, or a plasmid containing SEQ ID NO:2 or SEQ ID NO:3, operably associated with a promoter and any other elements needed for expression of the sequence. The methods entail administration of a therapeutically or prophylactically effective amount of the antibodies which protect against Sin Nombre virus disease in combination with a pharmaceutically acceptable carrier or excipient. For instance, a therapeutic composition for ameliorating symptoms of Sin Nombre virus infection may comprise a composition comprising these polyclonal antibodies, and a pharmaceutically acceptable excipient. For instance, pWRG/SN-M(opt) may be used to vaccinate ducks, sheep, or transgenic cows or rabbits to produce polyclonal neutralizing antibodies for use in humans.

The invention also entails a method for diagnosis of Sin Nombre virus infection by assaying for the presence of Sin Nombre virus in a sample using the above-described antibodies. For instance, a method for the diagnosis of Sin Nombre virus infection may comprise the steps of:

(i) contacting a sample from an individual suspected of having Sin Nombre virus infection with a composition comprising the polyclonal antibodies (e.g., the pWRG/SN-M(opt) plasmid could be used to produce diagnostic antibodies in any of several species of animals—goats, rabbits, etc.); and (ii) detecting the presence or absence of Sin Nombre virus infection by detecting the presence or absence of a complex formed between Sin Nombre virus antigens and antibodies specific therefor.

In addition, the invention encompasses novel immunoprobes and test kits for detection of Sin Nombre virus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to Sin Nombre virus to form an immunological complex and detecting the formation of the immunological complex such that presence or absence of the immunological complex correlates with presence or absence of Sin Nombre virus. For instance, the kit may include kit may include a container holding one or more polyclonal antibodies of the present invention which binds a Sin Nombre virus antigen, and ancillary reagents suitable for use in detecting Sin Nombre virus antigens, and instructions for using any of the antibodies or polyclonal antibodies described herein for the purpose of binding to SNV antigen to form an immunological complex and detecting the formation of the immunological complex such that the presence or absence of the immunological complex correlates with presence or absence of Sin Nombre virus antigens in the sample. Examples of containers include multiwell plates which allow simultaneous detection of Sin Nombre virus in multiple samples.

Further, the invention contemplates a method for producing pseudotyped viruses for use in serologic assays or delivery of gene therapies to endothelial cells targeted by hantavirus glycoproteins. The invention as used for this purpose would comprise the following steps. The plasmid pWRG/SN-M(opt) or derivative thereof would be used to transfect cells or stably transform cells. Cells expressing the Sin Nombre glycoproteins could then be infected with viruses engineered to produce progeny that incorporate the Sin Nombre glycoproteins into progeny virus surface envelopes. Pseudotype virus systems include retrovirus systems and vesicular stomatitis virus systems. Pseudotypes have been produced using the hantavirus full-length M gene plasmids, including pWRG/SN-M(opt). The pseudotypes can be used for testing for neutralizing antibodies. They also may be used to deliver genes to endothelial cells in a clinical setting. For example, gene therapy viruses containing the Sin Nombre glycoproteins on their surface will target to certain endothelial cells.

The invention also entails a therapeutic composition for ameliorating symptoms of Sin Nombre virus infection. The composition includes polyclonal or monoclonal antibodies specifically raised against one of SEQ ID NO:1, SEQ ID NO:2 or SEQ ID NO:3. The composition may be combined with a pharmaceutically acceptable carrier and/or an adjuvant, such as the examples as described herein.

Other embodiments are discussed below. The invention is described in further detail by the non-limiting examples and text below.

BRIEF DESCRIPTION OF THE FIGURES

FIG. 1. Hantavirus neutralizing antibodies produced in rabbits vaccinated with full-length hantavirus M gene-based DNA vaccines using muscle electroporation. A) Hantaan, Puumala, and Andes DNA vaccines. Groups of 3 rabbits were vaccinated with either the Hantaan DNA vaccine, pWRG/HTN-M(x) (described in U.S. Pat. No. 7,217,812), or the Puumala DNA vaccine, pWRG/PUU-M(s2) (described in U.S. Patent Publication No. 20100323024) on days 0, 14, 28, and 32 by muscle electroporation (Invoio Elgen device, dose was 0.4 mg of DNA per injection. Sera were collected on weeks 0, 28, 56, and 116 and tested in homotypic PRNT. Symbols represent the mean of two separate PRNT±SE. B) The same data from panel A were combined to show mean titers for the groups. In addition, published data from rabbits vaccinated with the Andes DNA vaccine, pWRG/AND-M, are included. Note the vaccination days were different for the Andes DNA vaccine (shown in grey arrows). C) Sin Nombre DNA vaccines. The first generation SNV full-length M gene based DNA vaccine, pWRG/SNV-M(2a), was tested in three rabbits. The animals were vaccinated four times (arrows) and sera were tested for SNV neutralizing antibodies. High-titer neutralizing antibody could be produced after multiple vaccinations. The second genearation plasmid, pWRG/SN-M(opt), was tested in rabbits. Rabbits were vaccinated on days 0, 28, 56 and 84. Sera collected on the indicated days were tested for SNV neutralizing antibodies. High-titers were achieved after 2, or fewer, vaccinations (sera from day 28 was not collected). D) The same data from panel C were combined to show mean titers for the groups±SE.

FIG. 3A. The titers are the reciprocal of the highest dilution reducing the number of plaques in the media alone wells by 80%.

FIG. 3B. Raw plaque numbers for one representative rabbit are shown before vaccination, after 2 (day 56) and after 3 (day 70). Note that there is 100% neutralization out to a 1:10,240 dilution for the day 70 serum. The numbers 6281, 6282, 6283, and 5284 are designations for the different rabbits vaccinated.

FIG. 3. HPS vaccine. Plasmid mixtures were tested in rabbits using muscle electroporation (EP). Three rabbits were vaccinated by muscle EP on day 0, 21, and 42 with a 1:1 mixture of the pWRG/SN-M(opt) and pWRG/AND-M DNA (described in U.S. Pat. No. 7,217,81.2) vaccine plasmids. Sera were collected at the indicated time points and plaque reduction neutralization tests (PRNT) were performed. Neutralizing antibodies were produced against both SNV and ANDV after a single vaccination. Overall, the neutralizing antibody titers were greater against SNV (panel A) than ANDV (panel B). Device=Ichor Tri-grid device; Dose=2.0 mg mixed DNA/injection, 1 injection per vaccination. (Unpublished) The numbers 6214, 6215, and 6216 are designations for the different rabbits vaccinated.

FIG. 5. PRNT80 GMT against HTNV, PUUV, SNV, and ANDV for each DNA vaccine formulation after 1, 2, or 3 vaccinations are shown. These data are from the same experiment shown in FIG. 2; however PRNT80 GMT are shown here. PRNT80 titers are a more stringent measure of neutralizing antibodies that PRNT50. The HFRS mix (pWRG/HTN-M[x] and pWRG/PUU-M[s2]) produced GMTs>100 against HTNV and PUUV. The HPS mix (pWRG/SN-M[opt] and pWRG/AND-M) produced GMTs>100 against SNV and ANDV. And the HFRS/HPS mix "pan-hantavirus" produced GMTs>100 against all four hantaviruses. PUUV PRNT endpoints after 1 vaccination were not determined beyond 640 (indicated by≥). <indicates GMT was below detection. These data demonstrate the utility of using the SN DNA vaccine as part of HPS vaccine or a pan-hantavirus DNA vaccine.

FIG. 6. pWRG/SN-M(opt) DNA vaccine is immunogenic and protective in hamsters. Groups of 7-8 hamsters received 2 vaccinations (week 0, 3), or three vaccinations (week 0, 3, 6) with pWRG/SN-M(opt), or 3 vaccinations with a negative control DNA vaccine, or no vaccine. Vaccinations were performed using a gene gun. A) Sera collected on week 9 were tested for SNV neutralizing antibody by SNV PRNT. Each symbol represents the $PRNT_{50}$ titer of an individual hamster. The geometric mean titer and 95% confidence interval for each group are shown. The limit of detection was a titer of 20 (dashed line). Seroconversion rates after 2 or 3 vaccinations were 62.5% (5 of 8) and 71.4% (5 of 7), respectively. The immune response was lower than what we observed in rabbits using electroporation, but was nevertheless evidence that the pWRG/SN-M(opt) plasmid was immunogenic in hamsters. B) The hamsters were challenged with 200 pfu of SNV by the intramuscular route on week 11. Sera were collected on week 16 and tested by ELISA for evidence of SNV infection (note that SNV infects hamsters but is not lethal). A positive ELISA indicates the hamsters were infected with SNV (i.e., not protected). 2 vaccinations with pWRG/SN-M(opt) protected 62.5% of the hamsters and 3 vaccinations protected 100% of the hamsters. All of the negative control hamsters were infected. <indicates titer was below level of detection.

Figure 8:
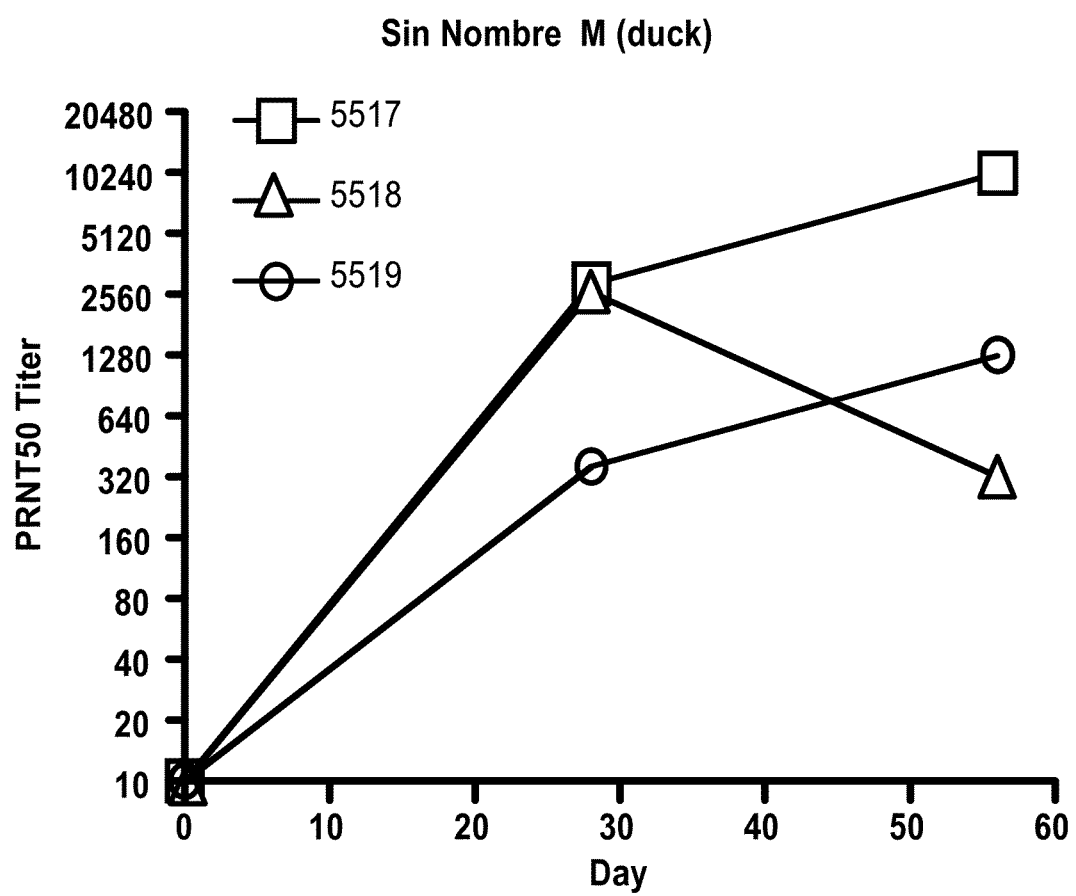

FIG. 7. The pWRG/SN-M(opt) plasmid was used to make pseudovirions that were specifically neutralized by rabbit sera containing SNV neutralizing antibodies. 293T cells were transfected with pWRG/SN-M(opt) and then, after 24 hr, were "infected" with recombinant vesicular stomatitis virus (VSV) that had the G protein deleted and replaced with the Renilla luciferase gene (VSV deltaG luciferase reporter core virus system was provided by Robert Doms, University of Pennsylvania). After 48 hr at 37 C, the supernatant was harvested and pseudovirion particles were purified on a sucrose gradient. Two different preparations of pseudovirions (prep 1, top panel; prep 2, bottom panel) where then mixed with serial dilutions of naïve rabbit sera, anti-SNV rabbit sera, or anti-VSV-G antibody (as control) and incubated for 1 hr at 37 C. The mixtures were then used to infect BHK cells in a 96-well format for 24 hours. Cell lysates were harvested, combined with luciferase substrate, and the luciferase reporter activity in Relative Luminescent Units (RLU) was measured using a luminometer. Symbols represent the average value of duplicates. The data demonstrate that the anti-SNV rabbit sera, but not the other sera, reduced the RLU activity (neutralized the pseudovirions) in a dose dependent manor. This assay can be used to measure SNV neutralizing antibodies in any sera including humans vaccinated with candidate HPS vaccines, or naturally infected with hantaviruses FIG. 8. The nonoptimized version of the Sin Nombre DNA vaccine, pWRG/SN-M(2a),was tested for the capacity to produce neutralizing antibodies in an avian species. Ducks were vaccinated with 0.4 mg of plasmid DNA using muscle electroporation on days 0, 14, and 42. Sera was collected on days 0, 28, and 56 and tested for SNV neutralizing antibodies by PRNT. Higher titers are expected using the optimized pWRG/SN-M(opt) plasmid. These data demonstrate that the Sin Nombre DNA vaccine can be used to produce high titer neutralizing antibodies in avian species. This antibody is reasonably expected to be purified from eggs and may be used in humans or other mammals as post-exposure prophylactics or therapeutics, or as diagnostic reagents. The duck IgY naturally loses the Fc fragment of the antibody and this, it is believed, will make the molecule less reactogenic when used in a human as a therapeutic or post-exposure prophylactic.

DETAILED DESCRIPTION OF THE INVENTION

Supplemental to the previous description of the invention, the following further details are provided.

The inventor has created a novel, synthetic codon optimized Sin Nombre virus full-length M gene, ORF plus flanking sequences, and ORF, that are each stably maintained in a DNA vaccine plasmid, and elicit good neutralizing antibodies in animal models. Heretofore, there was no full length Sin Nombre M gene clone stably inserted it on an expression plasmid, which could be successfully expressed. Likewise, this is the first time any vaccine, of any kind, has been shown to elicit high titer neutralizing antibodies and protect against SNV infection in an animal model.

The inventor cloned the full-length M gene from SNV, strain CC107 into a DNA vaccine vector (i.e., RNA was purified, reverse transcribed to cDNA, PCR amplified, and cloned into a DNA vaccine plasmid [pWRG7077]). Ultimately, the inventor was able to produce a unique plasmid with an intact open reading frame (designated pWRG/SN-M (2a) or "M(2a)"). It was confirmed that this plasmid could produce the Gn and Gc protein in cell culture. pWRG/SN-M (2a) was tested for immunogenicity in rabbits using muscle electroporation technology. Three rabbits were vaccinated on weeks 0, 2, 4, 6 with 0.4 mg of DNA per vaccination. Sera were collected on weeks 0, 4, and 8. PRNT were performed to detect SNV neutralizing antibodies. The data demonstrated that high-titer neutralizing antibody were produced after 4 vaccinations (FIG. 1). The titers reached were over 10,000, which is considered are similar to those produced in person who have developed HPS and survived. In the art of immunology, and especially regarding hantaviruses, any titer over 100 would be considered good, and useful for vaccine purposes. This was the first time high-titer SNV neutralizing antibodies were ever produced by any vaccine, confirming the uniqueness of the M(2a) plasmid. Nevertheless, one undesirable result was that the M(2a) required more vaccinations to raise high-titers than the inventor's previous hantavirus vaccines, namely the HTNV , PUUV, or ANDV M gene-based DNA vaccines.

Figure 2A:
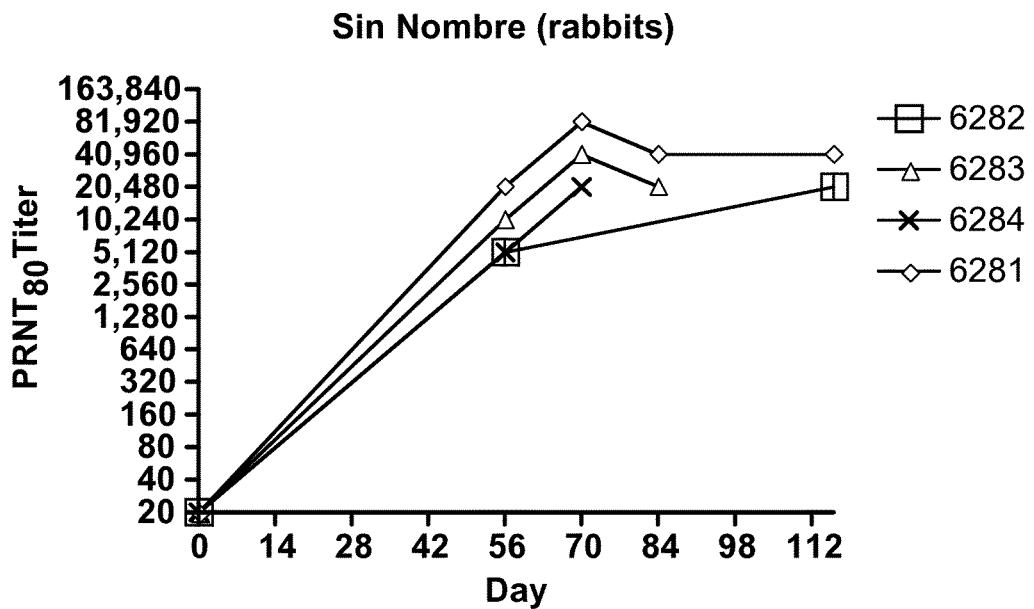
FIG. 2. Neutralizing antibody data from rabbits vaccinated with pWRG/SN-M(opt) (also designated as pWRG/SN-M(opt)). Rabbits were vaccinated on days 0, 28, 56 and 84. Sera collected on days 0, 56, and 70 where tested for Sin Nombre virus neutralizing antibodies by plaque reduction neutralization test (PRNT). The neutralizing antibody titers are shown.
Figure 2B:
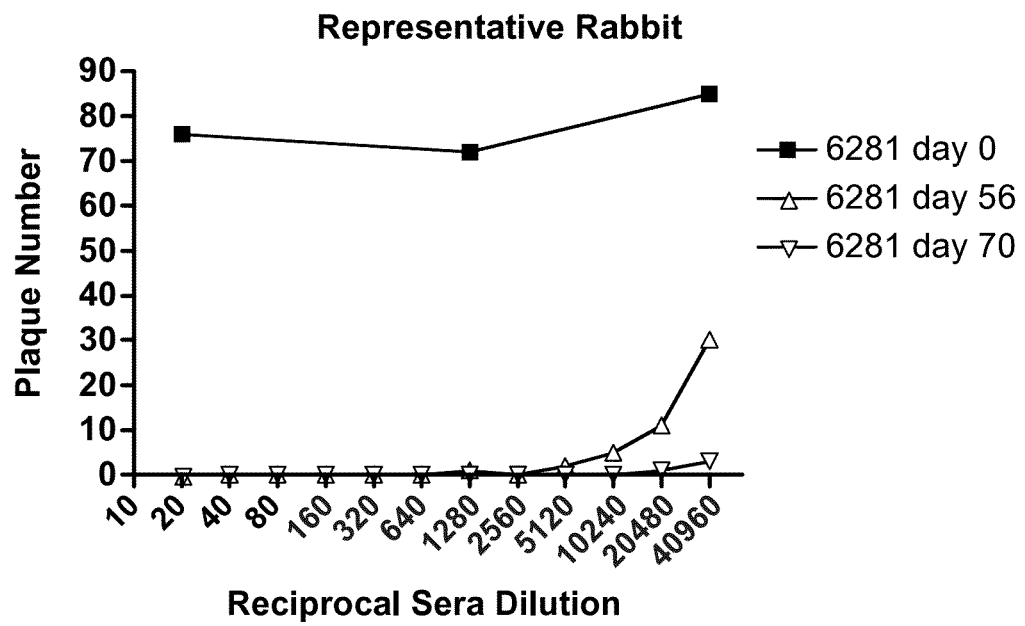
Figure 4B:
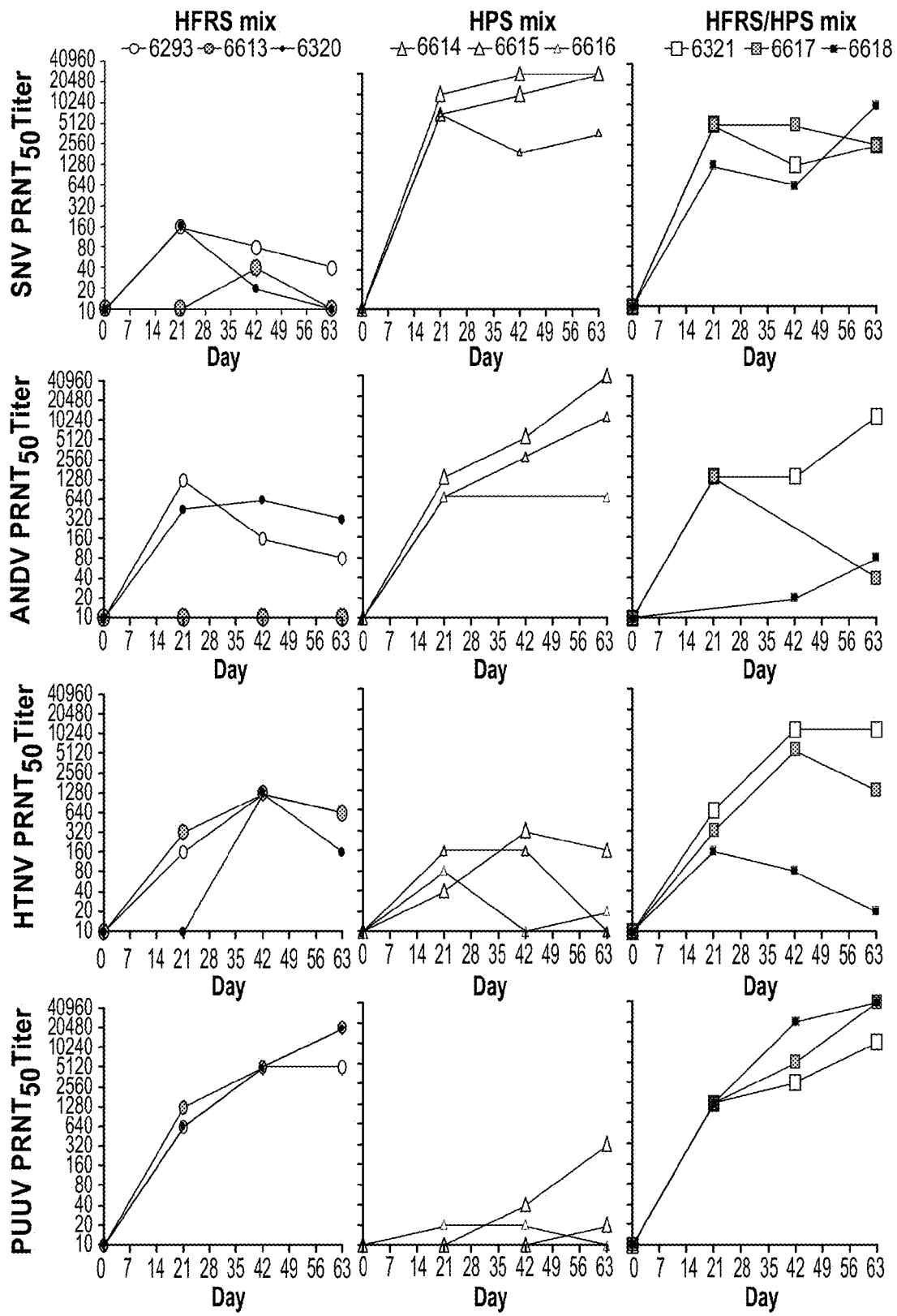
FIG. 4. Mixed hantavirus DNA vaccines are feasible. Three mixtures of hantavirus DNA vaccine plasmids delivered by muscle electroporation were tested in rabbits. A) Experimental design. Groups of three rabbits were vaccinated three times by muscle electroporation using the Ichor Tri-grid at three-week intervals. The HFRS mixture was comprised of equal volumes of Hantaan and Puumala DNA vaccine plasmids, pWRG/HTN-M(x) and pWRG/PUU-M(s2), respectively. The HPS mixture was comprised of equal volumes of Andes and Sin Nombre DNA vaccine plasmids, pWRG/AND-M and pWRG/SN-M(opt), respectively. The HFRS/HPS mixture was comprised of equal volumes of the Hantaan, Puumala, Andes, and Sin Nombre DNA vaccine plasmids. The mixtures contained 1 mg of each plasmid per dose. B) Neutralizing antibody titers for individual rabbits are shown. The virus used in the neutralization test is shown on the y-axis. Sera from days 0, 21, 42, and 63 were tested. C) Mean neutralizing titers for each group plus/minus standard error. The data demonstrate that it is possible to mix hantavirus DNA vaccines into a single-injection vaccine and produce neutralizing antibodies against multiple hantaviruses. The HFRS DNA vaccine was more effective at neutralizing Puumala virus and Hantaan virus and the HPS DNA vaccine was more effective at neutralizing Andes virus and Sin Nombre virus. The HFRS/HPS DNA vaccine elicited neutralizing antibodies against all four hantaviruses after a single vaccination for all but one rabbit.
Figure 4C:
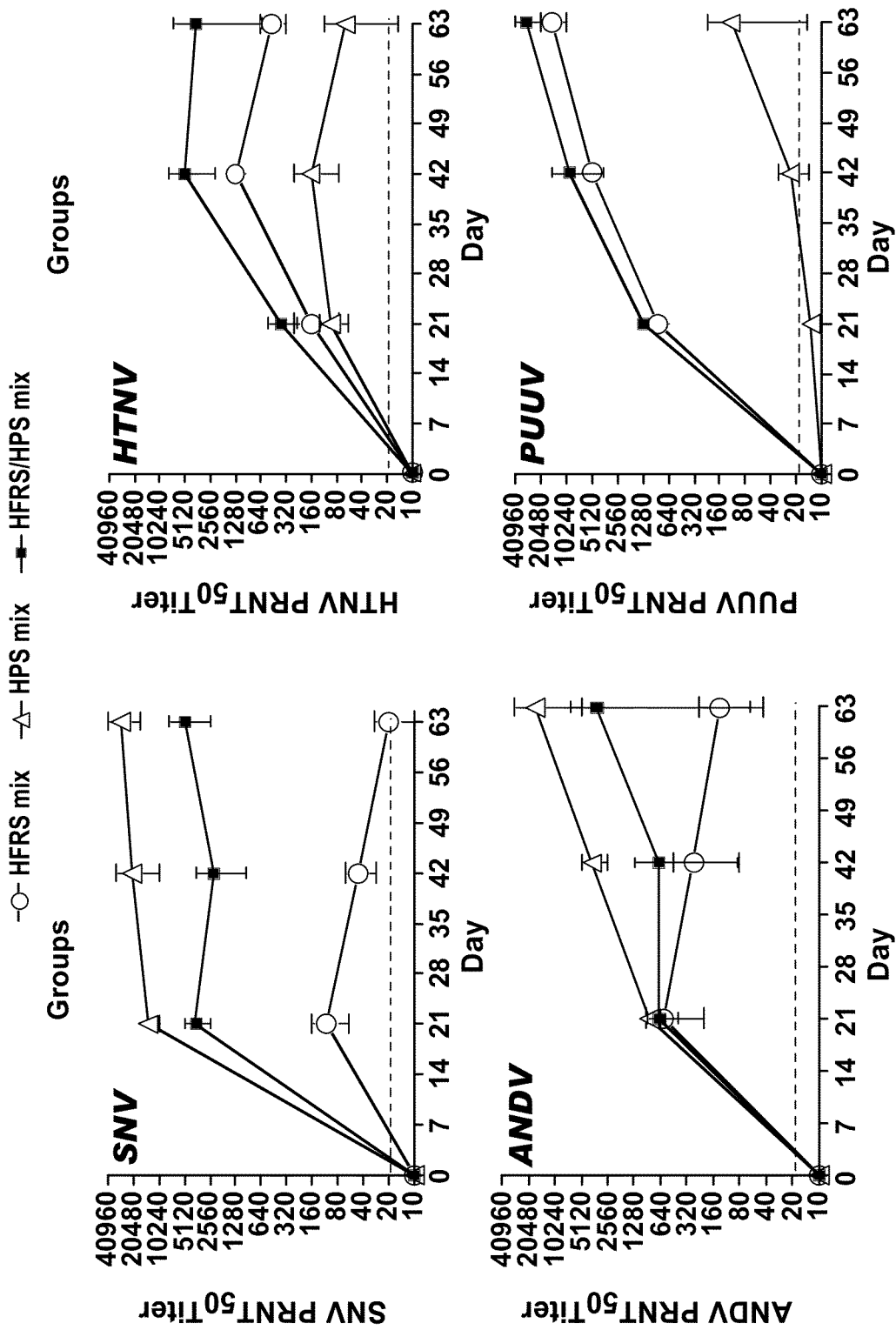
Figure 6A:
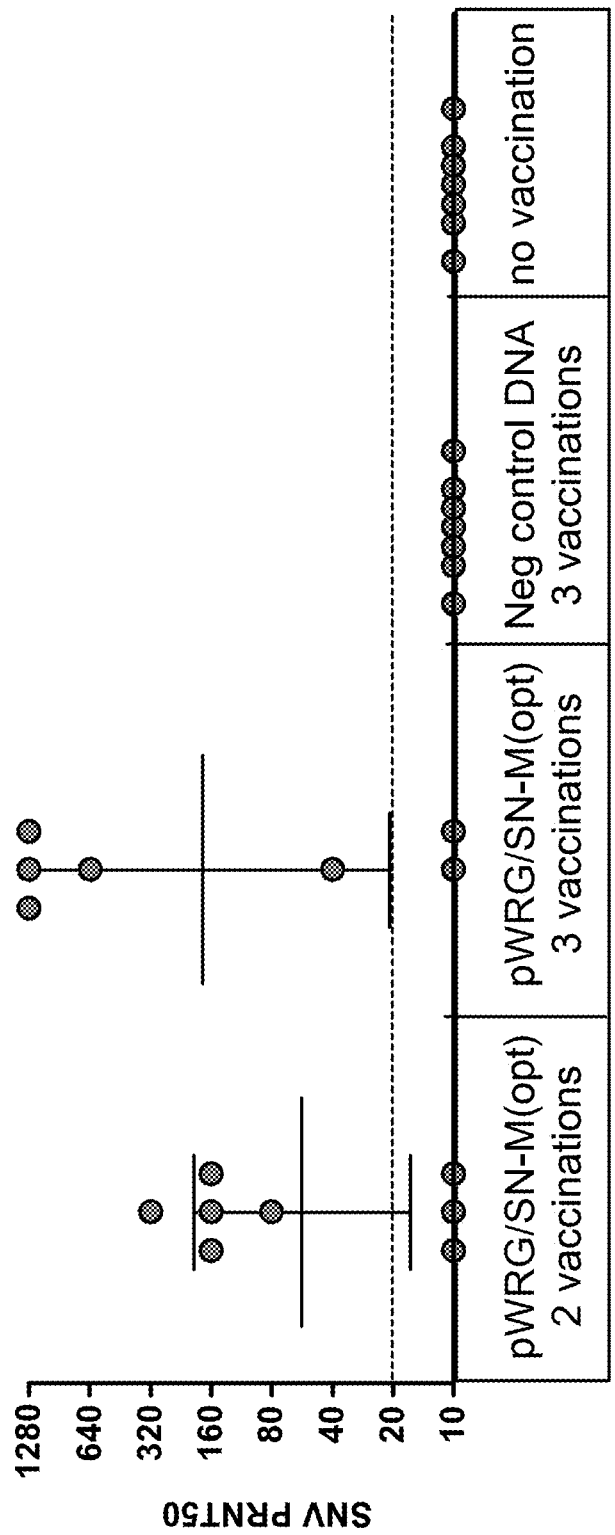

In an attempt to improve immunogenicity and potency, the M(2a) plasmid was refined by (1) first determining any possible flaws in the open reading frame and (2) obtaining the synthesis of a codon-optimized version of the SNV M gene. The inventor analyzed the M gene sequence in pWRG/SN-M (2a) and discovered amino acids that were unique to the clone (i.e., not in published GeneBank SNV M sequences) (Table 1). He identified consensus amino acids at these positions and then had an optimized version of this gene synthesized (work contracted to GeneArt)(Table 2). Next, the synthetic M gene was cloned into a DNA vaccine vector and the resultant plasmid was named pWRG/SN-M(opt) (or "M(opt)"). The sequence of the pWRG/SN-M(opt) plasmid is given in SEQ ID NO:1. M(opt) was tested for a capacity to elicit neutralizing antibodies by vaccinating rabbits with the pWRG/SN-(opt) using muscle electroporation. Four rabbits were vaccinated on weeks 0, 4, and 8 with 1 mg of DNA per vaccination. Sera were collected on weeks 0, 8 and 10. PRNT were performed to detect SNV neutralizing antibodies. Very high titers of SNV neutralizing antibodies were produced after only 2 vaccinations (week 8 sera) with pWRG/SN-M(opt) (FIG. 2) After 3 vaccinations (week 10 sera) there was 100% neutralization in all four rabbits even when the sera was diluted ≥1:5,000. This was a significant improvement over the M(2a) results—2 vaccinations is considered acceptable to be convenient enough for human or animal use.

Having found the pWRG/SN-M(opt) to be a potent DNA vaccine, the inventor next combined the SNV DNA vaccine with the pWRG/AND-M. A mixture of the two plasmids was used to vaccinate rabbits using muscle electroporation. High titer neutralizing antibodies against both SNV and ANDV were produced after 1 or 2 vaccinations (FIG. 3). The SNV neutralizing activity was especially potent (titers >10,000 after 1 vaccination). Thus, the combination of the pWRG/SN-M(opt) DNA vaccine and pWRG/AND-M DNA vaccine effectively elicited high-titer neutralizing antibodies against the most prevalent and lethal hantavirus in North and South America. The novelty and potency of this SNV DNA vaccine was surprising and unexpected.

In summary, the inventor produced two plasmids that elicited high titer neutralizing antibodies against SNV in animal models. Thus, one point of novelty of the invention is that it elicits Sin Nombre virus neutralizing antibodies, and with significantly high titers. To the best of the inventor's knowledge, there is no other SNV vaccine that elicits antibodies that directly neutralize Sin Nombre virus.

Vaccines and Immunogenic Compositions

To summarize, the vaccines and immunogenic compositions comtemplated by this invention include: (1) Sin Nombre virus vaccines and immunogenic compositions; (2) Sin Nombre virus+other HPS viruses (e.g., Andes virus) vaccines and immunogenic compositions; (3) Sin Nombre virus vaccines and immunogenic compositions+HFRS viruses (e.g., Puumula and Hantaan viruses) vaccines and immunogenic compositions; and (4) Sin Nombre virus+other HPS viruses (e.g., Andes virus) vaccines and immunogenic compositions+ HFRS viruses (e.g., Puumula and Hantaan viruses) vaccines and immunogenic compositions. These vaccines and immunogenic compositions, when transfected into mammalian cells, result in the expression of proteins that mimic the Gn and Gc surface glycoproteins of SNV and the other hantaviruses targeted. When these DNA vaccines or immunogenic compositions are introduced into the cells of a vaccinee, the vaccinee produces a neutralizing antibody response against SNV, and, if relevant, the other hantavirus(es). Neutralizing antibody responses are sufficient to confer protection against SNV and the other hantaviruses. Thus, SEQ ID NO:1, SEQ ID NO:2 and SEQ ID NO:3, and derivatives thereof, represent a candidate vaccine for the prevention of HPS caused by SNV. Moreover, these novel sequences, and derivatives thereof, can be used to generate anti-SNV immunotherapeutics and diagnostic antibodies in animals. (The term transfected is used herein to refer to cells which have incorporated the delivered foreign DNA vaccine, whichever delivery technique is used.)

As noted above, there is no vaccine or drug to prevent or treat HPS. One of the embodiments of the invention described herein is a DNA vaccine based on the M-gene segment of Sin Nombre virus. The M genome segment encodes the two proteins found on the virus surface.

One embodiment of the invention encompasses DNA vaccines. DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

The DNA vaccine according to the present invention is inherently safe, is not painful to administer, and should not result in adverse side effects to the vaccinated individual. In addition, the invention does not require growth or use of Sin Nombre virus, which is a biosafety level 3 (BSL-3) virus, and is a BSL-4 virus if the virus is grown to high levels or used in animals.

In order to achieve the immune response sought, a DNA vaccine construct capable of causing transfected cells of the vaccinated individual to express one or more major viral antigenic determinant is necessary. This can be done by identifying regions of the viral genome which code for viral glycoproteins or capsid components, and joining such coding sequences to promoters capable of expressing the sequences in cells of the vaccinee. Alternatively, the viral genome itself, or parts of the genome, can be used.

In a preferred embodiment, the vaccine is a plasmid based codon-optimized Sin Nombre virus (SNV) M gene open reading frame. The M gene encodes for two proteins that form a part of the viral capsid. In nature these are glycosylated during synthesis in mammalian cells which would occur after vaccination. SNV is one of several viruses that cause Hantavirus Pulmonary Syndrome, a disease with high mortality (20-50%). There have been several hundred cases in the Americas over the past several years. This vaccine has been shown to induce high neutralizing antibody titers in animals and therefore would be useful for a human vaccine. Two hantavirus DNA vaccines -Hantaan and Puumala—have been shown to induce neutralizing antibodies in human clinical trials. (Presentation given: "Preclinical and Phase 1 Clinical Studies of a DNA Vaccine for HFRS Caused by Hantaviruses" J. Hooper, to the American Society of Microbiology Biodefense Meeting, held in Baltimore, February, 2010)

As noted above, attempts to produce SNV vaccine that produce neutralizing antibodies against SNV have been unsuccessful. Here, for the first time, the inventor has synthesized a codon-optimized full-length M gene open reading frame and cloned it into a DNA vaccine expression vector (e.g., pWRG-SN-M(opt)). The nucleotide sequences are completely unique because the ORF has been optimized. Regarding the preferred embodiment pWRG/SN-M(opt), hamsters and rabbits vaccinated with pWRG/SN-M(opt) using a gene gun developed neutralizing antibodies as measured by plaque reduction neutralization test (PRNT) with $PRNT_{50}$ titers ranging from 10,240—ver 81,920 in rabbits by electroporation; in hamsters, less than 20-1,280 by gene gun. This is believed to be the first candidate SNV vaccine that successfully elicits neutralizing antibodies against SNV.

In its preferred vaccine embodiment, the SNV virus M gene-based DNA vaccine is a plasmid that consists of a well-characterized backbone that enables expression of the above-described synthetic, codon-optimized, SNV virus full-length M gene, or the ORF with or without flanking sequences. Preferred examples are SEQ ID NO:1, SEQ ID NO:2 and SEQ ID NO:3. It can be used in other vaccine systems and systems for generating SNV neutralizing antibodies.

In this application we describe the elicitation of protective immunity to SNV alone or with other hantaviruses by DNA vaccines. The gene(s) of interest, in our case, a synthetic Sin Nombre virus M gene having at least one of the sequences identified herein as SEQ ID NO:1, SEQ ID NO:2, and SEQ ID NO:3, is controlled by a mammalian or virus promoter (e.g., the cytomegalovirus immediate early promoter followed by intron A) that facilitates expression of the naked DNA gene product(s) within the vaccinee's cells. Preferably, Intron A is included. It is preferred even to use pWRG/SN-M(opt) as the DNA vaccine plasmid. This intracellular expression can elicit both humoral and cell-mediated immune responses (Robinson and Torres, 1997, supra; and Gregoriadis, 1998, supra).

Methods of DNA delivery include needle inoculation, needle-free jet injection, oral or pulmonary delivery, and inoculation by particle bombardment (i.e., gene gun) and electroporation—by well-known methods for each. Needle inoculation and needle-free jet injection may be made with or without electroporation. Delivery may be intramuscular or intradermal, as appropriate.

A suitable construct for use in the method of the present invention is pWRG7077 (4326 bp)(PowderJect Vaccines, Inc., Madison, Wis.),. pWRG7077 includes a human cytomegalovirus (hCMV) immediate early promoter (IE) and a bovine growth hormone polyA addition site. Between the promoter and the polyA addition site is Intron A, a sequence that naturally occurs in conjunction with the hCMV IE promoter that has been demonstrated to increase transcription when present on an expression plasmid. Downstream from Intron A, and between Intron A and the polyA addition sequence, are unique cloning sites into which the hantavirus M DNA can be cloned. Also provided on pWRG7077 is a gene that confers bacterial host-cell resistance to kanamycin. Any of the fragments that encode hantavirus Gn and/or Gc or nucleocapsid peptides can be cloned into one of the cloning sites in pWRG7077, using methods known to the art.

The DNA can be delivered by injection into the tissue of the recipient, oral or pulmonary delivery and inoculation by particle bombardment (i.e., gene gun). Any of these methods can be used to deliver DNA as long as the DNA is expressed and the desired antigen is made in the cell. Two methods are exemplified in this application, both shown to be successful in eliciting a protective immune response in the vaccinee.

In one aspect of the invention, the DNA vaccine is delivered by coating a small carrier particle with the DNA vaccine and delivering the DNA-coated particle into an animal's epidermal tissue via particle bombardment. This method may be adapted for delivery to either epidermal or mucosal tissue, or delivery into peripheral blood cells, and thus may be used to induce humoral, cell-mediated, and secretory immune reponses in the vaccinated individual.

To deliver DNA vaccines by particle bombardment, we chose to use the PowderJect-XR™ gene gun device described in WO 95/19799, 27 Jul. 1995. Other instruments are available and known to people in the art. This instrument, which delivers DNA-coated gold beads directly into epidermal cells by high-velocity particle bombardment, was shown to more efficiently induce both humoral and cell-mediated immune responses, with smaller quantities of DNA, than inoculation of the same DNAs by other parenteral routes (Eisenbraun, M. et al., 1993, DNA Cell. Biol. 12: 791; Fynan, E. F. et al., 1993, Proc. Natl. Acad. Sci. USA 90: 11478; Haynes, J. R. et al., 1994, AIDS Res. Hum. Retroviruses 10: Suppl. 2:S43; Pertmer, T. M. et al., 1995, Vaccine 13: 1427). Epidermal inoculation of the DNA candidate vaccines also offers the advantages of gene expression in an immunologically active tissue that is generally exfoliated within 15 to 30 days, and which is an important natural focus of viral replication after tick-bite (Bos, J. D., 1997, Clin. Exp. Immunol. 107 Suppl. 1:3; Labuda, M. et al., 1996, Virology 219:357; Rambukkana, A. et al., 1995, Lab. Invest. 73:521; Stingl, G., 1993, Recent Results Cancer Res. 128:45; Evans et al., Vaccine, 2009, Vol.27(18), pp.2506-2512; Yager et al., Expert Rev. Vaccines, 2009, Vol.8(9), pp.1205-1220).

The technique of accelerated particles gene delivery or particle bombardment is based on the coating of DNA to be delivered into cells onto extremely small carrier particles, which are designed to be small in relation to the cells sought to be transformed by the process. The DNA sequence containing the desired gene can be simply dried onto a small inert particle. The particle may be made of any inert material such as an inert metal (gold, silver, platinum, tungsten, etc.) or inert plastic (polystyrene, polypropylene, polycarbonate, etc.). Preferably, the particle is made of gold, platinum or tungsten. Most preferably, the particle is made of gold. suitably, the particle is spherical and has a diameter of 0.5 to 5 microns, preferably 1 to 3 microns.

The DNA sequence containing the desired gene prepared in the form suitable for gene introduction can be simply dried onto naked gold or tungsten pellets. However, DNA molecules in such a form may have a relatively short period of stability and may tend to degrade rather rapidly due to chemical reactions with the metallic or oxide substrate of the particle itself Thus, if the carrier particles are first coated with an encapsulating agent, the DNA strands have greatly improved stability and do not degrade significantly even over a time period of several weeks. A suitable encapsulating agent is polylysine (molecular weight 200,000) which can be applied to the carrier particles before the DNA molecules are applied. Other encapsulating agents, polymeric or otherwise, may also be useful as similar encapsulating agents, including spermidine. The polylysine is applied to the particles by rinsing the gold particles in a solution of 0.02% polylysine and then air drying or heat drying the particles thus coated. Once the metallic particles coated with polylysine were properly dried, DNA strands are then loaded onto the particles.

The DNA is loaded onto the particles at a rate of between 0.5 and 30 micrograms of DNA per milligram of gold bead spheres. A preferable ratio of DNA to gold is 0.5 5.0 ug of DNA per milligram of gold. A sample procedure begins with gamma irradiated (preferably about 30 kGy) tefzel tubing. The gold is weighed out into a microfuge tube, spermidine (free base) at about 0.05 M is added and mixed, and then the DNA is added. A 10% CaCI solution is incubated along with the DNA for about 10 minutes to provide a fine calcium precipitate. The precipitate carries the DNA with it onto the beads. The tubes are microfuged and the pellet resuspended and washed in 100% ethanol and the final product resuspeded in 100% ethanol at 0.0025 mg/ml PVP. The gold with the DNA is then applied onto the tubing and dried.

The general approach of accelerated particle gene transfection technology is described in U.S. Pat. No. 4,945,050 to Sanford. An instrument based on an improved variant of that approach is available commercially from PowderJect Vaccines, Inc., Madison Wis., and is described in WO 95/19799. All documents cited herein supra and infra are hereby incorporated in their entirety by reference thereto. Briefly, the DNA-coated particles are deposited onto the interior surface of plastic tubing which is cut to a suitable length to form sample cartridges. A sample cartridge is placed in the path of a compressed gas (e.g., helium at a pressure sufficient to dislodge the particles from the cartridge e.g., 350 400 psi). The particles are entrained in the gas stream and are delivered with sufficient force toward the target tissue to enter the cells of the tissue. Further details are available in the published apparatus application.

The coated carrier particles are physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in prokaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a DNA vaccine capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

A DNA vaccine can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response.

To obtain additional effectiveness from this technique, it may also be desirable that the genes be delivered to a mucosal tissue surface, in order to ensure that mucosal, humoral and cellular immune responses are produced in the vaccinated individual. There are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

Gene gun-based DNA immunization achieves direct, intracellular delivery of DNA, elicits higher levels of protective immunity, and requires approximately three orders of magnitude less DNA than methods employing standard inoculation.

Moreover, gene gun delivery allows for precise control over the level and form of antigen production in a given epidermal site because intracellular DNA delivery can be controlled by systematically varying the number of particles delivered and the amount of DNA per particle. This precise control over the level and form of antigen production may allow for control over the nature of the resultant immune response.

The invention further covers passive vaccines for treating or preventing Sin Nombre virus infections comprising a therapeutically or prophylactically effective amount of the antibodies of the present invention which protect against Sin Nombre virus disease in combination with a pharmaceutically acceptable carrier or excipient. As described in greater detail herein, the present inventor has found that serum from a vaccinee immunized with a DNA vaccine comprising the Sin Nombre virus M segment described above contains antibodies able to neutralize Sin Nombre virus and display in vitro and in vivo Sin Nombre virus neutralization properties.

The invention also contemplates a new recombinant DNA vaccine approach that involves vaccination with naked DNA expressing individual Sin Nombre virus genome segment cDNAs. Naked DNA vaccination involves delivery of plasmid DNA constructs with a gene(s) of interest into the tissue of the vaccinee (reviewed in Robinson and Torres, 1997, *Semin. Immunol.* 9, 271-283; and Gregoriadis, 1998, *Pharm. Res.* 15, 661-670). DNA vaccination mimicks the de novo antigen production and MHC class I-restricted antigen presentation obtainable with live vaccines, without the risks of pathogenic infection. Also, this DNA vaccine approach allows delivery to mucosal tissues which may aid in conferring resistance to viral introduction since entry of the virus may be through mucosal tissues.

This vaccine was also tested for a capacity to elicit neutralizing antibodies in rabbits using muscle electroporation as the means of vaccine delivery. The electroporation device and dose of DNA delivered is compatible with human use (Ichor Tri-grid device). Well-known methods of electroporation are effective for this DNA vaccine. For instance, Hooper et al. (February 2008), describes methods useful for this. (Hooper et al., "Immune Serum Produced by DNA Vaccination Protects Hamsters against Lethal Respiratory Challenge with Andes Virus", J. Virology, February 2008, Vol. 82, No. 3, pp.1332-1338; also see, van Drunen, et al., Expert Rev. Vaccines, 2010, Vol.9(5), pp.503-517). In addition, mammals such as rabbits can be vaccinated by muscle electroporation with a DNA vaccine plasmid such as pWRG/SN-M(opt) to rapidly generate sera containing high-titer SNV neutralizing antibodies. Sera can be collected and tested for neutralizing antibodies by PRNT.

Vaccination with the SNV M gene-based DNA vaccine, called pWRG/SN-M(opt), elicits high-titer neutralizing antibodies. It is widely believed in the field that neutralizing antibodies are surrogate endpoints of protective immunity, so any vaccine that elicits high-titer neutralizing antibodies has utility as a vaccine. This vaccine could be used to immunize against North American HPS. In addition, it could be combined with other hantavirus DNA vaccines to create a pan-hantavirus vaccine. In short, the plasmid containing the synthetic codon-optimized SNV M gene is exceedingly effective at eliciting neutralizing antibodies.

For a HPS vaccine composition or immunogenic composition, the composition will have at least one of the above-described SNV sequences (SEQ ID NO:1, SEQ ID NO:2 or SEQ ID NO:3), plus at least one other M-gene (e.g., whole full-length or ORF or ORF plus flanking sequences) from a different (non-SNV) HPS. Examples of other HPS viruses include Black Creek Canal virus, Bayou virus, New York virus, Andes virus, and Laguna Negra virus. A preferred HPS vaccine or immunogenic composition comprises at least one of the above-described SNV sequences, and the Andes M-gene—preferably plasmid pWRG/AND-M(x) (SEQ ID NO:10), below:

```
gggggggggg ggcgctgagg tctgcctcgt gaagaaggtg    40
ttgctgactc ataccaggcc tgaatcgccc catcatccag    80
ccagaaagtg agggagccac ggttgatgag agctttgttg   120
taggtggacc agttggtgat tttgaactt tgctttgcca   160
cggaacggtc tgcgttgtcg ggaagatgcg tgatctgatc   200
cttcaactca gcaaaagttc gatttattca acaaagccgc   240
cgtcccgtca agtcagcgta atgctctgcc agtgttacaa   280
ccaattaacc aattctgatt agaaaaactc atcgagcatc   320
aaatgaaact gcaatttatt catatcagga ttatcaatac   360
catatttttg aaaaagccgt ttctgtaatg aaggagaaaa   400
ctcaccgagg cagttccata ggatggcaag atcctggtat   440
cggtctgcga ttccgactcg tccaacatca atacaaccta   480
ttaatttccc ctcgtcaaaa ataaggttat caagtgagaa   520
atcaccatga gtgacgactg aatccggtga gaatggcaaa   560
agcttatgca tttctttcca gacttgttca acaggccagc   600
cattacgctc gtcatcaaaa tcactcgcat caaccaaacc   640
gttattcatt cgtgattgcg cctgagcgag acgaaatacg   680
cgatcgctgt taaaaggaca attacaaaca ggaatcgaat   720
```

-continued

```
gcaaccggcg caggaacact gccagcgcat caacaatatt       760
ttcacctgaa tcaggatatt cttctaatac ctggaatgct       800
gttttcccgg ggatcgcagt ggtgagtaac catgcatcat       840
caggagtacg gataaaatgc ttgatggtcg gaagaggcat       880
aaattccgtc agccagttta gtctgaccat ctcatctgta       920
acatcattgg caacgctacc tttgccatgt ttcagaaaca       960
actctggcgc atcgggcttc ccatacaatc gatagattgt      1000
cgcacctgat tgcccgacat tatcgcgagc ccatttatac      1040
ccatataaat cagcatccat gttggaattt aatcgcggcc      1080
tcgagcaaga cgtttcccgt tgaatatggc tcataacacc      1120
ccttgtatta ctgtttatgt aagcagacag ttttattgtt      1160
catgatgata tatttttatc ttgtgcaatg taacatcaga      1200
gattttgaga cacaacgtgg ctttcccccc ccccccggca      1240
tgcctgcagg tcgacaatat tggctattgg ccattgcata      1280
cgttgtatct atatcataat atgtacattt atattggctc      1320
atgtccaata tgaccgccat gttgacattg attattgact      1360
agttattaat agtaatcaat tacggggtca ttagttcata      1400
gcccatatat ggagttccgc gttacataac ttacggtaaa      1440
tggcccgcct ggctgaccgc ccaacgaccc ccgcccattg      1480
acgtcaataa tgacgtatgt tcccatagta acgccaatag      1520
ggactttcca ttgacgtcaa tgggtggagt atttacggta      1560
aactgcccac ttggcagtac atcaagtgta tcatatgcca      1600
agtccgcccc ctattgacgt caatgacggt aaatggcccg      1640
cctggcatta tgcccagtac atgaccttac gggactttcc      1680
tacttggcag tacatctacg tattagtcat cgctattacc      1720
atggtgatgc ggttttggca gtacaccaat gggcgtggat      1760
agcggtttga ctcacgggga tttccaagtc tccacccat       1800
tgacgtcaat gggagtttgt tttggcacca aaatcaacgg      1840
gactttccaa aatgtcgtaa taaccccgcc ccgttgacgc      1880
aaatgggcgg taggcgtgta cggtgggagg tctatataag      1920
cagagctcgt ttagtgaacc gtcagatcgc ctggagacgc      1960
catccacgct gttttgacct ccatagaaga caccgggacc      2000
gatccagcct ccgcggccgg aacggtgca ttggaacgcg       2040
gattcccgt gccaagagtg acgtaagtac cgcctataga       2080
ctctataggc acacccctt ggctcttatg catgctatac       2120
tgtttttggc ttgggccta tacacccccg cttccttatg       2160
ctataggtga tggtatagct tagcctatag gtgtgggtta      2200
ttgaccatta ttgccactc cctattggt gacgatactt        2240
tccattacta atccataaca tggctctttg ccacaactat      2280
ctctattggc tatatgccaa tactctgtcc ttcagagact      2320
gacacggact ctgtattttt acaggatggg gtcccattta      2360
```

-continued

```
ttatttacaa attcacatat acaacaacgc cgtccccgt       2400
gcccgcagtt tttattaaac atagcgtggg atctccacgc      2440
gaatctcggg tacgtgttcc ggacatgggc tcttctccgg      2480
tagcggcgga gcttccacat ccgagccctg gtcccatgcc      2520
tccagcggct catggtcgct cggcagctcc ttgctcctaa      2560
cagtggaggc cagacttagg cacagcacaa tgcccaccac      2600
caccagtgtg ccgcacaagg ccgtggcggt agggtatgtg      2640
tctgaaaatg agctcggaga ttgggctcgc accgctgacg      2680
cagatggaag acttaaggca gcggcagaag aagatgcagg      2720
cagctgagtt gttgtattct gataagagtc agaggtaact      2760
cccgttgcgg tgctgttaac ggtggagggc agtgtagtct      2800
gagcagtact cgttgctgcc gcgcgcgcca ccagacataa      2840
tagctgacag actaacagac tgttcctttc catgggtctt      2880
ttctgcagtc agggtccaag cttgcggccg cggatctgca      2920
ggaattcggc acgagagtag tagactccgc acgaagaagc      2960
aaaaaattaa agaagtgagt ttaaaatgga agggtggtat      3000
ctggttgttc ttggagtctg ctatacgctg acactggcaa      3040
tgcccaagac catttatgag cttaaaatgg aatgcccgca      3080
cactgtgggt ctcggtcaag gttacatcat tggctcaaca      3120
gaactaggtt tgatctcaat tgaggctgca tctgatataa      3160
agctcgagag ctcttgcaat tttgatcttc atacaacatc      3200
tatgggccag aagagtttca cccaagttga atggagaaag      3240
aaaagtgaca caactgatac cacaaatgct gcgtccacta      3280
cctttgaagc acaaactaaa actgttaacc ttagagggac      3320
ttgtatactg gcacctgaac tctatgatac attgaagaaa      3360
gtaaaaaaga cagtcctgtg ctatgatcta acatgtaatc      3400
aaacacattg tcagccaact gtctatctga ttgcacctgt      3440
attgacatgc atgtcaataa gaagttgtat ggctagtgtg      3480
tttacaagca ggattcaggt gatttatgaa aagacacatt      3520
gtgtaacagg tcagctgatt gagggtcagt gtttcaaccc      3560
agcacacaca ttgacattat ctcagcctgc tcacacttat      3600
gatactgtca cccttcctat ctcttgtttt tcacaccaa       3640
agaagtcgga gcaactaaaa gttataaaaa catttgaagg      3680
aattctgacg aagacaggtt gcacggagaa tgcattgcag      3720
ggttattatg tgtgtttttt agggagtcat tcagaacctt      3760
taattgttcc gagtttggag gacatacggt ctgctgaagt      3800
tgttagtagg atgcttgtac acccctaggg agaagaccat      3840
gatgccatac agaattcaca aagtcactta agaatagtgg      3880
gacctatcac agcaaaagtg ccatcaacta gttccacaga      3920
taccctaaag gggacagcct ttgcaggcgt cccaatgtat      3960
```

-continued

```
agctctttat ctacactagt cagaaatgca gacccagaat     4000
ttgtattttc tccaggtata gtacctgaat ctaatcacag     4040
tacatgtgat aagaagacag tacctatcac atggacaggc     4080
tacctaccaa tatcaggtga gatggaaaaa gtgactggat     4120
gtacagtttt ttgtacacta gcaggacctg gtgctagttg     4160
tgaggcctat tctgaaaatg gtatatttaa catcagttct     4200
ccaacatgtc ttgtaaacaa agtccaagaa tttcgtggat     4240
ctgaacagaa aataaatttt atctgtcagc gggtagatca     4280
ggatgttgtt gtatactgca atgggcaaaa gaaagtcata     4320
ttaaccaaaa ctttggttat tgggcagtgt atttatacat     4360
tcacaagcct attttcattg atgcctgatg tagcccactc     4400
attggctgta gaattatgtg tcccgggatt acatgggtgg     4440
gccactgtca tgcttctatc aacattctgc tttgggtggg     4480
tcttgattcc tgcggtcaca ttaataatat aaagtgtct      4520
aagggttttg acgttttctt gttcccatta cactaatgag     4560
tcaaaattta aattcatcct ggaaaaagtt aaaattgaat     4600
accaaaagac tatgggatca atggtgtgcg atgtatgtca     4640
tcatgagtgt gaaacagcaa agaacttga atcacataga      4680
cagagttgta tcaatggaca atgtcctat tgcatgacaa      4720
taactgaagc aactgaaagt gccttgcaag cccattattc     4760
catttgtaaa ttggcaggaa gatttcagga ggcactgaaa     4800
aagtcactta aaaagccaga ggtaaaaaaa ggttgttaca     4840
gaacactcgg ggtatttaga tataaagta gatgttatgt      4880
gggtttggta tggtgcctat tgttgacatg tgaaattgtt     4920
atttgggccg caagtgcaga gactccacta atggagtcag     4960
gctggtcaga tacggctcat ggtgttggtg agattccaat     5000
gaagacagac ctcgagctgg acttttcact gccttcttca     5040
tcctcttaca gttataggag aaagctcaca aacccagcca     5080
ataaagaaga gtctattccc ttccacttcc agatggaaaa     5120
acaagtaatt catgctgaaa tccaaccct gggtcattgg      5160
atggatgcga catttaatat taagactgca tttcattgtt     5200
atggtgcatg ccagaaatac tcttatccat ggcagacatc     5240
taagtgcttc tttgaaaagg actaccagta tgaaacaggc     5280
tggggctgta atcctggtga ctgcccaggg gttgggactg     5320
gatgcactgc ttgtggtgtt tatctcgata aactaaaatc     5360
tgttgggaag gcctataaga taattttcttt aaaatatacc    5400
agaaaggttt gtattcagtt aggaacagaa caaacttgca     5440
agcatattga tgcaaatgat tgtttagtga caccatctgt     5480
gaaagtttgc atagtgggca cagtttcaaa acttcaacca     5520
tctgatactc ttttgttctt aggtccacta gaacaagggg     5560
gaatcattct taagcaatgg tgcacaacat catgtgcatt     5600
tggggaccct ggtgatatca tgtccactcc cagtggtatg     5640
aggtgtccag agcacactgg atcatttagg aaaatttgcg     5680
gttttgctac tacaccagtt tgtgaatatc aaggaaatac     5720
catttctgga tataaagaa tgatggcaac aaaagattca      5760
ttccaatcat ttaacttaac agaacctcac atcacaacaa     5800
acaagcttga atggatcgac ccagatggga atacaagaga     5840
ccacgtaaac cttgtcttaa atagagatgt ctcatttcag     5880
gatttaagtg ataacccctg taaagtagac ctacacacac     5920
aagcaataga aggggcatgg ggttctggtg tagggtttac     5960
actcacatgt actgtcggat taacagagtg cccaagtttt     6000
atgacatcaa ttaaggcatg tgacctagct atgtgttatg     6040
gatcaacagt aacaaaccct tgccaggggc ctaatacagt     6080
gaaagtagtt ggtaaaggag gccattcagg gtcctcattt     6120
aaatgctgtc atgatacaga ttgctcctct gaaggtttac     6160
ttgcatcagc ccctcatctt gagagggtaa caggattcaa     6200
tcaaattgat tcagataagg tttatgatga tggtgcacca     6240
ccttgcacat tcaaatgctg gttcactaag tcaggtgagt     6280
ggcttcttgg gatcttaaac gggaattgga ttgttgttgt     6320
agtgcttgtt gtgatactca ttctctctat cataatgttc     6360
agtgttttgt gtcccaggag agggcacaag aaaactgtct     6400
aagcattgac ctcaactcct acattagatc atatacattt     6440
atgcacttcc tcatatttag ctgcactaag atattaataa     6480
actctagtta ttgactttat aagattatta tggaactaac     6520
ctcacttaaa aaaacaaat actttactca tatataactc      6560
catattctct taccgaggat tttgttcctg cggagcatac     6600
tactaggatc tacgtatgat cagcctcgac tgtgccttct     6640
agttgccagc catctgttgt ttgcccctcc cccgtgcctt     6680
ccttgaccct ggaaggtgcc actcccactg tccttttccta    6720
ataaaatgag gaaattgcat cgcattgtct gagtaggtgt     6760
cattctattc tgggggtgg ggtggggcag acagcaagg       6800
gggaggattg ggaagacaat agcaggcatg ctgggggatgc    6840
ggtgggctct atggcttctg aggcggaaag aaccagctgg     6880
ggctcgacag ctcgactcta gaattgcttc ctcgctcact     6920
gactcgctgc gctcggtcgt tcggctgcgg cgagcggtat     6960
cagctcactc aaaggcggta atacggttat ccacagaatc     7000
aggggataac gcaggaaaga acatgtgagc aaaaggccag     7040
caaaaggcca ggaaccgtaa aaggccgcg ttgctggcgt      7080
ttttccatag gctccgcccc cctgacgagc atcacaaaaa     7120
tcgacgctca agtcagaggt ggcgaaaccc gacaggacta     7160
taaagatacc aggcgtttcc ccctggaagc tccctcgtgc     7200
```

```
gctctcctgt tccgaccctg ccgcttaccg gatacctgtc      7240
cgcctttctc ccttcgggaa gcgtggcgct ttctcatagc      7280
tcacgctgta ggtatctcag ttcggtgtag gtcgttcgct      7320
ccaagctggg ctgtgtgcac gaacccccg ttcagcccga       7360
ccgctgcgcc ttatccggta actatcgtct tgagtccaac      7400
ccggtaagac acgacttatc gccactggca gcagccactg      7440
gtaacaggat tagcagagcg aggtatgtag gcggtgctac      7480
agagttcttg aagtggtggc ctaactacgg ctacactaga      7520
agaacagtat ttggtatctg cgctctgctg aagccagtta      7560
ccttcgaaaa aagagttggt agctcttgat ccggcaaaca      7600
aaccaccgct ggtagcggtg gtttttttgt ttgcaagcag      7640
cagattacgc gcagaaaaaa aggatctcaa gaagatcctt      7680
tgatcttttc tacggggtct gacgctcagt ggaacgaaaa      7720
ctcacgttaa gggattttgg tcatgagatt atcaaaaagg      7760
atcttcacct agatcctttt aaattaaaaa tgaagtttta      7800
aatcaatcta aagtatatat gagtaaactt ggtctgacag      7840
```
ttaccaatgc ttaatcagtg aggcacctat ctcagcgatc      7880
tgtctatttc gttcatccat agttgcctga ctc             7913

For a HPS+HFRS, or pan-hantavirus, vaccine composition or immunogenic composition, the composition will have at least one of the above-described SNV sequences (SEQ ID NO:1, SEQ ID NO:2 or SEQ ID NO:3), plus at least one other M-gene (e.g., whole full-length or ORF or ORF plus flanking sequences) from an HFRS virus. Examples of HFRS viruses include Seoul virus, Hantaan virus, Pumuula virus, and Dobrava virus. In addition, the vaccine composition or immunogenic composition may further include one or more of the above-described other HPS M-genes (e.g., whole full-length or ORF or ORF plus flanking sequences). A preferred HPS+HFRS vaccine or immunogenic composition comprises at least one of the above-described SNV sequences, and one or more of Puumala M-gene plasmid (preferably plasmid pWRG/PUU-M(s2) shown below as SEQ ID NO:11 or the ORF shown below as SEQ ID NO:14), Hantaan M-gene plasmid (preferably plasmid pWRG/HTN-M(x) shown below as SEQ ID NO:12), and Seoul (preferably plasmid pWRG-SEO-M which is Seoul hantavirus M segment, strain SR-11, subcloned into DNA vector pWRG7077, and shown below as SEQ ID NO:13).

pWRG/PUU-M(s2) DNA vaccine plasmid (SEQ ID NO:11) (the underlined section indicates the ORF)—

```
GGGGGGGGGGGGCGCTGAGGTCTGCCTCGTGAAGAAGGTGTTGCTGACTCATACCAGG
CCTGAATCGCCCCATCATCCAGCCAGAAAGTGAGGGAGCCACGGTTGATGAGAGCTTT
GTTGTAGGTGGACCAGTTGGTGATTTTGAACTTTTGCTTTGCCACGGAACGGTCTGCG
TTGTCGGGAAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACCAATTAACC
AATTCTGATTAGAAAAACTCATCGAGCATCAAATGAAACTGCAATTTATTCATATCAG
GATTATCAATACCATATTTTTGAAAAAGCCGTTTCTGTAATGAAGGAGAAAACTCACC
GAGGCAGTTCCATAGGATGGCAAGATCCTGGTATCGGTCTGCGATTCCGACTCGTCCA
ACATCAATACAACCTATTAATTTCCCCTCGTCAAAAATAAGGTTATCAAGTGAGAAAT
CACCATGAGTGACGACTGAATCCGGTGAGAATGGCAAAAGCTTATGCATTTCTTTCCA
GACTTGTTCAACAGGCCAGCCATTACGCTCGTCATCAAAATCACTCGCATCAACCAAA
CCGTTATTCATTCGTGATTGCGCCTGAGCGAGACGAAATACGCGATCGCTGTTAAAAG
GACAATTACAAACAGGAATCGAATGCAACCGGCGCAGGAACACTGCCAGCGCATCAAC
AATATTTTCACCTGAATCAGGATATTCTTCTAATACCTGGAATGCTGTTTTCCCGGGG
ATCGCAGTGGTGAGTAACCATGCATCATCAGGAGTACGGATAAAATGCTTGATGGTCG
GAAGAGGCATAAATTCCGTCAGCCAGTTTAGTCTGACCATCTCATCTGTAACATCATT
GGCAACGCTACCTTTGCCATGTTTCAGAAACAACTCTGGCGCATCGGGCTTCCCATAC
AATCGATAGATTGTCGCACCTGATTGCCCGACATTATCGCGAGCCCATTTATAC
CCATATAAATCAGCATCCATGTTGGAATTTAATCGCGGCCTCGAGCAAGACGTTTCCC
GTTGAATATGGCTCATAACACCCCTTGTATTACTGTTTATGTAAGCAGACAGTTTTAT
TGTTCATGATGATATATTTTTATCTTGTGCAATGTAACATCAGAGATTTTGAGACACA
ACGTGGCTTTCCCCCCCCCCCGGCATGCCTGCAGGTCGACAATATTGGCTATTGGCC
ATTGCATACGTTGTATCTATATCATAATATGTACATTTATATTGGCTCATGTCCAATA
```

-continued

```
TGACCGCCATGTTGACATTGATTATTGACTAGTTATTAATAGTAATCAATTACGGGGT

CATTAGTTCATAGCCCATATATGGAGTTCCGCGTTACATAACTTACGGTAAATGGCCC

GCCTGGCTGACCGCCCAACGACCCCCGCCCATTGACGTCAATAATGACGTATGTTCCC

ATAGTAACGCCAATAGGGACTTTCCATTGACGTCAATGGGTGGAGTATTTACGGTAAA

CTGCCCACTTGGCAGTACATCAAGTGTATCATATGCCAAGTCCGCCCCCTATTGACGT

CAATGACGGTAAATGGCCCGCCTGGCATTATGCCCAGTACATGACCTTACGGGACTTT

CCTACTTGGCAGTACATCTACGTATTAGTCATCGCTATTACCATGGTGATGCGGTTTT

GGCAGTACACCAATGGGCGTGGATAGCGGTTTGACTCACGGGGATTTCCAAGTCTCCA

CCCCATTGACGTCAATGGGAGTTTGTTTTGGCACCAAAATCAACGGGACTTTCCAAAA

TGTCGTAATAACCCCGCCCCGTTGACGCAAATGGGCGGTAGGCGTGTACGGTGGGAGG

TCTATATAAGCAGAGCTCGTTTAGTGAACCGTCAGATCGCCTGGAGACGCCATCCACG

CTGTTTTGACCTCCATAGAAGACACCGGGACCGATCCAGCCTCCGCGGCCGGGAACGG

TGCATTGGAACGCGGATTCCCCGTGCCAAGAGTGACGTAAGTACCGCCTATAGA

CTCTATAGGCACACCCCTTTGGCTCTTATGCATGCTATACTGTTTTTGGCTTGGGGCC

TATACACCCCCGCTTCCTTATGCTATAGGTGATGGTATAGCTTAGCCTATAGGTGTGG

GTTATTGACCATTATTGACCACTCCCCTATTGGTGACGATACTTTCCATTACTAATCC

ATAACATGGCTCTTTGCCACAACTATCTCTATTGGCTATATGCCAATACTCTGTCCTT

CAGAGACTGACACGGACTCTGTATTTTTACAGGATGGGGTCCCATTTATTATTTACAA

ATTCACATATACAACAACGCCGTCCCCCGTGCCCGCAGTTTTTATTAAACATAGCGTG

GGATCTCCACGCGAATCTCGGGTACGTGTTCCGGACATGGGCTCTTCTCCGGTAGCGG

CGGAGCTTCCACATCCGAGCCCTGGTCCCATGCCTCCAGCGGCTCATGGTCGCTCGGC

AGCTCCTTGCTCCTAACAGTGGAGGCCAGACTTAGGCACAGCACAATGCCCACCACCA

CCAGTGTGCCGCACAAGGCCGTGGCGGTAGGGTATGTGTCTGAAAATGAGCTCGGAGA

TTGGGCTCGCACCGCTGACGCAGATGGAAGACTTAAGGCAGCGGCAGAAGAAGATGCA

GGCAGCTGAGTTGTTGTATTCTGATAAGAGTCAGAGGTAACTCCCGTTGCGGTGCTGT

TAACGGTGGAGGGCAGTGTAGTCTGAGCAGTACTCGTTGCTGCCGCGCGCCACCAG

ACATAATAGCTGACAGACTAACAGACTGTTCCTTTCCATGGGTCTTTTCTGCAGTCAC

CGTCCAAGCTTGCGGCCGCGGATCTGCAGGAATTCGGCACGAGAGTAGTAGACTCCGC

AAGAAACAGCAAACACAGATAAATATGGGCGAGCTGTCCCCTGTGTGCCTGTACCTGC

TGCTGCAGGGCCTGCTGCTGTGTAACACCGGAGCCGCCAGGAACCTGAACGAGCTGAA

GATGGAGTGCCCCCACACCATCAGACTGGGCCAGGGCCTGGTGGTGGGCAGCGT

GGAGCTGCCCAGCCTGCCCATCCAGCAGGTGGAGACCCTGAAGCTGGAGAGCAGCTGT

AACTTCGACCTGCACACCAGCACAGCCGGCCAGCAGAGCTTCACCAAGTGGACCTGGG

AGATCAAGGGCGACCTGGCCGAGAACACCCAGGCCAGCAGCACCAGCTTCAGACCAA

GAGCAGCGAGGTGAACCTGAGAGGCCTGTGCCTGATCCCCACACTGGTGGTGGAGACC

GCCGCCAGAATGAGAAAGACCATCGCCTGCTACGACCTGAGCTGTAACCAGACCGTGT

GTCAGCCTACCGTGTACCTGATGGGCCCTATCCAGACCTGTATCACCACCAAGAGCTG

CCTGCTGTCCCTGGGCGATCAGAGAATCCAGGTGAACTACGAGAAAACCTACTGTGTG

AGCGGCCAGCTGGTGGAGGGCATCTGCTTCAACCCCATCCACACCATGGCCCTGAGCC

AGCCTAGCCACACCTACGACATCATGACCATGATGGTGAGATGCTTTCTGGTGATCAA

GAAGGTGACCAGCGGCGACAGCATGAAGATCGAGAAGAACTTCGAGACCCTGGTGCAG
```

-continued

AAGAATGGCTGTACCGCCAACAACTTCCAGGGCTACTACATCTGCCTGATCGGCAGCA

GCAGCGAGCCCCTGTACGTGCCCGCCCTGGACGACTACAGAAGCGCCGAGGTGCTGTC

CAGAATGGCCTTCGCCCCCACGGCGAGGACCACGACATCGAGAAAAACGCCGTGTCC

GCCATGAGAATCGCCGGCAAGGTGACCGGCAAGGCCCCCAGCACCGAGTCCAGCGACA

CCGTGCAGGGCATCGCCTTCAGCGGCAGCCCCCTGTACACCTCCACCGGCGTGCTGAC

CAGCAAGGACGACCCCGTGTACATCTGGGCCCCTGGCATCATCATGGAGGGCAACCAC

AGCATCTGTGAGAAGAAAACCCTGCCCCTGACCTGGACCGGCTTCATCAGCCTGCCCG

GCGAGATCGAGAAAACCACCCAGTGTACCGTGTTCTGTACCCTGGCCGGACCTG

GCGCCGACTGTGAGGCCTACAGCGAGACCGGCATCTTCAACATCAGCAGCCCCACCTG

CCTGATCAACCGGGTGCAGAGGTTCAGAGGCAGCGAGCAGCAGATCAAGTTTGTGTGC

CAGCGGGTGGACATGGACATCACCGTGTACTGTAACGGCATGAAGAAGGTGATCCTGA

CCAAGACACTGGTGATCGGCCAGTGTATCTACACCTTCACCAGCATCTTCTCCCTGAT

CCCCGGCGTGGCCCACAGCCTGGCCGTGGAGCTGTGTGCCCGGCCTGCACGGCTGG

GCCACCATGCTGCTGCTGCTGACCTTCTGCTTCGGCTGGGTGCTGATCCCTACCATCA

CCATGATCCTGCTGAAGATCCTGATCGCCTTCGCCTACCTGTGCTCCAAGTACAACAC

CGACAGCAAGTTCAGAATCCTGATCGAGAAAGTGAAGCGGGAGTACCAGAAAACCATG

GGCAGCATGGTGTGTGAAGTGTGCCAGTACGAGTGTGAGACCGCCAAGGAGCTGGAGT

CCCACAGAAAGAGCTGCTCCATCGGCAGCTGCCCCTACTGCCTGAACCCCAGCGAGGC

CACCACCTCCGCCCTGCAGGCCCACTTCAAAGTGTGTAAGCTGACCAGCCGGTTCCAG

GAGAACCTGAGGAAGTCCCTGACCGTGTACGAGCCCATGCAGGGCTGCTACAGAACCC

TGAGCCTGTTCCGGTACAGGAGCCGGTTCTTTGTGGGCCTGGTGTGGTGTGCTGCT

GGTGCTGGAGCTGATTGTGTGGGCCGCCAGCGCCGAGACCCAGAACCTGAATGCCGGC

TGGACCGACACCGCCCACGGCAGCGGCATCATCCCCATGAAAACCGACCTGGAGCTGG

ACTTCAGCCTGCCTAGCAGCGCCTCCTACACCTACAGGCGGCAGCTGCAGAATCCTGC

CAACGAGCAGGAGAAGATCCCCTTCCACCTGCAGCTGTCCAAGCAGGTGATCCACGCC

GAGATTCAGCACCTGGGCCACTGGATGGACGCCACCTTCAACCTGAAAACCGCC

TTCCACTGCTACGGCAGCTGTGAGAAGTACGCCTACCCTTGGCAGACCGCCGGCTGCT

TCATCGAGAAGGACTACGAGTACGAGACCGGCTGGGGCTGTAATCCTCCTGATTGCCC

CGGAGTGGGCACCGGCTGTACTGCATGTGGCGTGTACCTGGACAAGCTGAAGTCTGTG

GGCAAGGTGTTCAAGATCGTGTCCCTGAGGTACACCCGGAAAGTGTGTATCCAGCTGG

GCACCGAGCAGACCGTAAGACCGTGGACAGCAACGATTGCCTGATCACAACCAGCGT

GAAAGTGTGTCTGATCGGCACCATCAGCAAGTTCCAGCCCAGCGATACCCTGCTGTTT

CTGGGCCCCCTGCAGCAGGGCGGCCTGATCTTCAAGCAGTGGTGTACCACCACCTGCC

AGTTCGGCGATCCCGGCGATATCATGAGCACCCCCACCGGCATGAAGTGCCCTGAGCT

GAACGGCAGCTTCCGGAAGAAGTGTGCCTTCGCCACCACCCCTGTGTGTCAGTTCGAC

GGCAACACCATCAGCGGCTACAAGCGGATGATCGCCACCAAGGACAGCTTCCAGTCCT

TCAACGTGACCGAGCCCCACATCAGCACCAGCGCCCTGGAGTGGATCGATCCCGACAG

CAGCCTGAGGGACCACATCAACGTGATCGTGTCCAGGGACCTGAGCTTCCAGGACCTG

AGCGAGACCCCTGCCAGATCGACCTGGCCACCGCCAGCATCGATGGCGCCTGGGGCA

GCGGAGTGGGCTTCAACCTGGTGTGTACAGTGAGCCTGACCGAGTGTAGCGCCTTCCT

-continued

GACCAGCATCAAAGCCTGTGACGCCGCCATGTGTTACGGCAGCACCACCGCCAACCTG

GTGAGAGGCCAGAACACCATCCACATTGTGGGCAAAGGCGGCCACAGCGGCAGCAAGT

TTATGTGCTGCCACGACACCAAGTGTAGCAGCACCGGCCTGGTGGCCGCTGCCCCCCA

CCTGGACAGAGTGACCGGCTACAACCAGGCCGACAGCGACAAGATTTTCGACGA

CGGAGCCCCTGAGTGTGGCATGAGTTGCTGGTTCAAGAAGAGCGGCGAGTGGATTCTG

GGCGTGCTGAACGGGAATTGGATGGTGGTGGCCGTGCTGGTCGTGCTGCTGATCCTGA

GCATCCTGCTGTTCACCCTGTGCTGCCCTAGGAGACCCAGCTACCGGAAGGAGCACAA

GCCCTGAGTTTTGCTTACTAACATAATTATTGTATTCTGTTTATTGACACAATTACCA

TATGATTAACTGTATTCCCCCATCTTATATCTTATATAATATTCTTTATTTAATCACT

ATATAGAAAAAAAACTAGCACTTTACTAATTAAATTACCCCATACCGATTATGCCTGG

ACTTTTGTTCCTGCGGAGCATACTACTAGGATCTACGTATGATCAGCCTCGACTGTGC

CTTCTAGTTGCCAGCCATCTGTTGTTTGCCCCTCCCCCGTGCCTTCCTTGACCCTGGA

AGGTGCCACTCCCACTGTCCTTTCCTAATAAAATGAGGAAATTGCATCGCATTGTCTG

AGTAGGTGTCATTCTATTCTGGGGGGTGGGGTGGGGCAGGACAGCAAGGGGGAGGATT

GGGAAGACAATAGCAGGCATGCTGGGGATGCGGTGGGCTCTATGGCTTCTGAGGCGGA

AAGAACCAGCTGGGGCTCGACAGCTCGACTCTAGAATTGCTTCCTCGCTCACTGACTC

GCTGCGCTCGGTCGTTCGGCTGCGGCGAGCGGTATCAGCTCACTCAAAGGCGGTAATA

CGGTTATCCACAGAATCAGGGGATAACGCAGGAAAGAACATGTGAGCAAAAGGCCAGC

AAAAGGCCAGGAACCGTAAAAAGGCCGCGTTGCTGGCGTTTTTCCATAGGCTCCGCCC

CCCTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCGA

CCCTGCCGCTTACCGGATACCTGTCCGCCTTTCTCCCTTCGGGAAGCGTGGCGC

TTTCTCATAGCTCACGCTGTAGGTATCTCAGTTCGGTGTAGGTCGTTCGCTCCAAGCT

GGGCTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGGCC

TAACTACGGCTACACTAGAAGAACAGTATTTGGTATCTGCGCTCTGCTGAAGCCAGTT

ACCTTCGGAAAAAGAGTTGGTAGCTCTTGATCCGGCAAACAAACCACCGCTGGTAGCG

GTGGTTTTTTGTTTGCAAGCAGCAGATTACGCGCAGAAAAAAAGGATCTCAAGAAGA

TCCTTTGATCTTTTCTACGGGGTCTGACGCTCAGTGGAACGAAAACTCACGTTAAGGG

ATTTTGGTCATGAGATTATCAAAAAGGATCTTCACCTAGATCCTTTTAAATTAAAAAT

GAAGTTTTAAATCAATCTAAAGTATATATGAGTAAACTTGGTCTGACAGTTACCAATG

CTTAATCAGTGAGGCACCTATCTCAGCGATCTGTCTATTTCGTTCATCCATAGTTGCC

TGACTC

Puumala synthetic full-length M-segment ORF—SEQ ID NO:14

ATGGGCGAGCTGTCCCCTGTGTGCCTGTACCTGCTGCTGCAGGGCCTGCTGCTGTGTA

ACACCGGAGCCGCCAGGAACCTGAACGAGCTGAAGATGGAGTGCCCCCACACCATCAG

ACTGGGCCAGGGCCTGGTGGTGGGCAGCGTGGAGCTGCCCAGCCTGCCCATCCAGCAG

GTGGAGACCCTGAAGCTGGAGAGCAGCTGTAACTTCGACCTGCACACCAGCACAGCCG

-continued

```
GCCAGCAGAGCTTCACCAAGTGGACCTGGGAGATCAAGGGCGACCTGGCCGAGAACAC
CCAGGCCAGCAGCACCAGCTTCCAGACCAAGAGCAGCGAGGTGAACCTGAGAGGCCTG
TGCCTGATCCCCACACTGGTGGTGGAGACCGCCGCCAGAATGAGAAAGACCATCGCCT
GCTACGACCTGAGCTGTAACCAGACCGTGTGTCAGCCTACCGTGTACCTGATGGGCCC
TATCCAGACCTGTATCACCACCAAGAGCTGCCTGCTGTCCCTGGGCGATCAGAGAATC
CAGGTGAACTACGAGAAAACCTACTGTGTGAGCGGCCAGCTGGTGGAGGGCATCTGCT
TCAACCCCATCCACACCATGGCCCTGAGCCAGCCTAGCCACACCTACGACATCATGAC
CATGATGGTGAGATGCTTTCTGGTGATCAAGAAGGTGACCAGCGGCGACAGCATGAAG
ATCGAGAAGAACTTCGAGACCCTGGTGCAGAAGAATGGCTGTACCGCCAACAACTTCC
AGGGCTACTACATCTGCCTGATCGGCAGCAGCAGCGAGCCCCTGTACGTGCCCGCCCT
GGACGACTACAGAAGCGCCGAGGTGCTGTCCAGAATGGCCTTCGCCCCCCACGGCGAG
GACCACGACATCGAGAAAAACGCCGTGTCCGCCATGAGAATCGCCGGCAAGGTGACCG
GCAAGGCCCCCAGCACCGAGTCCAGCGACACCGTGCAGGGCATCGCCTTCAGCGGCAG
CCCCCTGTACACCTCCACCGGCGTGCTGACCAGCAAGGACGACCCCGTGTACATCTGG
GCCCCTGGCATCATCATGGAGGGCAACCACAGCATCTGTGAGAAGAAACCCTGCCCC
TGACCTGGACCGGCTTCATCAGCCTGCCCGGCGAGATCGAGAAAACCACCCAGTGTAC
CGTGTTCTGTACCCTGGCCGGACCTGGCGCCGACTGTGAGGCCTACAGCGAGACCGGC
ATCTTCAACATCAGCAGCCCCACCTGCCTGATCAACCGGGTGCAGAGGTTCAGAGGCA
GCGAGCAGCAGATCAAGTTTGTGTGCCAGCGGGTGGACATGGACATCACCGTGTACTG
TAACGGCATGAAGAAGGTGATCCTGACCAAGACACTGGTGATCGGCCAGTGTATCTAC
ACCTTCACCAGCATCTTCTCCCTGATCCCCGGCGTGGCCCACAGCCTGGCCGTGGAGC
TGTGTGTGCCCGGCCTGCACGGCTGGGCCACCATGCTGCTGCTGCTGACCTTCTGCTT
CGGCTGGGTGCTGATCCCTACCATCACCATGATCCTGCTGAAGATCCTGATCGCCTTC
GCCTACCTGTGCTCCAAGTACAACACCGACAGCAAGTTCAGAATCCTGATCGAGAAAG
TGAAGCGGGAGTACCAGAAAACCATGGGCAGCATGGTGTGTGAAGTGTGCCAGTACGA
GTGTGAGACCGCCAAGGAGCTGGAGTCCCACAGAAAGAGCTGCTCCATCGGCAGCTGC
CCCTACTGCCTGAACCCCAGCGAGGCCACCACCTCCGCCCTGCAGGCCCACTTCAAAG
TGTGTAAGCTGACCAGCCGGTTCCAGGAGAACCTGAGGAAGTCCCTGACCGTGTACGA
GCCCATGCAGGGCTGCTACAGAACCCTGAGCCTGTTCCGGTACAGGAGCCGGTTCTTT
GTGGGCCTGGTGTGGTGTGTGCTGCTGGTGCTGGAGCTGATTGTGTGGGCCGCCAGCG
CCGAGACCCAGAACCTGAATGCCGGCTGGACCGACACCGCCCACGGCAGCGGCATCAT
CCCCATGAAAACCGACCTGGAGCTGGACTTCAGCCTGCCTAGCAGCGCCTCCTACACC
TACAGGCGGCAGCTGCAGAATCCTGCCAACGAGCAGGAGAAGATCCCCTTCCACCTGC
AGCTGTCCAAGCAGGTGATCCACGCCGAGATTCAGCACCTGGGCCACTGGATGGACGC
CACCTTCAACCTGAAAACCGCCTTCCACTGCTACGGCAGCTGTGAGAAGTACGCCTAC
CCTTGGCAGACCGCCGGCTGCTTCATCGAGAAGGACTACGAGTACGAGACCGGCTGGG
GCTGTAATCCTCCTGATTGCCCCGGAGTGGGCACCGGCTGTACTGCATGTGGCGTGTA
CCTGGACAAGCTGAAGTCTGTGGGCAAGGTGTTCAAGATCGTGTCCCTGAGGTACACC
CGGAAAGTGTGTATCCAGCTGGGCACCGAGCAGACCTGTAAGACCGTGGACAGCAACG
ATTGCCTGATCACAACCAGCGTGAAAGTGTGTCTGATCGGCACCATCAGCAAGTTCCA
```

-continued

```
GCCCAGCGATACCCTGCTGTTTCTGGGCCCCCTGCAGCAGGGCGGCCTGATCTTCAAG
CAGTGGTGTACCACCACCTGCCAGTTCGGCGATCCCGGCGATATCATGAGCACCCCCA
CCGGCATGAAGTGCCCTGAGCTGAACGGCAGCTTCCGGAAGAAGTGTGCCTTCGCCAC
CACCCCTGTGTGTCAGTTCGACGGCAACACCATCAGCGGCTACAAGCGGATGATCGCC
ACCAAGGACAGCTTCCAGTCCTTCAACGTGACCGAGCCCCACATCAGCACCAGCGCCC
TGGAGTGGATCGATCCCGACAGCAGCTGAGGGACCACATCAACGTGATCGTGTCCAG
GGACCTGAGCTTCCAGGACCTGAGCGAGACCCCCTGCCAGATCGACCTGGCCACCGCC
AGCATCGATGGCGCCTGGGGCAGCGGAGTGGGCTTCAACCTGGTGTGTACAGTGAGCC
TGACCGAGTGTAGCGCCTTCCTGACCAGCATCAAAGCCTGTGACGCCGCCATGTGTTA
CGGCAGCACCACCGCCAACCTGGTGAGAGGCCAGAACACCATCCACATTGTGGGCAAA
GGCGGCCACAGCGGCAGCAAGTTTATGTGCTGCCACGACACCAAGTGTAGCAGCACCG
GCCTGGTGGCCGCTGCCCCCCACCTGGACAGAGTGACCGGCTACAACCAGGCCGACAG
CGACAAGATTTTCGACGACGGAGCCCCTGAGTGTGGCATGAGTTGCTGGTTCAAGAAG
AGCGGCGAGTGGATTCTGGGCGTGCTGAACGGGAATTGGATGGTGGTGGCCGTGCTGG
TCGTGCTGCTGATCCTGAGCATCCTGCTGTTCACCCTGTGCTGCCCTAGGAGACCCAG
CTACCGGAAGGAGCACAAGCCCTGA
```

Plasmid pWRG/HTN-M(x)—SEQ ID NO:12

```
ggggggggggg ggcgctgagg tctgcctcgt gaagaaggtg     40
ttgctgactc ataccaggcc tgaatcgccc atcatccag       80
ccagaaagtg agggagccac ggttgatgag agctttgttg      120
taggtggacc agttggtgat tttgaacttt tgctttgcca      160
cggaacggtc tgcgttgtcg ggaagatgcg tgatctgatc      200
cttcaactca gcaaagttc gatttattca acaaagccgc       240
cgtcccgtca gtcagcgta atgctctgcc agtgttacaa       280
ccaattaacc aattctgatt agaaaaactc atcgagcatc      320
aaatgaaact gcaatttatt catatcagga ttatcaatac      360
catattttg aaaaagccgt ttctgtaatg aaggagaaaa       400
ctcaccgagg cagttccata ggatggcaag atcctggtat      440
cggtctgcga ttccgactcg tccaacatca atacaaccta     480
ttaatttccc ctcgtcaaaa ataaggttat caagtgagaa      520
atcaccatga gtgacgactg aatccggtga gaatggcaaa      560
agcttatgca tttctttcca gacttgttca acaggccagc      600
cattacgctc gtcatcaaaa tcactcgcat caaccaaacc      640
gttattcatt cgtgattgcg cctgagcgag acgaaatacg      680
cgatcgctgt taaaaggaca attacaaaca ggaatcgaat      720
gcaaccggcg caggaacact gccagcgcat caacaatatt      760
ttcacctgaa tcaggatatt cttctaatac ctggaatgct      800
gttttcccgg ggatcgcagt ggtgagtaac catgcatcat      840
caggagtacg gataaaatgc ttgatggtcg gaagaggcat      880
```

```
aaattccgtc agccagttta gtctgaccat ctcatctgta      920
acatcattgg caacgctacc tttgccatgt ttcagaaaca      960
actctggcgc atcgggcttc ccatacaatc gatagattgt     1000
cgcacctgat tgcccgacat tatcgcgagc ccatttatac     1040
ccatataaat cagcatccat gttggaattt aatcgcggcc     1080
tcgagcaaga cgtttcccgt tgaatatggc tcataacacc     1120
ccttgtatta ctgtttatgt aagcagacag ttttattgtt     1160
catgatgata tatttttatc ttgtgcaatg taacatcaga     1200
gattttgaga cacaacgtgg ctttcccccc ccccccggca     1240
tgcctgcagg tcgacaatat tggctattgg ccattgcata     1280
cgttgtatct atatcataat atgtacattt atattggctc     1320
atgtccaata tgaccgccat gttgacattg attattgact     1360
agttattaat agtaatcaat tacgggtca ttagttcata      1400
gcccatatat ggagttccgc gttacataac ttacggtaaa     1440
tggcccgcct ggctgaccgc ccaacgaccc ccgcccattg     1480
acgtcaataa tgacgtatgt tcccatagta acgccaatag     1520
ggactttcca ttgacgtcaa tgggtggagt atttacgta      1560
aactgcccac ttggcagtac atcaagtgta tcatatgcca     1600
agtccgcccc ctattgacgt caatgacggt aaatggcccg     1640
cctggcatta tgcccagtac atgaccttac gggactttcc     1680
tacttggcag tacatctacg tattagtcat cgctattacc     1720
atggtgatgc ggttttggca gtacaccaat gggcgtggat     1760
agcggtttga ctcacgggga tttccaagtc tccaccccat     1800
```

-continued

```
tgacgtcaat gggagtttgt tttggcacca aaatcaacgg        1840
gactttccaa aatgtcgtaa taaccccgcc ccgttgacgc        1880
aaatgggcgg taggcgtgta cggtgggagg tctatataag        1920
cagagctcgt ttagtgaacc gtcagatcgc ctggagacgc        1960
catccacgct gttttgacct gcatcgaaga caccgggacc        2000
gatccagcct ccgcggccgg gaacggtgca ttggaacgcg        2040
gattccccgt gccaagagtg acgtaagtac cgcctataga        2080
ctctataggc acaccccttt ggctcttatg catgctatac        2120
tgttttttggc ttggggccta tacaccccg cttccttatg        2160
ctataggtga tggtatagct tagcctatag gtgtgggtta        2200
ttgaccatta ttgaccactc ccctattggt gacgatactt        2240
tccattacta atccataaca tggctctttg ccacaactat        2280
ctctattggc tatatgccaa tactctgtcc ttcagagact        2320
gacacggact ctgtattttt acaggatggg gtcccattta        2360
ttatttacaa attcacatat acaacaacgc cgtcccccgt        2400
gcccgcagtt tttattaaac atagcgtggg atctccacgc        2440
gaatctcggg tacgtgttcc ggacatgggc tcttctccgg        2480
tagcggcgga gcttccacat ccgagccctg gtcccatgcc        2520
tccagcggct catggtcgct cggcagctcc ttgctcctaa        2560
cagtggaggc cagacttagg cacagcacaa tgcccaccac        2600
caccagtgtg ccgcacaagg ccgtggcggt agggtatgtg        2640
tctgaaaatg agctcggaga ttgggctcgc accgctgacg        2680
cagatggaag acttaaggca gcggcagaag aagatgcagg        2720
cagctgagtt gttgtattct gataagagtc agaggtaact        2760
cccgttgcgg tgctgttaac ggtggagggc agtgtagtct        2800
gagcagtact cgttgctgcc gcgcgcgcca ccagacataa        2840
tagctgacga actaacagac tgttcctttc catgggtctt        2880
ttctgcagtc accgtccaag cttgcggccg cggatctgca        2920
ggaattcggc acgagagtag tagactccgc aagaaacagc        2960
agtcaatcag caacatgggg atatggaagt ggctagtgat        3000
ggccagttta gtatggcctg ttttgacact gagaaatgtc        3040
tatgacatga aaattgagtg cccccataca gtaagttttg        3080
gggaaaacag tgtgataggt tatgtagaat taccccccgt        3120
gccattggcc gacacagcac agatggtgcc tgagagttct        3160
tgtagcatgg ataatcacca atcgttgaat acaataacaa        3200
aatatacccca agtaagttgg agaggaaagg ctgatcagtc        3240
acagtctagt caaaattcat ttgagacagt gtccactgaa        3280
gttgacttga aaggaacatg tgctctaaaa cacaaaatgg        3320
tggaagaatc ataccgtagt aggaaatcag taacctgtta        3360
cgacctgtct tgcaatagca cttactgcaa gccaacacta        3400
tacatgattg taccaattca tgcatgcaat atgatgaaaa        3440
gctgtttgat tgcattggga ccatacagag tacaggtggt        3480
ttatgagaga tcttattgca tgacaggagt cctgattgaa        3520
gggaaatgct ttgtcccaga tcaaagtgtg gtcagtatta        3560
tcaagcatgg gatctttgat attgcaagtt ttcatattgt        3600
atgtttcttt gttgcagtta aagggaatac ttataaaatt        3640
tttgaacagg ttaagaaatc ctttgaatca acatgcaatg        3680
atacagagaa taaagtgcaa ggatattata tttgtattgt        3720
aggggggaaac tctgcaccaa tatatgttcc aacacttgat        3760
gatttcagat ccatggaagc atttacagga atcttcagat        3800
caccacatgg ggaagatcat gatctggctg gagaagaaat        3840
tgcatcttat tctatagtcg gacctgccaa tgcaaaagtt        3880
cctcatagtg ctagctcaga tacattgagc ttgattgcct        3920
attcaggtat accatcttat tcttccctta gcatcctaac        3960
aagttcaaca gaagctaagc atgtattcag ccctgggttg        4000
ttcccaaaac ttaatcacac aaattgtgat aaaagtgcca        4040
taccactcat atggactggg atgattgatt tacctggata        4080
ctacgaagct gtccacccct gtacagtttt ttgcgtatta        4120
tcaggtcctg gggcatcatg tgaagccttt tctgaaggcg        4160
ggattttcaa cataacctct cccatgtgct tagtgtcaaa        4200
acaaaatcga ttccggttaa cagaacagca agtgaatttt        4240
gtgtgtcagc gagtggacat ggacattgtt gtgtactgca        4280
acgggcagag gaaagtaata ttaacaaaaa ctctagttat        4320
tggacagtgt atatatacta taacaagctt attctcatta        4360
ctacctggag tagcacattc tattgctgtt gaattgtgtg        4400
tacctgggtt ccatggttgg gccacagctg ctctgcttgt        4440
tacattctgt ttcggatggg ttcttatacc agcaattaca        4480
tttatcatac taacagtcct aaagttcatt gctaatattt        4520
ttcacacaag taatcaagag aataggctaa aatcagtact        4560
tagaaagata aaggaagagt ttgaaaaaac aaaaggctca        4600
atggtatgtg atgtctgcaa gtatgagtgt gaaacctata        4640
aagaattaaa ggcacacggg gtatcatgcc cccaatctca        4680
atgtccttac tgttttactc attgtgaacc cacagaagca        4720
gcattccaag ctcattacaa ggtatgccaa gttactcaca        4760
gattcaggga tgatctaaag aaaactgtta ctcctcaaaa        4800
ttttacacca ggatgttacc ggacactaaa tttatttaga        4840
tacaaaagca ggtgctacat ctttacaatg tggatatttc        4880
ttcttgtctt agaatccata ctgtgggctg caagtgcatc        4920
agagacacca ttaactcctg tctggaatga caatgcccat        4960
ggggtaggtt ctgttcctat gcatacagat ttagagcttg        5000
atttctcttt aacatccagt tccaagtata cataccgtag        5040
```

-continued

| | |
|---|---|
| gaggttaaca aacccacttg aggaagcaca atccattgac | 5080 |
| ctacatattg aaatagaaga acagacaatt ggtgttgatg | 5120 |
| tgcatgctct aggacactgg tttgatggtc gtcttaacct | 5160 |
| taaaacatcc tttcactgtt atggtgcttg tacaaagtat | 5200 |
| gaatacccett ggcatactgc aaagtgccac tatgaaagag | 5240 |
| attaccaata tgagacgagc tggggttgta atccatcaga | 5280 |
| ttgtcctggg gtgggcacag gctgtacagc atgtggttta | 5320 |
| tacctagatc aactgaaacc agttggtagt gcttataaaa | 5360 |
| ttatcacaat aaggtacagc aggagagtct gtgttcagtt | 5400 |
| tggggaggaa aacctttgta agataataga catgaatgat | 5440 |
| tgttttgtat ctaggcatgt taaggtctgc ataattggta | 5480 |
| cagtatctaa attctctcag ggtgatacct tattgttttt | 5520 |
| tggaccgctt gaaggtggtg gtctaatatt taaacactgg | 5560 |
| tgtacatcca catgtcaatt tggtgaccca ggagatatca | 5600 |
| tgagtccaag agacaaaggt tttttatgcc ctgagtttcc | 5640 |
| aggtagtttc aggaagaaat gcaactttgc tactaccccct | 5680 |
| atttgtgagt atgatggaaa tatggtctca ggttacaaga | 5720 |
| aagtgatggc cacaattgat tccttccaat cttttaatac | 5760 |
| aagcactatg cacttcactg atgaaaggat agagtggaaa | 5800 |
| gaccctgatg gaatgctaag ggaccatata aacatttag | 5840 |
| taacgaagga cattgacttt gataaccttg gtgaaaatcc | 5880 |
| ttgcaaaatt ggcctacaaa catcttctat tgaggggggcc | 5920 |
| tggggttctg gtgtgggggtt cacattaaca tgtctggtat | 5960 |
| cactaacaga atgtcctacc ttttttgacct caataaaggc | 6000 |
| ttgtgataag gctatctgtt atggtgcaga gagtgtaaca | 6040 |
| ttgacaagag gacaaaatac agtcaaggta tcagggaaag | 6080 |
| gtggccatag tggttcaaca tttaggtgtt gccatgggga | 6120 |
| ggactgttca caaattggac tccatgctgc tgcacctcac | 6160 |
| cttgacaagg taaatgggat ttctgagata gaaaatagta | 6200 |
| aagtatatga tgatggggca ccgcaatgtg ggataaaatg | 6240 |
| ttggtttgtt aaatcagggg aatggatttc agggatattc | 6280 |
| agtggtaatt ggattgtact cattgtcctc tgtgtatttc | 6320 |
| tattgttctc cttggttttta ctaagcattc tctgtcccgt | 6360 |
| aaggaagcat aaaaaatcat agctaaattc tgtgactatc | 6400 |
| ctgttcttat gtatagcttt aacatatata ctaattttta | 6440 |
| tattccagta tactctatct aacacactaa aaaaaatagt | 6480 |
| agctttctaa ccacaaaacg gatctacgta tgatcagcct | 6520 |
| cgactgtgcc ttctagttgc cagccatctg ttgtttgccc | 6560 |
| ctcccccgtg ccttccttga ccctggaagg tgccactccc | 6600 |
| actgtccttc cctaataaaa tgaggaaatt gcatcgcatt | 6640 |
| gtctgagtag gtgtcattct attctggggg gtggggtggg | 6680 |

-continued

| | |
|---|---|
| gcaggacagc aaggggggagg attgggaaga caatagcagg | 6720 |
| catgctgggg atgcgtgggg ctctatggct tctgaggcgg | 6760 |
| aaagaaccag ctggggctcg acagctcgac tctagaattg | 6800 |
| cttcctcgct cactgactcg ctgcgctcgg tcgttcggct | 6840 |
| gcggcgagcg gtatcagctc actcaaaggc ggtaatacgg | 6880 |
| ttatccacag aatcagggga taacgcagga aagaacatgt | 6920 |
| gagcaaaagg ccagcaaaag gccaggaacc gtaaaaaggc | 6960 |
| cgcgttgctg gcgtttttcc ataggctccg ccccccctgac | 7000 |
| gagcatcaca aaaatcgacg ctcaagtcag aggtggcgaa | 7040 |
| acccgacagg actataaaga taccaggcgt ttccccctgg | 7080 |
| aagctccctc gtgcgctctc ctgttccgac cctgccgctt | 7120 |
| accggatacc tgtccgcctt tctcccttcg ggaagcgtgg | 7160 |
| cgctttctca tagctcacgc tgtaggtatc tcagttcggt | 7200 |
| gtaggtcgtt cgctccaagc tgggctgtgt gcacgaaccc | 7240 |
| cccgttcagc ccgaccgctg cgccttatcc ggtaactatc | 7280 |
| gtcttgagtc caacccggta agacacgact tatcgccact | 7320 |
| ggcagcagcc actggtaaca ggattagcag agcgaggtat | 7360 |
| gtaggcggtg ctacagagtt cttgaagtgg tggcctaact | 7400 |
| acggctacac tagaagaaca gtatttggta tctgcgctct | 7440 |
| gctgaagcca gttaccttcg gaaaaagagt tggtagctct | 7480 |
| tgatccggca aacaaaccac cgctggtagc ggtggttttt | 7520 |
| ttgtttgcaa gcagcagatt acgcgcagaa aaaaaggatc | 7560 |
| tcaagaagat cctttgatct tttctacggg gtctgacgct | 7600 |
| cagtggaacg aaaactcacg ttaagggatt ttggtcatga | 7640 |
| gattatcaaa aaggatcttc acctagatcc ttttaaatta | 7680 |
| aaaatgaagt tttaaatcaa tctaaagtat atatgagtaa | 7720 |
| acttggtctg acagttacca atgcttaatc agtgaggcac | 7760 |
| ctatctcagc gatctgtcta tttcgttcat ccatagttgc | 7800 | pWRG-SEO-M (Seoul hantavirus M segment, strain SR-11, subcloned into DNA vector pWRG7077)—SEQ ID NO:13

| | |
|---|---|
| ggggggggggg ggcgctgagg tctgcctcgt gaagaaggtg | 40 |
| ttgctgactc ataccaggcc tgaatcgccc catcatccag | 80 |
| ccagaaagtg agggagccac ggttgatgag agctttgttg | 120 |
| taggtggacc agttggtgat tttgaacttt tgctttgcca | 160 |
| cggaacggtc tgcgttgtcg ggaagatgcg tgatctgatc | 200 |
| cttcaactca gcaaaagttc gatttattca acaaagccga | 240 |
| cgtcccgtca gtcagcgta atgctctgcc agtgttacaa | 280 |
| ccaattaacc aattctgatt agaaaaactc atcgagcatc | 320 |
| aaatgaaact gcaatttatt catatcagga ttatcaatac | 360 |

-continued

| | |
|---|---|
| catattttg aaaagccgt ttctgtaatg aaggagaaaa | 400 |
| ctcaccgagg cagttccata ggatggcaag atcctggtat | 440 |
| cggtctgcga ttccgactcg tccaacatca atacaaccta | 480 |
| ttaatttccc ctcgtcaaaa ataaggttat caagtgagaa | 520 |
| atcaccatga gtgacgactg aatccggtga gaatggcaaa | 560 |
| agcttatgca tttctttcca gacttgttca acaggccagc | 600 |
| cattacgctc gtcatcaaaa tcactcgcat caaccaaacc | 640 |
| gttattcatt cgtgattgcg cctgagcgag acgaaatacg | 680 |
| cgatcgctgt taaaaggaca attacaaaca ggaatcgaat | 720 |
| gcaaccggcg caggaacact gccagcgcat caacaatatt | 760 |
| ttcacctgaa tcaggatatt cttctaatac ctggaatgct | 800 |
| gttttcccgg ggatcgcagt ggtgagtaac catgcatcat | 840 |
| caggagtacg gataaaatgc ttgatggtcg gaagaggcat | 880 |
| aaattccgtc agccagttta gtctgaccat ctcatctgta | 920 |
| acatcattgg caacgctacc tttgccatgt ttcagaaaca | 960 |
| actctggcgc atcgggcttc ccatacaatc gatagattgt | 1000 |
| cgcacctgat tgcccacat tatcgcgagc ccatttatac | 1040 |
| ccatataaat cagcatccat gttggaattt aatcgcggcc | 1080 |
| tcgagcaaga cgtttcccgt tgaatatggc tcataacacc | 1120 |
| ccttgtatta ctgtttatgt aagcagacag ttttattgtt | 1160 |
| catgatgata tatttttatc ttgtgcaatg taacatcaga | 1200 |
| gattttgaga cacaacgtgg ctttcccccc ccccccggca | 1240 |
| tgcctgcagg tcgacataaa tcaatattgg ctattggcca | 1280 |
| ttgcatacgt tgtatctata tcataatatg tacatttata | 1320 |
| ttggctcatg tccaatatga ccgccatgtt gacattgatt | 1360 |
| attgactagt tattaatagt aatcaattac ggggtcatta | 1400 |
| gttcatagcc catatatgga gttccgcgtt acataactta | 1440 |
| cggtaaatgg cccgcctcgt gaccgcccaa cgaccccgc | 1480 |
| ccattgacgt caataatgac gtatgttccc atagtaacgc | 1520 |
| caatagggac tttccattga cgtcaatggg tggagtattt | 1560 |
| acggtaaact gcccacttgg cagtacatca agtgtatcat | 1600 |
| atgccaagtc cggcccccta ttgacgtcaa tgacggtaaa | 1640 |
| tggcccgcct ggcattatgc ccagtacatg accttacggg | 1680 |
| actttcctac ttggcagtac atctacgtat tagtcatcgc | 1720 |
| tattaccatg gtgatgcggt tttggcagta caccaatggg | 1760 |
| cgtggatagc ggtttgactc acggggattt ccaagtctcc | 1800 |
| accccattga cgtcaatggg agtttgtttt ggcaccaaaa | 1840 |
| tcaacgggac tttccaaaat gtcgtaataa ccccgccccg | 1880 |
| ttgacgcaaa tgggcggtag gcgtgtacgg tgggaggtct | 1920 |
| atataagcag agctcgttta gtgaaccgtc agatcgcctg | 1960 |
| gagacgccat ccacgctgtt ttgacctcca tagaagacac | 2000 |
| cgggaccgat ccagcctccg cggccgggaa cggtgcattg | 2040 |
| gaacgcggat tccccgtgcc aagagtgacg taagtaccgc | 2080 |
| ctatagactc tataggcaca ccccttggc tcttatgcat | 2120 |
| gctatactgt ttttggcttg gggcctatac accccgctc | 2160 |
| cttatgctat aggtgatggt atagcttagc ctataggtgt | 2200 |
| gggttattga ccattattga ccactcccct attggtgacg | 2240 |
| atactttcca ttactaatcc ataacatggc tctttgccac | 2280 |
| aactatctct attggctata tgccaatact ctgtccttca | 2320 |
| gagactgaca cggactctgt atttttacag gatggggtcc | 2360 |
| catttattat ttacaaattc acatatacaa caacgccgtc | 2400 |
| ccccgtgccc gcagttttta ttaaacatag cgtgggatct | 2440 |
| ccacgcgaat ctcgggtacg tgttccggac atgggctctt | 2480 |
| ctccggtagc ggcggagctt ccacatccga gccctggtcc | 2520 |
| catgcctcca gcggctcatg gtcgctcggc agctccttgc | 2560 |
| tcctaacagt ggaggccaga cttaggcaca gcacaatgcc | 2600 |
| caccaccacc agtgtgccgc acaaggccgt ggcggtaggg | 2640 |
| tatgtgtctg aaaatgagct cggagattgg gctcgcaccg | 2680 |
| tgacgcagat ggaagactta aggcagcggc agaagaagat | 2720 |
| gcaggcagct gagttgttgt attctgataa gagtcagagg | 2760 |
| taactcccgt tgcggtgctg ttaacggtgg agggcagtgt | 2800 |
| agtctgagca gtactcgttg ctgccgcgcg cgccaccaga | 2840 |
| cataatagct gacagactaa cagactgttc cttccatgg | 2880 |
| gtctttctg cagtcaccgt ccaagcttgc ggccgcggat | 2920 |
| ctgcaggaat tcggcacgag agtagtagac tccgcaagaa | 2960 |
| acagcagtta aagaacaata ggatcatgtg gagtttgcta | 3000 |
| ttactggccg ctttagttgg ccaaggcttt gcattaaaaa | 3040 |
| atgtatttga catgagaatt cagttgcccc actcagtcaa | 3080 |
| ctttggggaa acaagtgtgt caggctatac agaatttccc | 3120 |
| ccactctcat tacaggaggc agaacagcta gtgccagaga | 3160 |
| gctcatgcaa catggacaac caccagtcac tctcaacaat | 3200 |
| aaataaatta accaaggtca tatggcggaa aaaagcaaat | 3240 |
| caggaatcag caaaccagaa ttcatttgaa gttgtggaaa | 3280 |
| gtgaagtcag cttttaaggg ttgtgtatgt taaagcatag | 3320 |
| aatggttgaa gaatcatata gaaataggag atcagtaatc | 3360 |
| tgttatgatc tagcctgtaa tagtacattc tgtaaaccaa | 3400 |
| ctgtttatat gattgttcct atacatgctt gcaacatgat | 3440 |
| gaaaagctgt ttgattggcc ttggcccta cagaatccag | 3480 |
| gttgtctatg aaaggacata ctgcactacg ggtatattga | 3520 |
| cagaaggaaa atgctttgtc cctgacaagg ctgttgtcag | 3560 |
| tgcattgaaa agaggcatgt atgctatagc aagcatagag | 3600 |

```
acaatctgct tttttattca tcagaaaggg aatacatata    3640
agatagtgac tgccattaca tcagcaatgg gctccaaatg    3680
taataataca gatactaaag ttcaaggata ttatatctgt    3720
attattggtg gaaactccgc ccctgtatat gcccctgctg    3760
gtgaagactt cagagcaatg gaggttttt ctgggattat    3800
tacatcacca catggagaag accatgacct acccggcgaa    3840
gaaatcgcaa cgtaccagat tcagggcag atagaggcaa    3880
aaatccctca tacagtgagc tccaaaaact taaaattgac    3920
tgcttttgca ggtattccat catactcatc aactagtata    3960
ttggctgctt cagaagatgg tcgtttcata tttagtcctg    4000
gtttatttcc taacctaaat cagtcagtct gtgacaacaa    4040
tgcactccct ttaatctgga ggggcctaat tgatttaacg    4080
ggatactatg aggcagtcca cccttgcaat gtgttctgtg    4120
tcttatcagg accaggtgct tcatgtgagg ccttttcaga    4160
aggaggtatt ttcaatatta cttctccaat gtgtctggtg    4200
tctaagcaaa atagatttag agcagctgag cagcagatta    4240
gctttgtctg ccaaagagtt gatatggata ttatagtgta    4280
ctgtaatggt cagaaaaaaa caatcctaac aaaaacatta    4320
gttataggcc aatgtattta tactattaca agtctcttt    4360
cactgttacc aggggttgcc cattctattg ctattgagtt    4400
gtgtgttcca gggtttcatg gctgggccac agctgcactt    4440
ttgattacat tctgcttcgg ctgggtattg attcctgcat    4480
gtacattagc tattctttta gtccttaagt tctttgcaaa    4520
tatccttcat acaagcaatc aagagaaccg attcaaagcc    4560
attctacgga aaataaagga ggagtttgaa aaaacaaagg    4600
gttccatggt ttgtgagatc tgtaagtatg agtgtgaaac    4640
attaaaggaa ttgaaggcac ataacctatc atgtgttcaa    4680
ggagagtgcc atattgctt tacccactgt gaaccgacag    4720
aaactgcaat tcaggcacat tacaaagttt gtcaagccac    4760
ccaccgattc agagaagatt taaaaagac tgtaactcct    4800
caaaatattg ggccaggctg ttaccgaaca ctaaatcttt    4840
ttaggtataa agtaggtgt tatattctga caatgtggac    4880
tcttcttctc attattgaat ccatcctctg ggcagcaagt    4920
gcagcagaaa tccccttgt ccctctctgg acagataatg    4960
ctcatggcgt tgggagtgtt cctatgcata cggatcttga    5000
attagacttc tcttttgccat ccagttctaa gtacacatac    5040
aaaagacatc tcacaaaccc agttaatgac caacagagtg    5080
tctcattgca tatagaaatt gaaagtcaag gcattggtgc    5120
tgctgttcat catcttggac attggtatga tgcaagattg    5160
aatctaaaaa cctcatttca ttgttatggt gcctgcacaa    5200
aatatcaata cccatggcac actgcaaaat gccattttga    5240
gaaagattat gagtatgaaa atagctgggc ttgcaacccc    5280
ccagattgcc caggggttgg tacaggttgt actgcttgtg    5320
gattatatct agatcaattg aagccggtag gaacagcctt    5360
taaaattata agtgtaagat acagtagaaa agtgtgcgtg    5400
cagtttggtg aagaacacct ttgtaaaaca attgatatga    5440
atgattgctt tgtgactagg catgccaaaa tatgtataat    5480
tgggactgta tctaagtttt ctcaaggtga cactctacta    5520
tttctgggc ccatggaagg aggtggtata atctttaaac    5560
actggtgtac atctacctgt cactttggag accctggtga    5600
tgtcatgggt ccaaaagata aaccattat ttgccctgaa    5640
ttcccagggc aatttaggaa aaaatgtaac tttgccacaa    5680
ctccagtttg tgaatatgat ggaaacatta tatcaggcta    5720
taagaaagta cttgcaacaa ttgattcttt ccaatcattt    5760
aacacaagca atatacactt cactgatgag agaattgaat    5800
ggagagaccc tgatggcatg cttcgggatc atattaatat    5840
tgttatttct aaagatattg attttgaaaa tttggctgag    5880
aatccttgta agtagggct ccaggcagca aacatagaag    5920
gtgcctgggg ttcaggtgtc gggtttacac tcacatgcaa    5960
ggtgtctctc acagaatgcc caacatttct tacatcaata    6000
aaggcctgtg acatggcaat ttgttatggt gcagaaagtg    6040
tgacactctc acgaggacaa aatactgtca aaattaccgg    6080
gaaaggtggc catagtggtt cttcattcaa atgctgtcat    6120
gggaaagaat gttcatcaac tggcctccaa gccagtgcac    6160
cacatctgga taaggtaaat ggtatctctg agttagaaaa    6200
cgagaaagtt tatgatgacg gtgcacctga atgtggcatt    6240
acttgttggt ttaaaaaatc aggtgaatgg gttatgggta    6280
taatcaatgg gaactgggtt gtcctaattg tcttgtgtgt    6320
actgctgctc ttttctctta tcctgttgag catcttgtgt    6360
cctgttagaa agcataaaaa atcataaatc ccacctaaca    6400
atcttcacat catgtatcga ttttcaaaca ctttatcatt    6440
tagaacttaa cttggcacta ctatctgata actgactttc    6480
attttatttt ttatatggat taattactaa aaaaaatact    6520
ctctcgtgcc gaattcgata tcaagcttat cgataccgtc    6560
gacctcgagg gggggcccgg tacccgggat cctcgcaatc    6600
cctaggagga ttaggcaagg gcttgagctc acgctcttgt    6640
gagggacaga aatacaatca ggggcagtat atgaatactc    6680
catggagaaa cccagatcta cgtatgatca gcctcgactg    6720
tgccttctag ttgccagcca tctgttgttt gcccctcccc    6760
cgtgccttcc ttgaccctgg aaggtgccac tcccactgtc    6800
ctttcctaat aaaatgagga aattgcatcg cattgtctga    6840
```

```
                                    -continued
gtaggtgtca ttctattctg gggggtgggg tggggcagga      6880
cagcaagggg gaggattggg aagacaatag caggcatgct      6920
ggggatgcgg tgggctctat ggcttctgag gcggaaagaa      6960
ccagctgggg ctcgacagct cgactctaga attgcttcct      7000
cgctcactga ctcgctgcgc tcggtcgttc ggctgcggcg      7040
agcggtatca gctcactcaa aggcggtaat acggttatcc      7080
acagaatcag gggataacgc aggaaagaac atgtgagcaa      7120
aaggccagca aaaggccagg aaccgtaaaa aggccgcgtt      7160
gctggcgttt ttccataggc tccgcccccc tgacgagcat      7200
cacaaaaatc gacgctcaag tcagaggtgg cgaaacccga      7240
caggactata aagataccag gcgtttcccc ctggaagctc      7280
cctcgtgcgc tctcctgttc cgaccctgcc gcttaccgga      7320
tacctgtccg cctttctccc ttcgggaagc gtggcgcttt      7360
ctcaatgctc acgctgtagg tatctcagtt cggtgtaggt      7400
cgttcgctcc aagctgggct gtgtgcacga acccccgtt       7440 cagcccgacc gctgcgcctt atccggtaac tatcgtcttg      7480
agtccaaccc ggtaagacac gacttatcgc cactggcagc      7520
agccactggt aacaggatta gcagagcgag gtatgtaggc      7560
ggtgctacag agttcttgaa gtggtggcct aactacggct      7600
acactagaag gacagtattt ggtatctgcg ctctgctgaa      7640
gccagttacc ttcggaaaaa gagttggtag ctcttgatcc      7680
ggcaaacaaa ccaccgctgg tagcggtggt ttttttgttt      7720
gcaagcagca gattacgcgc agaaaaaaag gatctcaaga      7760
agatcctttg atcttttcta cggggtctga cgctcagtgg      7800
aacgaaaact cacgttaagg gattttggtc atcagattat      7840
caaaaaggat cttcacctag atccttttaa attaaaaatg      7880
aagttttaaa tcaatctaaa gtatatatga gtaaacttgg      7920
tctgacagtt accaatgctt aatcagtgag gcacctatct      7960
cagcgatctg tctatttcgt tcatccatag ttgcctgact      8000
c                                                8001
```

More preferably, it further includes the Andes M-gene construct pWRG/AND-M(x) (SEQ ID NO:10), which strengthens the HPS component.

Where gene-gun delivery is contemplated, the DNA segments from different viruses can be on different particles or on the same particle, whichever results in the desired immune response. The vaccine is designed to protect against pathologies resulting from exposure to one or several hantaviruses. The vaccine can also be combined with reagents which increase the antigenicity of the vaccine, or reduce its side effects. As shown above, the delivery of a combination of vaccines by electroporation involves mixtures of DNA. This demonstrates that plasmids can be mixed and any interference from the respective DNA with each other can be overcome—another advantage of this invention.

For DNA vaccinations described here, as appropriate, when inducing cellular, humoral, and protective immune responses after DNA vaccination the preferred target cells are epidermal cells, rather than cells of deeper skin layers such as the dermis. Epidermal cells are preferred recipients of DNA vaccines because they are the most accessible cells of the body and may, therefore, be immunized non-invasively. Secondly, in addition to eliciting a humoral immune response, DNA immunized epidermal cells also elicit a cytotoxic immune response that is stronger than that generated in sub-epidermal cells. Delivery to epidermis also has the advantages of being less invasive and delivering to cells which are ultimately sloughed by the body.

Although it can be desirable to induce an immune response by delivering genetic material to a target animal, merely demonstrating an immune response is not necessarily sufficient to confer protective advantage on the animal. What is important is to achieve a protective immune response that manifests itself in a clinical difference. That is, a method is effective only if it prevents infection or reduces the severity of the disease symptoms. It is preferred that the immunization method be at least 20% effective in preventing death in an immunized population after challenge with SNV or, if a multivalent vaccine is used, at least one of the other targeted hantaviruses. More preferably, the vaccination method is 50% or more effective, and most preferably 70 100% effective, in preventing death in an immunized population. The vaccination method is shown herein to be 100% effective in the hamster models for hantavirus. Hamsters have been used extensively as the laboratory models of choice for assessment of protective immune responses to hantaviruses. In contrast, unimmunized animals are uniformly infected by challenge with hantavirus. The inventor's results indicate that vaccination with our SNV vaccines protects against infection with SNV. As is well known, high titer antibody such as achieved by the inventor is predictive of protection.

Generally, the DNA vaccine administered may be in an amount of about 5 ug-5 mg of DNA per dose and will depend on the delivery technology, subject to be treated, capacity of the subject's immune system to develop the desired immune response, and the degree of protection desired. Precise amounts of the vaccine to be administered may depend on the judgement of the practitioner and may be peculiar to each subject and antigen. Delivery technology plays an important role in determining dosage—e.g., an adjuvant may change the dosage or number of vaccinations needed.

The vaccine for eliciting an immune response against one or more viruses, may be given in a single dose schedule, or if deemed necessary or desirable, a multiple dose schedule in which a primary course of vaccination may be with 1-8 separate doses, followed by other doses given at subsequent time intervals required to maintain and or reinforce the immune response, for example, at 1 4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

In a related embodiment, this invention provides a method for raising high titers of neutralizing antibodies against Sin Nombre virus in a mammal or a bird. The method comprises the step of administering a composition comprising a SNV plasmid DNA which comprises one or more of the recombinant DNA constructs described above (including SEQ ID NO:1, SEQ ID NO:2 or SEQ ID NOT:3); and a pharmacologically acceptable carrier. The step of administering may need to be repeated as desired in order to achieve the level of titer targeted. Preferably the titer is measured to be between 100 and 10,000.

Therapeutic Use of Polyclonal and Monoclonal Antibodies

In another embodiment, the present invention relates to polyclonal antibodies from vaccinees receiving the DNA vaccines desribed above. A composition comprising the polyclonal antibodies can be used as a prophylactic or therapeutic effective in preventing onset of Sin Nombre virus infection after exposure to it, and/or in treating Sin Nombre virus disease. For example, the composition of the present invention is composed of polyclonal antiserum from a population of animals or humans vaccinated with a DNA vaccine comprised of a plasmid expressing the above-described synthetic Sin Nombre virus M gene. The polyclonal serum would contain neutralizing antibodies against Sin Nombre virus. Unlike conventional polyclonal immune serum products, the process used to make this invention (DNA vaccination to produce antibody in vaccinees) does not involve live virus and does not require the identification of patients who have survived Sin Nombre virus disease.

Similarly, animals or humans vaccinated with one of the above-described DNA vaccines can produce SNV-neutralizing monoclonal antibodies (Mab), which Mab can then be engineered into expression systems.

In one embodiment of this method, the invention contemplates a method to treat or prevent or ameliorate symptoms after onset of Sin Nombre virus infection by administering a therapeutically or prophylactically effective amount of serum of the present invention or a mixture of antibodies of the present invention to a subject in need of such treatment. The antibodies are specific for peptides encoded by the nucleic acids described herein—e.g., where the Gn and Gc are encoded by the nucleic acid of one of SEQ ID NO:1, SEQ ID NO:2 and/or SEQ ID NO:3.

The polyclonal antibodies described herein are characterized in that the antibody binds to the appropriate immunogen, i.e. Gn and Gc, as measured by assays such as ELISA, immunoprecipitation, or immunofluorescence. Also, the antibodies must neutralize Sin Nombre virus as measured by plaque reduction neutralization test (PRNT). Any antibody retaining these characteristics is related to the present invention. The polyclonal antibody may be concentrated, irradiated, and tested for a capacity to neutralize Sin Nombre virus. Serum lots with sufficiently high neutralizing antibody titers, i.e., high enough to give a detectable response in the recipient after transfer, can be pooled. The product can then be lyophilized for storage and reconstituted for use.

As described in greater detail in the examples, the present inventor has found that serum from a vaccinee immunized with a DNA vaccine comprising one of the above-described SNV sequences, contains antibodies able to neutralize hantavirus.

Given these results, polyclonal antibodies according to the present invention are suitable both as therapeutic and prophylactic agents for treating or preventing SNV infection or disease in susceptible SNV-exposed subjects. Subjects include rodents such as mice or guinea pigs, avian, and mammals (including transgenic animals), including humans.

Any active form of the antibodies can be administered. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the antibodies does not result in clearance of the antibodies before virus can be controlled, and the induced immune response to the antibodies in the subject does not induce "serum sickness" in the subject.

Treatment of individuals having SNV infection may comprise the administration of a therapeutically effective amount of anti-SNV antibodies of the present invention. The antibodies can be provided in a kit as described below. In providing a patient with antibodies, or fragments thereof, capable of binding to SNV, or an antibody capable of protecting against SNV in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg 100 pg/kg, 100 pg/kg 500 pg/kg, 500 pg/kg 1 ng/kg, 1 ng/kg 100 ng/kg, 100 ng/kg 500 ng/kg, 500 ng/kg 1 ug/kg, 1 ug/kg 100 ug/kg, 100 ug/kg 500 ug/kg, 500 ug/kg 1 mg/kg, 1 mg/kg 50 mg/kg, 50 mg/kg 100 mg/kg, 100 mg/kg 500 mg/kg, 500 mg/kg 1 g/kg, 1 g/kg 5 g/kg, 5 g/kg 10 g/kg (body weight of recipient), although a lower or higher dosage may be administered.

The antibodies capable of protecting against hantavirus are intended to be provided to recipient subjects in an amount sufficient to effect a reduction in the SNV infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Diagnostic Methods

The present invention still further pertains to a method for detecting SNV in a sample suspected of containing SNV. The method includes contacting the sample with polyclonal antibodies of the present invention which bind SNV antigens, allowing the antibody to bind to the SNV antigen(s) to form an immunological complex, detecting the formation of the immunological complex and correlating the presence or absence of the immunological complex with the presence or absence of SNV antigen in the sample. The sample can be biological, environmental or a food sample.

The language "detecting the formation of the immunological complex" is intended to include discovery of the presence or absence of SNV antigen in a sample. The presence or absence of SNV antigen can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988 555 612). Such immunoassays include antibody capture assays, antigen capture assays, and two-antibody sandwich assays. These assays are commonly used by those of ordinary skill in the art.

In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a SNV virus vaccinee and the polyclonal antibodies of the present invention, are allowed to compete for binding of the antigen. The amount of polyclonal antibody bound is then measured, and a determination is made as to whether the serum contains anti SNV antigen antibodies. This competitive ELISA can be used to indicate immunity to known protective epitopes in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1 31), and Schurs, A. H. W. M., et al. 1977 (Clin. Chim Acta 81:1 40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid. By "environmental sample" is meant a sample such as soil and water. Food samples include canned goods, meats, and others.

Yet another aspect of the present invention is a kit for detecting hantavirus in a biological sample. The kit includes a container holding one or more polyclonal antibodies of the present invention which binds a SNV antigen and instructions for using the antibody for the purpose of binding to SNV antigen to form an immunological complex and detecting the formation of the immunological complex such that the presence or absence of the immunological complex correlates with presence or absence of SNV in the sample. Examples of containers include multiwell plates which allow simultaneous detection of SNV in multiple samples.

Production of Pseudotyped Virions

Another use of the invention is a method for producing pseudotyped virions. One of the above-described DNA constructs is used to transfect cells, under conditions that pseudotyped virions or SNV glycoprotein is produced. The pseudotyped viruses are useful in serologic assays or delivery of gene therapies to endothelial cells targeted by hantavirus glycoproteins.

REFERENCES

1. Hooper J W, Custer D M, Thompson E, Schmaljohn C S. DNA vaccination with the hantaan virus m gene protects 1. hamsters against three of four HFRS hantaviruses and elicits a high-titer neutralizing antibody response in rhesus monkeys. *J Virol* 2001; 75(18): 8469-8477.
2. Fuller D H, Loudon P, Schmaljohn C. Preclinical and clinical progress of particle-mediated DNA vaccines for infectious diseases. *Methods* 2006:40:86-97.
3. Custer D M, Thompson E, Schmaljohn C S, et al. Active and passive vaccination against hantavirus pulmonary syndrome with Andes virus M genome segment-based DNA vaccine. *J Virol* 2003; 77(18):9894-9905.
4. Hooper J W, Ferro A M, and Wahl-Jensen V. Immune Serum Produced by DNA Vaccination Protects Hamsters Against Lethal Respiratory Challenge with Andes Virus. *Journal of Virology* 2008 82:1332-1338.
5. Hooper J W, Kamrud K I, Elgh F, et al. DNA vaccination with hantavirus M segment elicits neutralizing antibodies and protects against Seoul virus infection. *Virology* 1999; 255:269-278.
6. Hooper J W, Custer D M, Smith J., and Wahl-Jensen W. Hantaan/Andes virus DNA vaccine elicits a broadly cross-reactive neutralizing antibody response in nonhuman primates. *Virology* 2006; 347:208-216.
7. Condon C, Watkins S C, Celluzzi C M, et al. DNA-based immunization by in vivo transfection of dendritic cells. *Nat Med* 1996; 10:1122-1128.
8. Barry MA, Johnston SA. Biological features of genetic immunization. *Vaccine* 1997; 15:788-791.
9. Yoshida A, Nagata T, Uchijima M, et al. Advantage of gene gun-mediated over intramuscular inoculation of plasmid DNA vaccine in reproducible induction of specific immune responses. *Vaccine* 2000; 18:1725-1729.
10. Steele K E, Stabler K, VanderZanden L. Cutaneous DNA vaccination against Ebola virus by particle bombardment: histopathology and alteration of CD3-positive dendritic epidermal cells. *Vet Path* 2001; 38:203-215.
11. Monteiro-Riviere N A, Riviere J. The pig as a model for cutaneous pharmacology and toxicology research. In: Tumbleson M E, Schook L B (eds). *Advances in Swine in Biomedical Research*, Vol. 2, New York, Plenum Press, 1996, pp. 425-458.
12. Draize J H, Woodward G, Calvery H O. Methods for the study of irritation and toxicity of substances applied topically to the skin and mucous membranes. *J Pharmacol Exp Ther* 1944; 82,377-390.
13. Klinman D M, Sechler J M G, Conover J, et al. Contribution of cells at the site of DNA vaccination to the generation of antigen-specific immunity and memory. *J Immunol* 1998; 160: 2388-2392.
14. Gurunathan S, Klinman D, Seder R. DNA vaccines. 2000 *Ann Rev Immunol* 2000; 7-74.
15. McElroy A K, Smith J M, Hooper J W, Schmaljohn C S. Andes virus M genome segment is not sufficient to confer the virulence associated with Andes virus in Syrian hamsters. Virology 2004; 326(1):130-139.
16. Charles River Laboratories—Arkansas Division. Assessment of the Local Skin Reactivity and Systemic Toxicity of Hantaan Virus DNA Vaccine pWRG/HTN-M(x) following PowderJect® Delivery to Syrian Hamster Skin. Final Study Report for Protocol Number JTA00001. 2005.
17. Hammerbeck, C. D., Wahl-Jensen, V., Hooper, J. W. Hantavirus. In: Vaccines for Biodefense and Emerging and Neglected Diseases (A. D. T. Barrett and L. R. Stanberry, Eds.), pp. 379-411. London: Academic Press, 2009.
18. Jonsson C. B, J. Hooper, and G. Mertz (2008). Treatment of hantavirus pulmonary syndrome. Antiviral Res. Antiviral Res. 78:162-169.
23. Schmaljohn, C. S., and J. W. Hooper (Jan. 27, 2000). U.S. patent application Ser. No. 09/491,974; publication number 2002/0114818, published Aug. 22, 2002, entitled "DNA vaccines against hantavirus infections"
24. Hooper, J. W., C. S. Schmaljohn and M. Custer. "Extraneous DNA sequence that facilitates hantavirus gene expression. U.S. Pat. No. 7,217,812. Issued May 15, 2007.
25. Hooper, J. W., C. S. Schmaljohn. DNA Vaccines Against Hantavirus. Korean Patent 660040. Issued December 2006, and European Patent EPO 00908388.2, issued January 2007
26. Hooper, J. W. Puumala virus full-length M segment-based DNA vaccines. U.S. application Ser. No. 12/449, 504, filed Aug. 11, 2009; PCT/US2008/001847, published Jan. 15, 2009

The contents of all cited references (including literature references, issued patents, published patent applications, and co-pending patent applications) cited throughout this application are hereby expressly incorporated by reference.

What is claimed is:

1. An isolated nucleic acid sequence set forth in SEQ ID NO:1.

2. The isolated nucleic acid sequence of claim 1, wherein the sequence is SEQ ID NO:2.

3. The isolated nucleic acid sequence of claim 2, wherein the sequence is SEQ ID NO:3

4. A recombinant DNA construct comprising:
   (i) a vector, and
   (ii) the DNA fragment comprising the nucleic acid sequence set forth in SEQ ID NO:1, SEQ ID NO:2 or SEQ ID NO:3, operably linked to a promoter sequence.

5. The recombinant DNA construct of claim 4 wherein the promoter is the cytomegalovirus promoter operably linked to Intron A, or wherein the promoter is the beta-actin promoter or the SV40 promoter.

6. The recombinant DNA construct of claim 4 wherein said construct is pWRG/SN-M(opt).

7. The recombinant DNA construct of claim 4, wherein the vector is a recombinant adenovirus or recombinant vesicular stomatitis virus, or alphavirus replicon.

8. A DNA cassette comprising either SEQ ID NO:2 or SEQ ID NO:3, linked to a promoter operable in a eukaryotic expression system.

* * * * *